(12) United States Patent
Bertozzi et al.

(10) Patent No.: US 10,865,194 B2
(45) Date of Patent: Dec. 15, 2020

(54) THERAPEUTICALLY ACTIVE BICYCLIC-SULPHONAMIDES AND PHARMACEUTICAL COMPOSITIONS

(71) Applicant: FONDAZIONE ISTITUTO ITALIANO DI TECNOLOGIA, Genoa (IT)

(72) Inventors: Fabio Bertozzi, Genoa (IT); Tiziano Bandiera, Pavia (IT); Silvia Pontis, Genoa (IT); Angelo Reggiani, Genoa (IT); Francesca Giacomina, Brindisi (IT); Paolo Di Fruscia, Frosinone (IT)

(73) Assignee: FONDAZIONE ISTITUTO ITALIANO DI TECNOLOGIA, Genoa (IT)

( * ) Notice: Subject to any disclaimer, the term of this patent is extended or adjusted under 35 U.S.C. 154(b) by 0 days.

(21) Appl. No.: 15/803,362

(22) Filed: Nov. 3, 2017

(65) Prior Publication Data
US 2019/0135778 A1 May 9, 2019

(51) Int. Cl.
| | | |
|---|---|---|
| *C07D 401/12* | (2006.01) | |
| *C07D 401/14* | (2006.01) | |
| *A61P 29/00* | (2006.01) | |
| *A61P 25/28* | (2006.01) | |
| *A61K 31/4523* | (2006.01) | |

(52) U.S. Cl.
CPC ........ *C07D 401/12* (2013.01); *A61K 31/4523* (2013.01); *A61P 25/28* (2018.01); *A61P 29/00* (2018.01); *C07D 401/14* (2013.01)

(58) Field of Classification Search
CPC ... C07D 401/12; C07D 401/14; C07D 413/12
See application file for complete search history.

(56) References Cited

U.S. PATENT DOCUMENTS

| | | | |
|---|---|---|---|
| 8,907,095 B2 * | 12/2014 | Xia | C07D 401/14 544/319 |
| 2013/0281490 A1 | 10/2013 | Piomelli et al. | |
| 2013/0324576 A1 | 12/2013 | Carroll et al. | |

FOREIGN PATENT DOCUMENTS

| | | |
|---|---|---|
| WO | 2009/012277 | 1/2009 |
| WO | 2009/023180 A1 | 2/2009 |
| WO | 2009/049238 A1 | 4/2009 |
| WO | 2009/055331 | 4/2009 |
| WO | 2009/055331 A2 | 4/2009 |
| WO | 2010/009195 A1 | 1/2010 |
| WO | 2010/009195 | 10/2010 |
| WO | 2010/114958 A1 | 10/2010 |
| WO | 2011/053688 A1 | 5/2011 |

OTHER PUBLICATIONS

STN Registry Information 1, 2017.*
STN Registry Information 2, 2017.*
STN Registry Information 3, 2016.*
STN Registry Information 4, 2015.*
Registry No. 2108443-11-2, STN., Aug. 2017.*
C.B. Merrill et al., Suppression of seizure-induced glial activation in the hippocampus using a novel N-acylethanolamine acid amidase inhibitor, Department of Anatomy and Neurobiology, University of California, Irvine, Program Poster #46.09/P7, Nov. 12, 2016.
Burton, N. et al., "In vivo modulation of the Parkinsonian phenotype by Nrf2", NeuroToxicology, 27: 1094-1100 (2006).
Calignano, A. et al., "Control pain initiation by endogenous cannabinoids", Nature, 394: 277-281 (1998).
D'Agostino, G. et al., "Central administration of palmitoylethanolamide reduces hyperalgesia in mice via inhibition of NF-kB nuclear signalling in dorsal root ganglia", European Journal of Pharmacology, 613: 54-59 (2009).
Iida, K. et al., "Nrf2 Essential for the Chemopreventive Efficacy of Oltipraz against Urinary Bladder Carcinogenesis", Cancer Research, 64: 6424-6431 (2004).
Ishii, Y. et al., "Transcription Factor Nrf2 Plays a Pivotal Role in Protection against Elastase-Induced Pulmonary Inflammation and Emphysema", J. Immunol, 175: 6968-6975 (2005).
Kemeny, L. et al., "Endogenous Phospholipid Metabolite Containing Topical Product Inhibits Ultraviolet Light-Induced Inflammation and DNA Damage in Human Skin", Skin Pharmacol Physiol, 20: 155-161 (2007).
Ramos-Gomez, M. et al., "Sensitivty to carcinogenesis is increased and chemoprotective efficacy of enzyme inducers is lost in nrf2 transcription factor-deficient mice", PNAS, 98(6): 3410-3415 (2001).

(Continued)

*Primary Examiner* — Brian E McDowell
(74) *Attorney, Agent, or Firm* — Merchant & Gould P.C.

(57) ABSTRACT

Pharmaceutical compounds are disclosed having a bicyclic-sulphonamide structure of Formula 1:

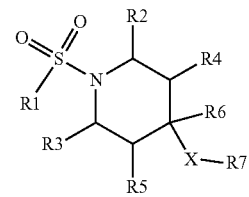

wherein R1 represents an unsubstituted or a substituted heteroaryl ring; R2, R3, R4, and R5 are independently selected from hydrogen, alkyl, hydroxyalkyl, and alkyl-O-alkyl, provided that either R2 and R3, or R4 and R5 are linked or taken together to form a bridge between the carbon atoms to which R2 and R3, or R4 and R5 respectively are directly linked, whereby the N-containing ring in Formula 1 is an azabicyclo moiety. The compounds and compositions including the compounds may be used in therapy as brain-cell-death protectants, for example, in the treatment of chronic neurodegenerative diseases. The compounds are active as inhibitors of N-acylethanolamine-hydrolysing acid amidase (NAAA) and may be used for the therapeutic treatment and prevention of pain and inflammatory disorders and other disorders which benefit from the modulation of fatty acid ethanolamides, particularly palmitoylethanolamide (PEA).

7 Claims, 1 Drawing Sheet

(56) References Cited

OTHER PUBLICATIONS

Satoh, T. et al., "Activation of the Keap1/Nrf2 pathway for neuroprotection by electrophillic phase II inducers", PNAS, 103(3): 768-773 (2006).
Shih, A. et al., "Induction of the Nrf2-driven Antioxidant Response Confers Neuroprotection during Mitochondrial Stress in Vivo", J. Biol. Chem., 280(24): 22925-22936 (2005).
Shih, A. et al., "A Small-Molecule-Inducible Nrf2-Mediated Antioxidant Response Provides Effective Prophylaxis against Cerebral Ischemia in Vivo", J. Neuroscience, 25(44): 10321-10335 (2005).
Wu, D. et al., "Production and Detection of Reactive Oxygen Species (ROS) in Cancers", J. Visual. Exp., 57: 1-4 (2011).
Xu, C. et al., "Inhibition of 7,12-Dimethylbenz(a)anthracene-Induced Skin Tumorigenesis in C57BL/6 Mice by Sulforaphane Is Mediated by Nuclear Factor E2-Related Factor 2", Cancer Res, 66: 8293-8296 (2006).
Yates, M. et al., "Potent Protection against Aflatoxin-Induced Tumorigenesis through Induction of Nrf2-Regulated Pathways by the Triterpenoid 1-[2-Cyano-3-,12-Dioxooleana-1,9(11)-Dien-28-Oyl]Imidazole", Cancer Res, 66: 2488-2494 (2006).
Zhao, J. et al., "Sulforaphane reduces infarct volume following focal cerebral ischemia in rodents", Neuroscience Letters, 393: 108-112 (2006).

* cited by examiner

THERAPEUTICALLY ACTIVE BICYCLIC-SULPHONAMIDES AND PHARMACEUTICAL COMPOSITIONS

FIELD OF THE INVENTION

The present invention relates to pharmaceutical compounds having a bicyclic-sulphonamide structure, to pharmaceutical compositions comprising said compounds and to their use in therapy. Particularly, the compounds of the invention are useful as brain-cell-death protectants and may be used, for example, in the treatment of chronic neurodegenerative diseases. Moreover, the compounds of the invention are active as inhibitors of N-acylethanolamine-hydrolysing acid amidase (NAAA) and may be used for the therapeutic treatment and prevention of pain and inflammatory disorders and other disorders which benefit from the modulation of fatty acid ethanolamides, particularly palmitoylethanolamide (PEA).

BACKGROUND OF THE INVENTION

Chronic Neurodegeneration (cND) is a collective definition used to describe the progressive axonal (white matter) and/or neuronal (grey matter) cell death in specific or multiple brain regions, as a cause/consequence of chronic diseases such as Alzheimer's disease (AD), Parkinson's disease (PD), Huntington disease (HD), Amyotrophic Lateral Sclerosis (ALS) or Multiple Sclerosis (MS). Due to the progressive ageing of the population, cND is already one of the greatest medical challenges facing the current society and prevalence is constantly growing and the prediction is that by 2040 cND will be the second cause of disability in the developed world. Over the last few decades, intense research on multiple fronts strongly advanced our understanding on the ethiopathology of the different types of cND, but despite the relevant findings, cND still remains an area of large unmet medical need.

Current knowledge suggests that cND could encompass multiple mechanisms, such as protein mis-folding, aggregation, inclusion body formation (Amyloid plaque, fibrillary tangles, lewy body, polyglutamine aggregates) and mitochondrial dysfunction. Nonetheless, oxidative stress and neuroinflammation seem recurrent conditions and rather common mechanistic elements. Once an oxidative stress occur, the human body self-protects itself by activating endogenous antioxidant responses, however if the stress is too excessive the endogenous response is no longer sufficient to counteract the damage.

Among the various endogenous antioxidant mechanisms, the erythroid 2-related factor 2 (Nrf2) is a main signaling pathway that regulates expression of a series of cytoprotective proteins at transcriptional level. As shown in FIG. 1 under basal conditions, Nrf2 binds to Kelch-like ECH-associated protein 1 (Keap1) through ETGE ('hinge') and DLG ('latch') motifs (two-site recognition), and is constantly ubiquitinated by Keap1-Cul3-Ligase complex and degraded in the 26S proteasome. In this way Nrf2 cannot translocate into the nucleus and stimulate gene expression. In presence of cellular stressors, like ROS or environmental chemicals, generated oxidative/electrophilic molecules can modify the cysteine residues of Keap1 so that the polyubiquitination of Nrf2 driven by Keap1-Cul3-Ligase complex is impaired. Nrf2 itself is liberated and can rapidly translocate into the nucleus.

Once in the nucleus, Nrf2 heterodimerizes with small MAF or JUN proteins and the complex binds to a cis-acting regulatory element found in the 5'-flanking region of genes encoding a number of cytoprotective enzymes, called antioxidant response elements (ARE). Is the expression of ARE the ultimate event allowing the transcription of the self-defense antioxidant factors.

Over the last decade evidence has emerged indicating that activation of ARE may be beneficial to the whole organism. Nrf2 mediated activation and resultant ARE-regulated gene induction result in improved outcomes in several animal models of disease, including cancer (Iida et al., Cancer Res. 2004, 64, 6424-6431; Ramos-Gomez et al., Proc. Natl. Acad. Sci. USA 2001, 98, 3410-3415; Xu et al., Cancer Res. 2006, 66, 8293-8296; Yates et al., Cancer Res. 2006, 66, 2488-2494), Huntington's (Shih et al., J. Biol. Chem. 2005, 280, 22925-22936), Parkinson's (Burton et al., Neurotoxicology 2006), stroke (Satoh et al., Proc. Natl. Acad. Sci. USA 2006, 103, 768-773; Shih et al., J. Neurosci. 2005, 25, 10321-10335; Zhao et al., Neurosci. Lett. 2006, 393, 108-112) and emphysema (Ishii et al., J. Immunol. 2005, 175, 6968-6975). These findings underline the significant therapeutic potential of targeting the Keap1-Nrf2-ARE.

In the present invention, there are described novel enhancers of the endogenous self-defense mechanism by potentiating the Nrf2 signaling pathway and ultimately ARE expression. At present, some Nrf2-ARE inducing agents have been already proposed. However, these molecules are either chemically reactive or can be converted to chemically reactive metabolites that readily oxidize or form covalent adducts with the sulfhydryl group of cysteines of Keap1. The reactivity of these compounds raises safety concerns over their long-term use while the approach underlying the invention (i.e. the activation of the pathway without affecting the cysteines of Keap1) could significantly reduce the safety risk.

Moreover, the compounds of the invention act as inhibitors of NAAA, whereby they can be used for the therapeutic treatment and prevention of pain and inflammatory disorders.

Furthermore, being the compounds of the invention inhibitors of NAAA, this additional property may add an extra therapeutic benefit in the designed pathology, since it may pharmacologically synergize with the potentiating action on the Nrf2 signaling pathway.

It is known that compounds which are members of the saturated fatty acid N-acylethanolamine (NAE) family have a marked anti-inflammatory activity in animal models of neurological diseases.

PEA has been shown to inhibit peripheral inflammation and mast cell degranulation and to exert antinociceptive effects in rats and mice (Calignano et al., Nature, 1998, 394, 277-281).

In addition to the pharmacological activities shown in animal models, PEA has been reported to attenuate skin inflammation in humans (Kemeny et al.; Skin Pharmacology and Physiology, 2007, 20, 155-161). PEA activates the nuclear receptor peroxisome proliferator-activated receptor alpha (PPAR-t), which modulates in turn the activity of pro-inflammatory regulators such as NF-Kb (D'Agostino G. et al., Eur. J. Pharmacol. 2009, 613, 54-9).

Sustaining PEA signalling at the PPAR-α by protecting PEA from degradation is therefore envisaged as a viable approach for the treatment of inflammatory and pain states.

PEA is a preferred substrate for N-acylethanolamine-hydrolysing acid amidase (NAAA), an enzyme that catalytically hydrolyses the NAE to ethanolamine and the corresponding fatty acid. Therefore, inhibition of NAAA is expected to decrease the inactivation of PEA and restore the levels of PEA in pathological conditions characterised by markedly reduced concentration of this signalling molecule.

Methods of treating pain and inflammation by using compounds which act as inhibitors of NAAA have been disclosed e.g. in WO2009/049238 and US 2013/0281490.

The previously reported studies support the notion that inhibition of NAAA can produce therapeutically useful effects and therefore the identification of new and potent NAAA inhibitors is needed in order to provide new therapeutic agents for the treatment of pain and inflammation.

US20130324576 describes sulphonyl piperidine derivatives for use in therapy, particularly for treating a disease or condition mediated by a prokineticin, specifically prokineticin 1 (PK 1) and/or prokineticin 2 (PK 2).

WO2009/023180 describes substituted bicyclic piperidinyl and piperazinyl sulphonamides useful to inhibit 11β-hydroxysteroid dehydrogenase type-1. The compounds can be used for treating metabolic syndromes, obesity, hypertension, atherosclerosis, lipid disorders, type-II diabetes, insulin resistance and pancreatitis.

WO2009/055331 and WO2010/114958 disclose further bicyclic heterocycle derivatives including an azabicyclic sulphonamide group for treating obesity, diabetes, metabolic disorders, a cardiovascular disease or a disorder relating to the activity of GPCR in a patient.

WO2011/053688 and WO2010/009195 disclose bicyclic piperidine derivatives for treating or preventing obesity, diabetes, metabolic disorders, cardiovascular diseases or disorders relating to the activity of GPR 119.

SUMMARY OF THE INVENTION

The present invention is designed to meet the huge medical need in cND and refer to the invention and use of Keap1-Nrf2 signaling pathway enhancers so that an increase ARE-mediated genes can be elicited to potentiate the self defense mechanism and provide neuroprotection.

In one aspect, the present invention relates to pharmaceutically active compounds as defined in the appended claims, namely to compounds having the structure of formula I,

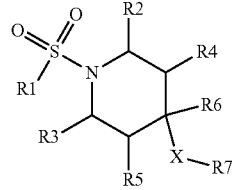

wherein:
R1 represents an unsubstituted or a substituted heteroaryl ring;
R2, R3, R4 and R5 are independently selected from the group consisting of hydrogen, alkyl, hydroxyalkyl and alkyl-O-alkyl;

Provided that either R2 and R3 or R4 and R5 are linked or taken together to form a bridge between the carbon atoms to which R2 and R3 or R4 and R5 respectively are directly linked whereby the heterocyclic moiety of Formula I has a meaning selected from the group consisting of:

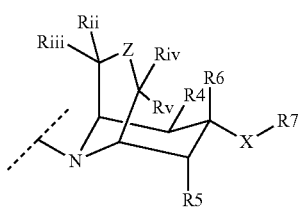

A1

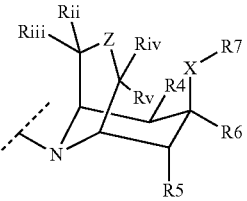

A2

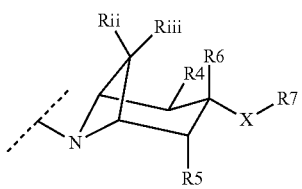

B1

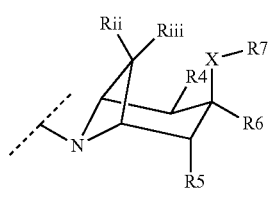

B2

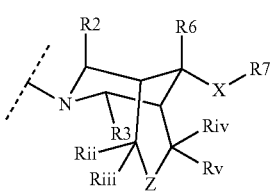

A3

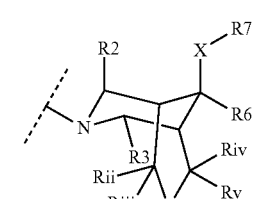

A4

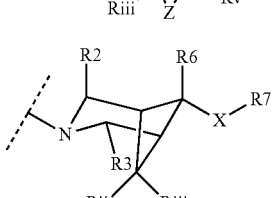

B3

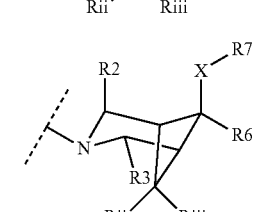

B4 wherein Z is selected from $CR^{vi}R^{vii}$, O, or can be absent;
$R^{ii}$, $R^{iii}$, $R^{iv}$ and $R^v$ are independently selected from the group consisting of hydrogen and alkyl;
$R^{vi}$ and $R^{vii}$ are independently selected from the group consisting of hydrogen and alkyl;
R6 is independently selected from the group consisting of hydrogen, alkyl, haloalkyl, cyano and halogen;
X is selected from the group consisting of $CR^{viii}R^{ix}$, O, S and $NR^x$;

$R^{viii}$, $R^{ix}$ and $R^x$ are independently selected from the group consisting of hydrogen and alkyl.

R7 is independently selected from the group consisting of alkyl, haloalkyl, cycloalky, heterocycloalkyl, aryl, heteroaryl, aryl-O-aryl, heteroaryl-O-heteroaryl and aryl-O-heteroaryl, including their pharmaceutically acceptable salts, hydrates, solvates, isomers and racemic mixtures thereof.

A further aspect of the invention relates to the compounds of formula I for use in the treatment of chronic neurodegenerative diseases and to a method for the therapeutic treatment of said diseases comprising administering to a subject in need thereof a therapeutically effective amount of a compound for formula I or of a pharmaceutical composition including such compounds.

A further aspect of the invention relates to above-mentioned compounds to be used for the treatment of acute inflammation, chronic inflammation, pain, acute pain, acute inflammatory pain, chronic inflammatory pain and neuropathic pain and to a method for therapeutic treatment of the latter-mentioned disorders comprising administering to a subject in need thereof a therapeutically effective amount of a compound of formula I or of a pharmaceutical composition comprising said compound.

DETAILED DESCRIPTION OF THE INVENTION

The present invention relates to compounds of formula I as defined in the appended claims.

The term "alkyl", as used herein, refers to saturated aliphatic hydrocarbon groups. Such term includes straight (unbranched) chains or branched chains.

Non-limiting examples of alkyl groups according to the invention are, for example, methyl, ethyl, propyl, isopropyl, n-butyl, iso-butyl, tert-butyl, n-pentyl, iso-pentyl, n-hexyl and the like.

Alkyl groups according to the present invention may be unsubstituted or substituted by one or more substituents as defined below.

The term "cycloalkyl", as used herein, refers to a saturated or partially unsaturated carbocyclic group having a single ring. It includes cycloalkenyl groups.

Non-limiting examples of cycloalkyl groups according to the invention are, for example, cyclopropane, cyclobutane, cyclopentane, cyclohexane, cycloheptane, cyclopentene, cyclohexene, cyclohexadiene and the like.

Cycloalkyl groups according to the present invention may be unsubstituted or substituted by one or more substituents as defined below.

The term "heterocycloalkyl" group, ("non-aromatic heterocycle" group), refers to a cycloalkyl group (non aromatic group) wherein at least one of the carbon atoms has been replaced by a heteroatom selected from nitrogen, oxygen and sulfur. Heterocycloalkyl groups can be unsubstituted or substituted by one or more substituents as defined below.

Examples of heterocycloalkyls include, but are not limited to, lactams, lactones, cyclic imides, cyclic thioimides, cyclic carbamates, 1-(1,2,5,6-tetrahydropyridyl), tetrahydrothiopyran, 4H-pyran, tetrahydropyran, piperidine (2-piperidinyl, 3-piperidinyl), 1,3-dioxin, 1,3-dioxane, 1,4-dioxin, 1,4-dioxane, piperazine, 1,3-oxathiane, 1,4-oxathiin, 1,4-oxathiane, tetrahydro-1,4-thiazine, 2H-1,2-oxazine, morpholine (4-morpholinyl, 3-morpholinyl, 2-morpholinyl), trioxane, hexahydro-1,3,5-triazine, tetrahydrothiophene, tetrahydrofuran (tetrahydrofuran-2-yl, tetrahydrofuran-3-yl), pyrroline, pyrrolidine, pyrrolidone, pyrrolidindione, pyrazoline, pyrazolidine, imidazoline, imidazolidine, 1,3-dioxole, 1,3-dioxolane, 1,3-dithiole, 1,3-dithiolane, isoxazoline, isoxazolidine, oxazoline, oxazolidine, oxazolidinone, thiazoline, thiazolidine, 1,3-oxathiolane, oxetane (oxetan-2-yl, oxetan-3-yl), and azetidine (azetidin-1-yl, azetidin-2-yl, azetidin-3-yl).

The term "halogen", as used herein, refers to fluorine, chlorine, bromine and iodine.

The term "aryl", as used herein, refers to a hydrocarbon consisting of an unsubstituted or substituted mono-, bi- or tricarbocyclic ring system, wherein the rings are fused together and at least one of the carbocyclic ring is aromatic. The term "aryl" means for example a cyclic aromatic such as a 6-membered hydrocarbon ring, a two six-membered fused hydrocarbon rings. Non-limiting examples of aryl groups are, for example, phenyl, alpha- or beta-naphthyl, 9,10-dihydroanthracenyl, indanyl, fluorenyl and the like. Aryl groups according to the present invention may be unsubstituted or substituted by one or more substituents as defined below.

The term "aromatic ring", as used herein, refers to a moiety wherein the constituent carbon atoms make up an unsaturated ring system, all atoms in the ring system are $sp^2$ hybridized and the total number of i-electrons is equal to $4n+2$, wherein n is an integer.

The term "heteroaryl", as used herein, refers to an aryl as defined above wherein one to four carbon atoms are independently replaced by heteroatoms chosen from the group consisting of nitrogen, oxygen and sulphur. Non-limiting examples of heteroaryl groups are, for example, pyrrolyl, furyl, thiophenyl, imidazolyl, pyrazolyl, oxazolyl, isoxazolyl, thiazolyl, isothiazolyl, indolyl, benzofuranyl, benzothiophenyl, benzimidazolyl, benzopyrazolyl, benzoxazolyl, benzoisoxazolyl, benzothiazolyl, benzoisothiazolyl, triazolyl, oxadiazolyl, tetrazolyl, pyridyl, pyrazinyl, pyrimidinyl, pyridazinyl, quinolinyl, isoquinolinyl, quinazolinyl, quinoxalinyl. The term heteroaryl, as used herein, includes also benzo-fused five- and six-membered rings where one of the rings is partially saturated. Non-limiting examples of those heteroaryl groups are, for example, 2,3-dihydro-benzofuranyl, 2,3-dihydro-benzothiophenyl, 2,3-dihydro-indolyl, 1,3-benzodioxolyl, 2,3-dihydro-1,4-benzodioxinyl, 1,2-dihydro-quinolinyl, 1,2,3,4-tetrahydro-quinolinyl, 1,2-dihydro-isoquinolinyl, 1,2,3,4-tetrahydro-isoquinolinyl.

Heteroaryl groups according to the present invention may be unsubstituted or substituted by one or more substituents as defined below.

Unless otherwise indicated, the term "substituted", as used herein, means that one or more hydrogen atoms of the above mentioned groups are replaced with another non-hydrogen atom or functional group referred to as substituent, provided that normal valencies are maintained and that the substitution results in a stable compound. Non-limiting example of substituents are, for example, OH, $C_1$-$C_6$alkyl, aryl, $C_1$-$C_6$alkylaryl, $C_3$-$C_6$cycloalkyl, O—$C_1$-$C_6$alkyl, O—$C_3$-$C_6$cycloalkyl, O-aryl, O—$C_1$-$C_6$alkylaryl, heteroaryl, O-heteroaryl, O-heterocycloalkyl, trifluoromethyl, difluoromethyl, trifluoromethoxy, difluoromethoxy, acyl, aroyl, heteroaroyl, halogen, nitro, cyano, $COOR^z$, alkylthio, arylthio, alkylsulfinyl, arylsulfinyl, alkylsulfonyl, arylsulfonyl, —O—C(=O)—$NR^hR^k$, —C(=O)—$NR^hR^k$, and —$NR^pR^q$, wherein each of $R^z$, $R^h$, and $R^k$, independently represents hydrogen, $C_1$-$C_6$alkyl, $C_3$-$C_6$cycloalkyl, aryl, $C_1$-$C_6$alkylaryl, heteroaryl, hetero $C_3$-$C_{66}$cycloalkyl, $R^p$ and $R^q$ independently represents hydrogen, $C_1$-$C_6$alkyl, $C_3$-$C_6$cycloalkyl, aryl, $C_1$-$C_6$alkylaryl, heteroaryl, hetero $C_3$-$C_6$cycloalkyl, $COR^z$, $COOR^z$, —C(=O)—$NR^hR^k$, —S(=O)$_2$—R$^z$, and —S(=O)$_2$—NR$^h$R$^k$, and when R$^h$ and R$^k$, or R$^p$ and R$^q$ are taken together with the nitrogen atom to which they are bound, the group —NR$^h$R$^k$ or the group NR$^p$R$^q$ represent a heterocycloalkyl residue, and wherein the terms alkyl, cycloalkyl, aryl, heteroaryl, heterocyclyl are as above defined.

Preferred substituents are OH, C$_1$-C$_6$alkyl, O—C$_1$-C$_6$alkyl, trifluoromethyl, difluoromethyl, halogen, C$_3$-C$_6$cycloalkyl, C$_{4-6}$heterocycloalkyl, O—C$_3$-C$_6$cycloalkyl, O—C$_4$-C$_6$heterocycloalkyl, trifluoromethoxy, difluoromethoxy, cyano, —NR$^p$R$^q$ and COOR$^z$ wherein R$^z$ is selected from the group consisting of H, methyl, ethyl, propyl, butyl, i-propyl, t-butyl, and R$^p$ and R$^q$ are independently selected from H, methyl, ethyl, butyl, i-propyl, phenyl, COR$^z$, COOR$^z$, —C(=O)—NR$^h$R$^k$, and —S(=O)$_2$—R$^z$. More preferred substituents are selected from OH, methyl, methoxy, chlorine, fluorine, trifluoromethyl, trifluoromethoxy, cyano, —NR$^p$R$^q$ and COOR$^z$ wherein R$^z$ is selected from the group consisting of H, methyl, ethyl and t-butyl, and R$^p$ and R$^q$ are independently selected from H, methyl, ethyl, butyl, i-propyl, phenyl, and acyl.

In the compounds of formula I of the invention:
R1 is preferably a 5- or 6-membered heteroaryl group, more preferably selected from the group consisting of pyrazolyl, imidazolyl, isoxazolyl, thienyl, pyridyl and pyrimidyl; the mentioned heteroaryl groups may be unsubstituted or substituted, preferably mono- or bi-substituted with C$_1$-C$_6$alkyl, halo C$_1$-C$_6$alkyl, C$_3$-C$_6$cycloalkyl, aryl, heteroaryl, COR$^{xi}$, COOR$^{xi}$, heterocycloalkyl, CONHR$^{xi}$, CONR$^{xi}$R$^{xii}$, OH, O—C$_1$-C$_6$alkyl, O—C$_3$-C$_6$cycloalkyl, O-heterocycloalkyl, O-heteroaryl, O-aryl, O-halo C$_1$-C$_6$alkyl, C$_1$-C$_6$alkyl-O—C$_1$-C$_6$alkyl, C$_1$-C$_6$alkyl-O—C$_3$-C$_6$cycloalkyl, C$_1$-C$_6$alkyl-O-heterocycloalkyl, C$_1$-C$_6$alkyl-O-aryl, CN, NO$_2$, NR$^{viii}$R$^{xiv}$, N(R$^{xii}$)COR$^{xiii}$, N(R$^{xii}$)COOR$^{xiv}$, N(R$^{xii}$)CONR$^{xii}$R$^{xiv}$, N(R$^{xii}$)SO2R$^{xiii}$, SO2R$^{xiii}$, halogen and hydroxy-C$_1$-C$_6$alkyl;

R$^{xi}$ is selected from the group consisting of hydrogen, C$_1$-C$_6$alkyl, aryl, heteroaryl;

R$^{xii}$ is selected from the group consisting of hydrogen, C$_1$-C$_6$alkyl;

R$^{xiv}$ is selected from the group consisting of hydrogen, C$_1$-C$_6$alkyl, C$_3$-C$_6$cycloalkyl, aryl, heteroaryl and hydroxy-C$_1$-C$_6$alkyl;

R$^{xiv}$ is selected from the group consisting of hydrogen, C$_1$-C$_6$alkyl;

X is preferably O;

R7 is selected from the group consisting of unsubstituted or substituted aryl, heteroaryl, aryl-O-aryl, heteroaryl-O-heteroaryl and aryl-O-heteroaryl, more preferably from the group consisting of phenyl, pyrimidinyl, pyridinyl, pyrazinyl, pyridazinyl, 1,3-benzoxazolyl, quinolynyl, quinoxalynyl, which may be optionally substituted with C$_1$-C$_6$alkyl, C$_1$-C$_4$alkyl-O—C$_1$-C$_4$alkyl, O—C$_1$-C$_6$alkyl, halo C$_1$-C$_6$alkyl, CN, halogen, hydroxy-C$_1$-C$_4$alkyl or COR$^{xi}$;

R6 is preferably hydrogen or C$_1$-C$_4$ alkyl.

The compound (1R,3r,5S)-3-(4-butylphenoxy)-8-[(3,5-dimethyl-1H-pyrazol-4-yl)sulfonyl]-8-azabicyclo[3.2.1]octane (ARN16186), which falls within the scope of formula I, is hereby disclaimed as it is the subject of a separate patent application.

BRIEF DESCRIPTION OF THE DRAWINGS

In the annexed drawings.

EXPERIMENTAL PART: SYNTHESIS OF THE COMPOUNDS OF THE INVENTION

Figure 1:
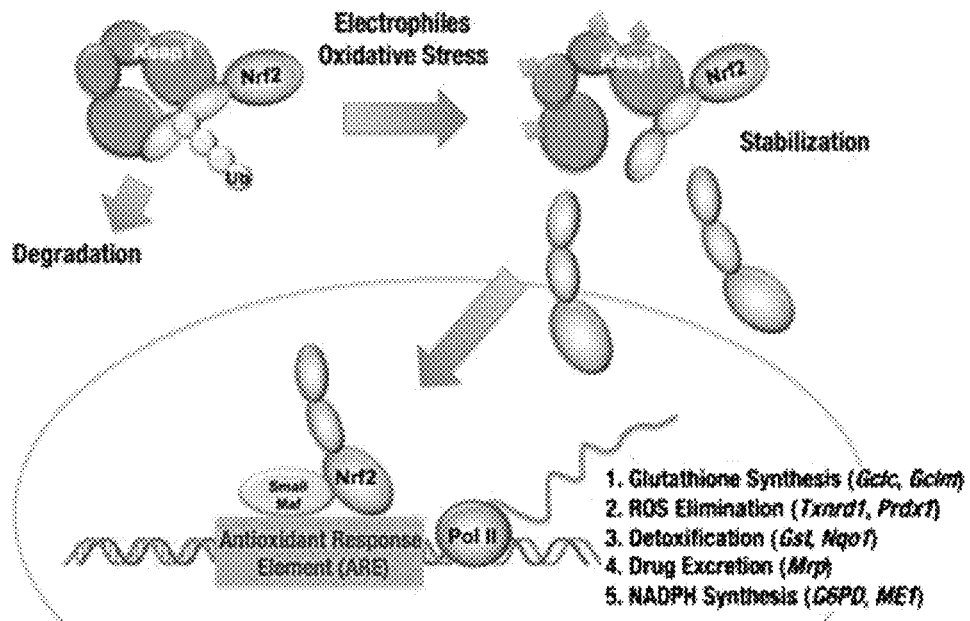
FIG. 1 is a schematic representation showing the mechanism of Nrf2 activation for the self-defence of cells against oxidative stress.
Figure 2:
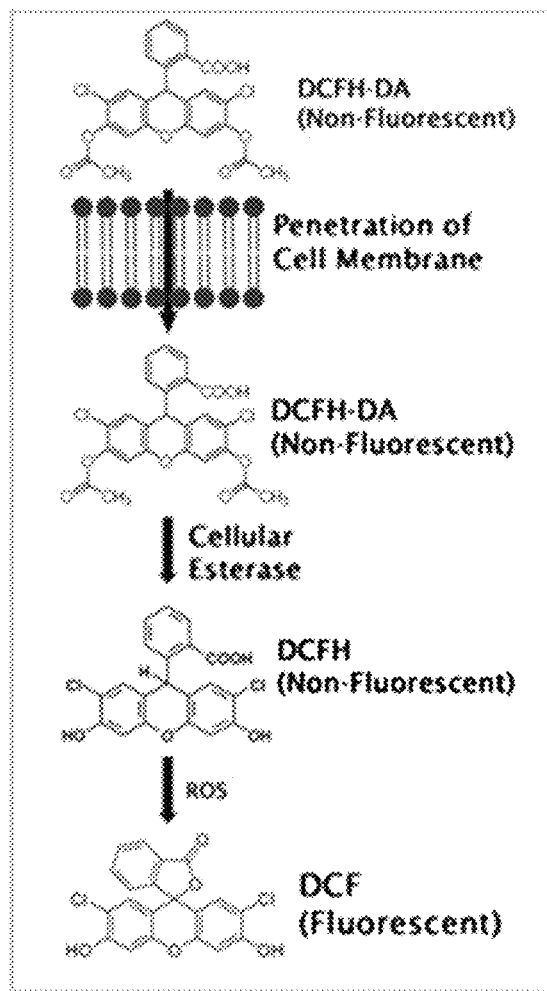
FIG. 2 is a schematic representation showing the reaction for formation of fluorescence in step 3) of the procedure for measurement of ROS production.

Solvents and reagents were obtained from commercial suppliers and were used without further purification.

List of abbreviations: acetonitrile (MeCN), ammonium chloride (NH$_4$Cl) tert-butanol (t-BuOH), tert-butylcarboxylate (Boc) n-butyl lithium (n-BuLi) chloroform-d (CDCl$_3$), copper chloride (CuCl), deuterium oxide (D$_2$O), dichloromethane (DCM), (diethylamino)sulfur trifluoride (DAST), diethyl ether (Et$_2$O), diisopropyl azodicarboxylate (DEAD), di-tert-butyl dicarbonate (Boc$_2$O), dithiotreitol (DTT), ethanol (EtOH), ethyl acetate (EtOAc), methanol (MeOH), N,N-dimethylformamide (DMF), palladium on charcoal (Pd/C), potassium carbonate (K$_2$CO$_3$), potassium hydroxide (KOH), potassium tert-butoxide (t-BuOK), pyridine (py), sodium carbonate (Na$_2$CO$_3$), sodium hydroxide (NaOH), sodium periodate (NaIO$_4$), sodium sulphate (Na$_2$SO$_4$), tetrachlorotitanium (TiCl$_4$), tetrahydrofuran (THF), triethylamine (Et$_3$N), triflic anhydride (Tf$_2$O), trifluoroacetic acid (TFA), triphenylphosphine (PPh$_3$).

Automated column chromatography purifications were performed on Teledyne ISCO apparatus (CombiFlash® Rf) with pre-packed silica gel columns of different sizes (Redisep). Hydrogenation reactions were performed on H-Cube® continuous hydrogenation equipment (SS-reaction line version), employing disposable catalyst cartridges (CatCart®) preloaded with the required heterogeneous catalyst. NMR experiments were run on a Bruker Avance III 400 system (400.13 MHz for $^1$H, and 100.62 MHz for $^{13}$C), equipped with a BBI probe and Z-gradients and Bruker FT NMR Avance III 600 MHz spectrometer equipped with a 5 mm CryoProbe™ QCI $^1$H/$^{19}$F-$^{13}$C/$^{15}$N-D quadruple resonance, a shielded z-gradient coil and the automatic sample changer SampleJet™ NMR system (600 MHz for $^1$H, 151 MHz for $^{13}$C and 565 MHz for $^{19}$F). Chemical shifts for $^1$H and $^{13}$C spectra were recorded in parts per million using the residual non-deuterated solvent as the internal standard (for CDCl$_3$: 7.26 ppm, $^1$H and 77.16 ppm, $^{13}$C; for DMSO-d$_6$: 2.50 ppm, $^1$H; 39.52 ppm, $^{13}$C, for D$_2$O: TSP as internal standard 0.00 ppm). UPLC/MS analyses were run on a Waters ACQUITY UPLC/MS system consisting of a SQD (Single Quadrupole Detector) Mass Spectrometer equipped with an Electrospray Ionization interface and a Photodiode Array Detector. PDA range was 210-400 nm. Electrospray ionization in positive and negative mode was applied. Mobile phases (A) 10 mM NH$_4$OAc in H$_2$O, pH 5; (B) 10 mM NH$_4$OAc in MeCN/H$_2$O (95:5) pH 5. Analyses were performed either with method A, B or C.

Method A (generic)
Gradient: 5 to 95% B over 3 min. Flow rate 0.5 mL/min. T 40° C.
Pre column: Vanguard BEH Cis (1.7 μm 2.1×5 mm).
Column: BEH C18 (1.7 μm 2.1×50 mm)

Method B (polar)
Gradient: 0 to 50% B over 3 min. Flow rate 0.5 mL/min. T 40° C.

Pre column: VanGuard HSS T3 C$_{18}$ (1.7 μm 2.1×5 mm).
Column HSS T3 (1.8 μm 2.1×50 mm)
Method C (apolar)
Gradient: 50 to 100% B over 3 min. Flow rate 0.5 mL/min. T 40° C.
Pre column: Vanguard BEH Cis (1.7 μm 2.1×5 mm).
Column: BEH C18 (1.7 μm 2.1×50 mm)

tert-Butyl 3-hydroxy-8-azabicyclo[3.2.1]octane-8-carboxylate

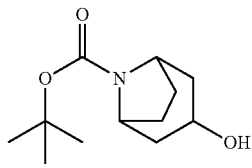 [SMILES: CC(C)(C)OC(=O)N1C2CCC1CC(O)C2]

tert-Butyl 3-oxo-8-azabicyclo[3.2.1]octane-8-carboxylate (0.22 g, 1 eq., 9.74 mmol) was dissolved in MeOH (25 mL) and the resulting solution was cooled to 0° C. Sodium borohydride (0.9 g, 2.5 eq., 24.35 mmol) was slowly added and the mixture was stirred at room temperature for 1 h. The reaction mixture was quenched with a saturated solution NH$_4$Cl (15 mL) and extracted with DCM (2×15 mL). The organic extracts were dried over Na$_2$SO$_4$ and concentrated in vacuo to furnish the crude product, which was purified by flash chromatography eluting with cyclohexane/EtOAc (0 to 60%) to give the endo product (0.12 g, 56%) and exo product (0.66 g, 30%) as white solids. UPLC-MS (method A): Rt. 1.95 min (TIC), ionization ES$^+$228 [M+H]$^+$ endo product; Rt. 1.84 min (TIC), ionization ES$^+$228 [M+H]$^+$ exo product.

Endo: $^1$H NMR (400 MHz, DMSO-d$_6$): δ 4.60 (d, J=2.4 Hz, 1H), 4.03-3.95 (m, 2H), 3.94-3.87 (m, 1H), 2.20-2.07 (m, 2H), 1.93-1.70 (m, 4H), 1.69-1.57 (m, 2H), 1.39 (s, 9H).

Exo: $^1$H NMR (400 MHz, DMSO-d$_6$): δ 4.60 (d, J=5.5 Hz, 1H), 4.09-3.97 (m, 2H), 3.95-3.83 (m, 1H), 1.79 (d, J=16.8 Hz, 4H), 1.65-1.53 (m, 2H), 1.41 (s, 9H), 1.38-1.29 (m, 2H).

tert-Butyl (1R,3r,5S)-3-hydroxy-9-azabicyclo[3.3.1]nonane-9-carboxylate

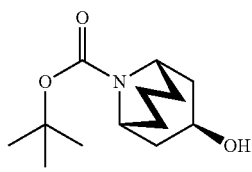

tert-Butyl 3-oxo-9-azabicyclo[3.3.1]nonane-9-carboxylate (1.0 g, 1 eq., 4.18 mmol) was dissolved in MeOH (10 mL) and the resulting solution was cooled to 0° C. Sodium borohydride (0.4 g, 2.5 eq., 10.5 mmol) was slowly added and the mixture was stirred at room temperature for 1 h. The reaction mixture was quenched with a saturated solution of NH$_4$Cl (15 mL) and extracted with DCM (2×15 mL). The organic extracts were dried over Na$_2$SO$_4$ and concentrated in vacuo to furnish the crude product, which was purified by flash chromatography eluting with cyclohexane/EtOAc (0 to 80%) to give the endo product as white solid (1.0 g, 98%). UPLC-MS (method A): Rt. 1.97 min (TIC); ionization ES$^+$242 [M+H]$^+$. $^1$H NMR (400 MHz, DMSO-d$_6$): δ 4.63 (d, J=4.7 Hz, 1H), 4.24 (t, J=13.6 Hz, 2H), 3.45-3.36 (m, 1H), 2.18-2.02 (m, 3H), 1.51-1.32 (m, 14H), 1.29-1.19 (m, 2H).

3-Isopropyl-5-methyl-1H-pyrazole-4-sulfonyl chloride

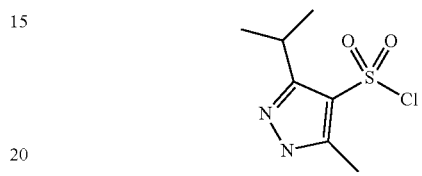

To a solution of sulfurochloridic acid (1.5 mL, 5.5 eq., 22.2 mmol) in chloroform (20 mL) was added dropwise 3-isopropyl-5-methyl-1H-pyrazole (0.5 g, 1 eq., 4.03 mmol) in chloroform (2 mL) under inert atmosphere at 0° C. The reaction was then heated to 60° C. for 15 h. The mixture was cooled to room temperature, and thionyl chloride (2.5 mL, 1.1 eq., 34.3 mmol) was gradually added. The reaction was heated to 60° C. for a further 2 h, then cooled to room temperature and added to a stirred mixture of DCM (10 mL) and ice cold water (15 mL). The organic layer was separated and the aqueous layer was extracted with DCM (2×15 mL). The combined organic layer was dried over Na$_2$SO$_4$ and concentrated in vacuo to give a yellow solid, which was used without further purification (0.5 g, 57%).

2-Chloro-4-methyl-1,3-benzoxazole

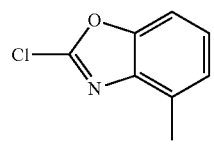

To a mixture of 4-methyl-3H-1,3-benzoxazol-2-one (80.36 g, 1.0 eq., 2.44 mmol) in POCl$_3$ (1.4 mL, 6 eq., 14.64 mmol) was added pyridine (0.2 mL, 1.0 eq., 2.44 mmol) at room temperature. The resulting reaction mixture was heated at 120° C. and stirred at this temperature for 2.5 h. The reaction was cooled to room temperature, carefully poured into water (15 mL) and the aqueous phase was extracted with EtOAc (2×15 mL). The combined organic layers were washed with brine (20 mL), dried over Na$_2$SO$_4$ and concentrated in vacuo to furnish the crude product, which was purified by flash chromatography eluting with cyclohexane/EtOAc (0 to 80%) to give the pure title compound as yellow oil (0.21 g, 52%). UPLC-MS (method A): Rt. 2.51 min. $^1$H NMR (400 MHz, DMSO-d$_6$): δ 7.56 (d, J=8.2 Hz, 1H), 7.35 (t, J=7.9 Hz, 1H), 7.26 (dt, J=7.6, 1.0 Hz, 1H), 1.40 (s, 3H).

(5-Chloropyrazin-2-yl)methanol

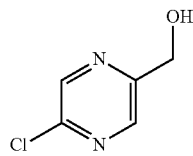

Methyl 5-chloropyrazine-2-carboxylate (2.0 g, 1 eq., 11.6 mmol) was dissolved in MeOH (15 mL) and the solution was cooled to 0° C. Sodium borohydride (1.1 g, 2.5 eq., 29 mmol) was slowly added and the reaction mixture was stirred at room temperature for 1 h. The reaction mixture was quenched with a saturated solution of NH$_4$Cl (15 mL) and extracted with DCM (2×15 mL). The organic extracts were dried over Na$_2$SO$_4$ and concentrated in vacuo to furnish the crude product, which was purified by flash chromatography eluting with cyclohexane/EtOAc (0 to 60%) to give the pure title compound as colourless oil (1.59 g, 95%). $^1$H NMR (400 MHz, DMSO-d$_6$): δ 8.73 (d, J=1.4 Hz, 1H), 8.54 (d, J=1.3 Hz, 1H), 5.68 (t, J=5.8 Hz, 1H), 4.65 (d, J=5.7 Hz, 2H).

2-Chloro-5-(ethoxymethyl)pyrazine

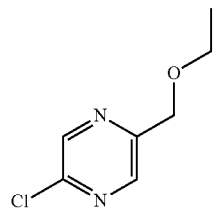

(5-Chloropyrazin-2-yl)methanol (0.3 g, 1 eq., 2.08 mmol) and iodoethane (0.17 mL, 1 eq., 2.08 mmol) were dissolved in THF (10 mL) and the solution was cooled to 0° C. Sodium hydride (0.25 g, 3 eq., 6.24 mmol) was then added and the reaction mixture was stirred at room temperature for 16 h. The reaction mixture was quenched with a saturated solution of NHCO$_3$ (15 mL) and extracted with EtOAc (2×15 mL). The organic extracts were dried over Na$_2$SO$_4$ and concentrated in vacuo to furnish the crude product, which was purified by flash chromatography eluting with cyclohexane/EtOAc (0 to 80%) to give the pure title compound as colourless oil (0.03 g, 9%). UPLC-MS (method A): Rt. 1.69 min (TIC); ionization ES$^+$173 [M+H]$^+$. $^1$H NMR (400 MHz, DMSO-d$_6$): 8.77 (d, J=1.4 Hz, 1H), 8.53 (d, J=1.3 Hz, 1H), 4.62 (s, 2H), 3.59 (q, J=7.0 Hz, 2H), 1.19 (t, J=7.0 Hz, 3H).

2-(2-Oxoethoxy)acetaldehyde

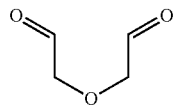

To 1,4-anhydroerythritol (5 g, 1 eq., 48 mmol) in water (70 mL) was added NaIO$_4$ (5.1 g, 0.5 eq., 24 mmol). The resulting reaction was allowed to stir for 18 h, then MeCN (70 mL) was added. The resulting reaction was allowed to stir for 30 min. then the reaction mixture was filtered and concentrated in vacuo. The crude product was used in the following step without any further purification (4.9 g, 99%). UPLC-MS (method B): Rt. 0.47 min (TIC); ionization ES$^+$103 [M+H]$^+$.

9-Benzyl-3-oxa-9-azabicyclo[3.3.1]nonan-7-one

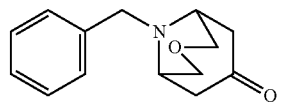 [SMILES: O=C1CC2COCC(C1)N2Cc1ccccc1]

To a solution of 1,4-anhydroerythritol (4.9 g, 1 eq., 48 mmol), acetone-1,3-dicarboxylic acid (7 g, 1 eq., 48 mmol) and HCl conc. (2.5 mL) in water (70 mL) was added benzylamine (6.14 mL, 1.38 eq., 66 mmol). The resulting reaction was allowed to stir for 1.5 h, then the reaction was heated to 50° C. and allowed to stir at this temperature for 5 h. The reaction mixture was cooled to 0° C., basified to pH 10 with 1N NaOH, and extracted with Et$_2$O. The organic extract was dried over K$_2$CO$_3$, filtered and concentrated in vacuo, and the residue obtained was purified by flash chromatography eluting with cyclohexane/EtOAc (0 to 80%) to give the pure title compound as white solid (2.16 g, 19%). UPLC-MS (method A): Rt. 0.59 min (TIC); ionization ES$^+$232 [M+H]$^+$. $^1$H NMR (400 MHz, DMSO-d$_6$): δ 7.47-7.39 (m, 2H), 7.39-7.32 (m, 2H), 7.30-7.21 (m, 1H), 3.90 (s, 2H), 3.68-3.53 (m, 4H), 3.06 (d, J=5.8 Hz, 2H), 2.77 (dd, J=15.8, 5.9 Hz, 2H), 2.18-2.04 (m, 2H).

3-Oxa-9-azabicyclo[3.3.1]nonan-7-one

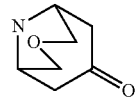

A solution of 9-benzyl-3-oxa-9-azabicyclo[3.3.1]nonan-7-one (2.16 g, 1.0 eq., 9.33 mmol) in EtOH (50 mL) was initially stirred, followed by subsequent addition of 10% Pd/C (2 g) and cyclohexene (9.5 mL, 10 eq., 93.3 mmol). The reaction mixture was stirred at 80° C. until complete conversion of the starting material. The crude mixture was filtered through a pad of Celite eluting with EtOAc, and, after removal of the solvent under reduced pressure, the crude product was used in the next step without any further purification (1.32 g, 99% crude). UPLC-MS (method A): Rt. 0.37 min (TIC); ionization ES$^+$142 [M+H]$^+$. $^1$H NMR (400 MHz, DMSO-d$_6$): δ 3.64-3.56 (m, 4H), 3.26-3.20 (m, 2H), 2.55 (d, J=6.1 Hz, 1H), 2.52-2.50 (m, 1H), 2.32-2.19 (m, 2H).

tert-Butyl 7-oxo-3-oxa-9-azabicyclo[3.3.1]nonane-9-carboxylate

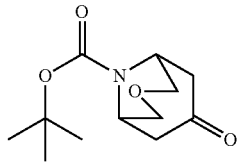 [SMILES: CC(C)(C)OC(=O)N1C2COCC1CC(=O)C2]

To a solution of 3-oxa-9-azabicyclo[3.3.1]nonan-7-one (1.32 g, 1 eq., 9.3 mmol) in EtOH (15 mL) was added di-tert-butyldicarbonate (2.25 g, 1.1 eq., 10.3 mmol) and Et$_3$N (2 mL, 1.5 eq., 14 mmol), and the resulting solution was stirred for 3 h. Then, water (20 mL) was added, and the solution was extracted with EtOAc (2×15 mL). The organic extracts were dried over Na$_2$SO$_4$ and concentrated in vacuo to furnish the crude product, which was used in the next step without any further purification (2.23 g, 99% crude). UPLC-MS (method A): Rt. 1.78 min (TIC); ionization ES$^+$242 [M+H]$^+$. $^1$H NMR (400 MHz, DMSO-d$_6$): δ 4.37-4.18 (m, 2H), 3.73 (t, J=10.0 Hz, 2H), 3.53 (ddd, J=11.4, 2.3, 1.1 Hz, 2H), 2.56-2.50 (m, 2H), 2.38-2.21 (m, 2H), 1.45 (s, 9H).

tert-Butyl (1R,3r,5S)-7-hydroxy-3-oxa-9-azabicyclo[3.3.1]nonane-9-carboxylate

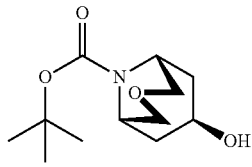

tert-Butyl 7-oxo-3-oxa-9-azabicyclo[3.3.1]nonane-9-carboxylate (2.23 g, 1 eq., 9.25 mmol) was dissolved in MeOH (25 mL) and the resulting solution was cooled to 0° C. Sodium borohydride (0.9 g, 2.5 eq., 23.1 mmol) was slowly added and the mixture was stirred at room temperature for 1 h. The reaction mixture was quenched with a saturated solution of NH$_4$Cl (15 mL) and extracted with DCM (2×15 mL). The organic extracts were dried over Na$_2$SO$_4$ and concentrated in vacuo to furnish the crude product, which was used in the next step without any further purification (1.9 g, 83%). UPLC-MS (method A): Rt. 1.81 min (TIC); ionization ES$^+$244 [M+H]$^+$. $^1$H NMR (400 MHz, DMSO-d$_6$): δ 5.06 (d, J=11.2 Hz, 1H), 4.02-3.88 (m, 2H), 3.81-3.65 (m, 3H), 3.57 (ddd, J=11.5, 2.8, 1.2 Hz, 2H), 2.14-1.91 (m, 2H), 1.71-1.55 (m, 2H), 1.41 (s, 9H).

7-Benzyl-3-oxa-7-azabicyclo[3.3.1]nonan-9-one

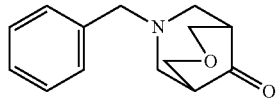 [SMILES: O=C1C2COCC1CN(Cc1ccccc1)C2]

At 65° C., a solution of tetrahydropyran-4-one (1.0 g, 1 eq., 10 mmol), benzylamine (2.18 mL, 2 eq., 20 mmol) and acetic acid (1.1 mL, 2 eq., 20 mmol) in dry MeOH (40 mL) was added over a period of 1 h to a suspension of paraformaldehyde (1.2 g, 4 eq., 40 mmol). The resulting mixture was allowed to stir for 1 h at this temperature, then cooled to room temperature. The reaction was quenched with water, basified with 1N NaOH, and extracted with Et$_2$O. The organic extract was dried over Na$_2$SO$_4$, filtered and concentrated in vacuo, and the residue obtained was purified by flash chromatography eluting with cyclohexane/EtOAc (7:3) to give the pure title compound as white solid (1.1 g, 48%). UPLC-MS: t$_R$=0.97 min (generic method); MS (ESI) m/z calcd for C$_{14}$H$_{18}$NO$_2$ (M+H)$^+$: 232.1, found: 232.1. $^1$H NMR (400 MHz, CDCl$_3$) δ 7.40-7.26 (m, 5H), 4.26 (d, J=10.9 Hz, 2H), 3.92 (dd, J=11.1, 2.6 Hz, 2H), 3.60 (s, 2H), 3.16 (dd, J=11.2, 2.0 Hz, 2H), 2.98 (dd, J=11.2, 6.0 Hz, 2H), 2.57 (br s, 2H).

7-Benzyl-3-oxa-7-azabicyclo[3.3.1]nonan-9-ol

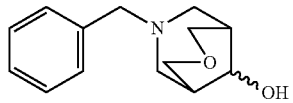 [SMILES: OC1C2COCC1CN(Cc1ccccc1)C2]

7-Benzyl-3-oxa-7-azabicyclo[3.3.1]nonan-9-one (1.1 g, 1 eq., 4.76 mmol) was dissolved in a 3:1 mixture MeOH/THF (15 mL) and the resulting solution was cooled to 0° C. Sodium borohydride (0.452 g, 2.5 eq., 11.9 mmol) was slowly added and the mixture was stirred at room temperature for 3 h. The reaction mixture was quenched with 1N NaOH (10 mL) solution and extracted with EtOAc (2×30 mL). The organic extracts were dried over Na$_2$SO$_4$ and concentrated in vacuo to furnish a crude product, as a mixture of two stereoisomers, which was used in the next step without any further purification (0.95 g, 86%). UPLC-MS: t$_R$=1.00 min (generic method); MS (ESI) m/z calcd for C$_{14}$H$_{20}$NO$_2$ (M+H)$^+$: 234.1, found: 234.2.

3-Benzyl-8,8-dimethoxy-3-azabicyclo[3.2.1]octane

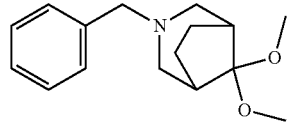 [SMILES: COC1(OC)C2CCC1CN(Cc1ccccc1)C2]

A mixture of cyclopentanone (1.0 g, 1 eq., 11.9 mmol), N,N-bis(methoxymethyl)-1-phenyl-methanamine (2.32 g, 1 eq., 11.9 mmol) and trimethylsilyl chloride (2.85 g, 2.2 eq., 26.18 mmol) was added dropwise to acetonitrile (70 mL) upon stirring at 40° C. during 3 h. The reaction mixture was additionally stirred for 16 h at room temperature, then quenched and basified to pH 8 with sat. aq. NaHCO$_3$ solution (20 mL) and the crude product extracted with EtOAc (2×50 mL). The organic extract was dried over Na$_2$SO$_4$, filtered and concentrated in vacuo, and the residue obtained was purified by flash chromatography eluting with cyclohexane/EtOAc (9:1) to give the pure title compound as a yellow oil (0.3 g, 12%).

3-Benzyl-3-azabicyclo[3.2.1]octan-8-one

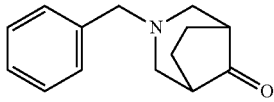 [SMILES: O=C1C2CCC1CN(Cc1ccccc1)C2]

In a round bottomed flask, to a solution of 3-benzyl-8,8-dimethoxy-3-azabicyclo[3.2.1]octane (0.25 g, 1 eq., 0.95 mmol) in DCM (10 mL) was slowly added a mixture of trifluoroacetic acid (2.0 mL) and water (2.0 mL). The resulting solution was stirred overnight at room temperature. Upon completion of the reaction, trifluoroacetic acid was evaporated and sat. aq. NaHCO$_3$ solution was added to pH 8. The crude product was extracted with DCM (2×20 mL), and the combined organic phase extracted, dried over Na$_2$SO$_4$, filtered and concentrated in vacuo. The crude product was purified by flash chromatography eluting with cyclohexane/DCM (1:9) to give the pure title compound as a yellowish oil (0.14 g, 68%). UPLC-MS: $t_R$=2.46 min (generic method); MS (ESI) m/z calcd for C$_{14}$H$_{18}$NO (M+H)$^+$: 216.1, found: 216.1. $^1$H NMR (400 MHz, DMSO-d$_6$) δ 7.37-7.32 (m, 4H), 7.29-7.23 (m, 1H), 3.59 (s, 2H), 2.97-2.86 (m, 2H), 2.41 (d, J=11.1 Hz, 2H), 2.13-2.04 (m, 2H), 1.98-1.88 (m, 2H), 1.83-1.74 (m, 2H).

3-Benzyl-3-azabicyclo[3.2.1]octan-8-ol

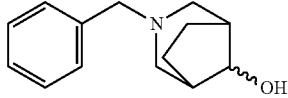 [SMILES: OC1C2CCC1CN(Cc1ccccc1)C2]

3-Benzyl-3-azabicyclo[3.2.1]octan-8-one (0.14 g, 1 eq., 0.65 mmol) was dissolved in MeOH (5 mL) and the resulting solution was cooled to 0° C. Sodium borohydride (0.062 g, 2.5 eq., 1.63 mmol) was slowly added and the mixture was stirred at room temperature for 2 h. The reaction mixture was quenched with 1N NaOH (10 mL) solution and extracted with EtOAc (2×30 mL). The organic extracts were dried over Na$_2$SO$_4$ and concentrated in vacuo to furnish a crude product, which was used in the next step without any further purification (0.1 g, 71%). UPLC-MS: $t_R$=1.00 min (generic method); MS (ESI) m/z calcd for C$_{14}$H$_{20}$NO (M+H)$^+$: 218.2, found: 218.4.

3-Benzyl-9,9-dimethoxy-3-azabicyclo[3.3.1]nonane

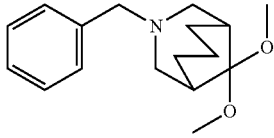 [SMILES: COC1(OC)C2CCCC1CN(Cc1ccccc1)C2]

A mixture of cyclohexanone (1.0 g, 1 eq., 10.2 mmol), N,N-bis(methoxymethyl)-1-phenyl-methanamine (1.98 g, 1 eq., 10.2 mmol) and trimethylsilyl chloride (2.44 g, 2.2 eq., 22.4 mmol) was added dropwise to acetonitrile (70 mL) uponstirring at 40° C. during 3 h. The reaction mixture was additionally stirred for 16 h at room temperature, then quenched and basified to pH 8 with sat. aq. NaHCO$_3$ solution (20 mL) and the crude product extracted with EtOAc (2×50 mL). The organic extract was dried over Na$_2$SO$_4$, filtered and concentrated in vacuo, and the residue obtained was purified by flash chromatography eluting with cyclohexane/EtOAc (9:1) to give the pure title compound as a yellow oil (0.8 g, 34%). UPLC-MS: $t_R$=2.74 min (generic method); MS (ESI) m/z calcd for C$_{15}$H$_{20}$NO (M−C$_2$H$_6$O+H)$^+$: 230.2, found: 230.1.

3-Benzyl-3-azabicyclo[3.3.1]nonan-9-one

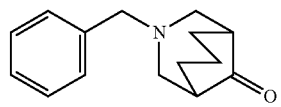 [SMILES: O=C1C2CCCC1CN(Cc1ccccc1)C2]

In a round bottomed flask, to a solution of crude 3-benzyl-9,9-dimethoxy-3-azabicyclo[3.3.1]nonane (ca. 3.0 g) in DCM (20 mL) was slowly added a mixture of trifluoroacetic acid (5.0 mL) and water (5.0 mL). The resulting solution was stirred overnight at room temperature. Upon completion of the reaction, trifluoroacetic acid was evaporated and sat. aq. NaHCO$_3$ solution was added to pH 8. The crude product was extracted with DCM (2×20 mL), and the combined organic phase extracted, dried over Na$_2$SO$_4$, filtered and concentrated in vacuo. The crude product was purified by flash chromatography eluting with cyclohexane/DCM (3:7) to give the pure title compound as a white solid (0.7 g, 28% estimated). UPLC-MS: $t_R$=2.88 min (generic method); MS (ESI) m/z calcd for C$_{15}$H$_{20}$NO (M+H)$^+$: 230.2, found: 230.1. $^1$H NMR (400 MHz, DMSO-d$_6$) 7.40-7.30 (m, 4H), 7.29-7.22 (m, 1H), 3.45 (s, 2H), 3.11 (d, J=11.0 Hz, 2H), 2.88 (dt, J=12.7, 6.3 Hz, 1H), 2.45 (d, J=11.8 Hz, 2H), 2.24 (br s, 2H), 2.14-2.01 (m, 2H), 1.99-1.76 (m, 2H), 1.46 (dt, J=12.6, 6.1 Hz, 1H).

tert-Butyl 9-hydroxy-3-azabicyclo[3.3.1]nonane-3-carboxylate

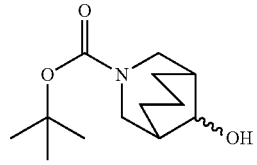 [SMILES: CC(C)(C)OC(=O)N1CC2CCCC(C1)C2O]

Step 1. A solution of 3-benzyl-3-azabicyclo[3.3.1]nonan-9-one (0.6 g, 1.0 eq., 2.6 mmol) in EtOH (30 mL) was initially stirred, followed by subsequent addition of 10% Pd/C (0.5 g) and cyclohexene (7.8 mL, 30 eq., 78 mmol). The reaction mixture was stirred at 80° C. until complete conversion of the starting material. The crude mixture was filtered through a pad of Celite eluting with EtOAc, and, after removal of the solvent under reduced pressure, the crude 3-azabicyclo[3.3.1]nonan-9-one (0.35 g, 95%) was used in the next step without any further purification. UPLC-MS: $t_R$=1.11 min (polar method); MS (ESI) m/z calcd for C$_8$H$_{14}$NO (M+H)$^+$: 140.1, found: 140.1.

Step 2. To a crude solution of 3-azabicyclo[3.3.1]nonan-9-one (0.35 g, 1.0 eq., 2.51 mmol) in dry DCM (5.0 mL) were sequentially added di-tert-butyl dicarbonate (0.656 g, 1.2 eq., 3.01 mmol) and diisopropyl amine (1.31 mL, 3.0 eq., 7.53 mmol). The resulting mixture was stirred at room temperature for 1 h. The reaction was then quenched with water and the organics extracted with DCM (2×20 mL). The organic phase was dried over $Na_2SO_4$ and concentrated in vacuo to furnish a crude product, which was purified by flash chromatography eluting with cyclohexane/EtOAc (8:2) to give the pure tert-butyl 9-oxo-3-azabicyclo[3.3.1]nonane-3-carboxylate as a pale yellow solid (0.3 g, 50% estimated). UPLC-MS: $t_R$=2.23 min (generic method); MS (ESI) m/z calcd for $C_9H_{14}NO_3$ (M-$^t$Bu+2H)$^+$: 184.1, found: 184.1. $^1$H NMR (400 MHz, DMSO-$d_6$) 4.43-4.18 (m, 2H), 3.35-3.10 (m, 2H), 2.27 (br s, 2H), 2.17-2.03 (m, 2H), 1.99-1.82 (m, 3H), 1.49-1.45 (m, 1H), 1.44 (s, 9H).

Step 3. In a round bottomed flask tert-butyl 9-oxo-3-azabicyclo[3.3.1]nonane-3-carboxylate (0.3 g, 1 eq., 1.26 mmol) was dissolved in MeOH (5 mL) and the resulting solution was cooled to 0° C. Sodium borohydride (0.12 g, 2.5 eq., 3.14 mmol) was slowly added and the mixture was stirred at room temperature for 2 h. The reaction mixture was quenched with 1N NaOH (10 mL) solution and extracted with EtOAc (2×30 mL). The organic extracts were dried over $Na_2SO_4$ and concentrated in vacuo to furnish a crude product, which was purified by flash chromatography eluting with cyclohexane/EtOAc (7:3) to give the pure title compound (0.23 g, 76%) as a white solid, as a 8:2 mixture of two stereoisomers.

UPLC-MS: $t_R$=2.02 min (generic method); MS (ESI) m/z calcd for $C_9H_{16}NO_3$ (M-$^t$Bu+2H)$^+$: 186.1, found: 186.1.

General Procedure for Mitsunobu Reaction (GP1)

Under $N_2$ atmosphere, to a 0° C. solution of tert-butyl-hydroxy-azabicyclo carboxylate (1.05 eq.), the appropriate phenol (1 eq.) and PPh$_3$ (1.05 eq.) in dry THF was added dropwise diisopropyl azodicarboxylate (1.05 eq.). The reaction crude was allowed to warm to room temperature and stirred for 16 h. Then, the mixture was quenched with HCl and extracted with EtOAc (2×). The organic extracts were washed with brine, dried over $Na_2SO_4$ and concentrated in vacuo to furnish the crude product, which was purified by flash chromatography.

General Procedure for O-Substitution (GP2)

t-BuOK (1 eq.) was added to a solution of tert-butyl-hydroxy-azabicyclo carboxylate (1 eq.), and the appropriate aryl chloride (1 eq.) in dry THF. The reaction mixture was refluxed for 16 h. Then, the mixture was quenched with water and extracted with DCM (2×). The organic extracts were washed with brine, dried over $Na_2SO_4$ and concentrated in vacuo to furnish the crude product, which was purified by flash chromatography.

General Procedure for Boc-Deprotection (GP3)

The appropriate N-Boc-substituted azabicyclo derivative (1 eq.) was treated at 0° C. with TFA/DCM (1:3). The reaction was stirred at room temperature for 2 h. The crude mixture was concentrated in vacuo, and re-dissolved re-concentrated with DCM (2×). The desired de-Boc product was obtained in quantitative yield and it was used without any further purification.

General Procedure for Sulphonamides Synthesis (GP4)

The appropriate substituted azabicyclo trifluoroacetate (1.1 eq.) was dissolved in THF. Trimethylamine (4 eq.) was then added followed by 3,5-dimethyl-1H-pyrazole-4-sulfonyl chloride (1 eq.). The reaction mixture was stirred at room temperature for 16 h. Then it was quenched by the addition of HCl 2N and extracted with EtOAc (2×). The organic extracts were dried over $Na_2SO_4$ and concentrated in vacuo to furnish the crude product, which was purified by flash chromatography.

tert-Butyl (1R,3s,5S)-3-phenoxy-8-azabicyclo[3.2.1]octane-8-carboxylate

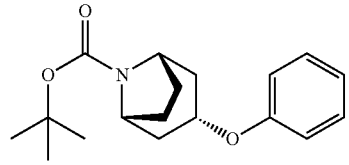

Following GP1, under $N_2$ atmosphere, to a 0° C. solution of tert-butyl (1R,3r,5S)-3-hydroxybicyclo[3.2.1]octane-8-carboxylate (0.15 g, 1 eq., 0.66 mmol), phenol (0.07 g, 1.2 eq., 0.79 mmol), and PPh$_3$ (0.21 mg, 1.5 eq., 0.99 mmol) in dry THF (5 mL) was added dropwise diisopropyl azodicarboxylate (0.2 mL, 1.2 eq., 0.79 mmol). The reaction crude was allowed to warm to room temperature and stirred for 16 h. Then, the mixture was quenched with HCl (10 mL) and extracted with EtOAc (2×5 mL). The organic extracts were washed with brine (10 mL), dried over $Na_2SO_4$ and concentrated in vacuo to furnish the crude product, which was purified by flash chromatography eluting with cyclohexane/EtOAc (0 to 80%) to give the pure title compound as colourless oil (0.07 g, 40%). UPLC-MS (method A): Rt. 1.86 min (TIC); ionization ES$^+$304 [M+H]$^+$. $^1$H NMR (400 MHz, DMSO-$d_6$): δ 7.30-7.23 (m, 2H), 7.01-6.95 (m, 2H), 6.92 (td, J=7.3, 1.1 Hz, 1H), 4.85-4.74 (m, 1H), 4.19-4.10 (m, 2H), 2.15-2.03 (m, 2H), 1.95-1.73 (m, 4H), 1.58-1.46 (m, 2H), 1.42 (s, 9H), 1.40-1.37 (m, 1H).

tert-Butyl (1R,3r,5S)-3-phenoxy-8-azabicyclo[3.2.1]octane-8-carboxylate

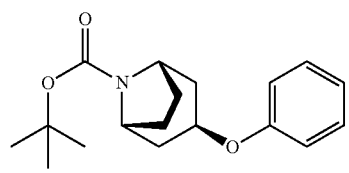

Following GP1, under $N_2$ atmosphere, to a 0° C. solution of tert-butyl (1R,3s,5S)-3-hydroxybicyclo[3.2.1]octane-8-carboxylate (0.3 g, 1.05 eq., 1.32 mmol), phenol (0.12 g, 1 eq., 1.26 mmol), and PPh$_3$ (0.35 g, 1.05 eq., 1.32 mmol) in dry THF (4 mL) was added dropwise diisopropyl azodicarboxylate (0.3 mL, 1.05 eq., 1.32 mmol). The reaction crude was allowed to warm to room temperature and stirred for 16 h. Then, the mixture was quenched with HCl (10 mL) and extracted with EtOAc (2×5 mL). The organic extracts were washed with brine (10 mL), dried over $Na_2SO_4$ and concentrated in vacuo to furnish the crude product, which was purified by flash chromatography eluting with cyclohexane/EtOAc (0 to 100%) to give the pure title compound as colourless oil (0.13 g, 33%). UPLC-MS (method A): Rt. 3.24 min (TIC); ionization ES$^+$304 [M+H]$^+$. $^1$H NMR (400 MHz, DMSO-$d_6$): δ 7.33-7.24 (m, 2H), 6.96-6.85 (m, 3H), 4.72 (t, J=4.9 Hz, 1H), 4.12-3.98 (m, 2H), 2.13-1.95 (m, 4H), 1.94-1.79 (m, 4H), 1.42 (s, 9H), 1.40-1.38 (m, 1H).

tert-Butyl (1R,3s,5S)-3-(3-methylphenoxy)-8-azabicyclo[3.2.1]octane-8-carboxylate

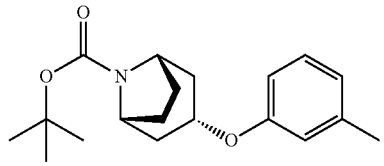

Following GP1, under N₂ atmosphere, to a 0° C. solution of tert-butyl (1R,3r,5S)-3-hydroxybicyclo[3.2.1]octane-8-carboxylate (0.18 g, 1.05 eq., 0.77 mmol), 3-methylphenol (0.08 mL, 1 eq., 0.73 mmol), and PPh₃ (0.2 g, 1.05 eq., 0.77 mmol) in dry THF (4 mL) was added dropwise diisopropyl azodicarboxylate (0.15 mL, 1.05 eq., 0.77 mmol). The reaction crude was allowed to warm to room temperature and stirred for 16 h. Then, the mixture was quenched with HCl (10 mL) and extracted with EtOAc (2×5 mL). The organic extracts were washed with brine (10 mL), dried over Na₂SO₄ and concentrated in vacuo to furnish the crude product, which was purified by flash chromatography eluting with cyclohexane/EtOAc (0 to 100%) to give the pure title compound as colourless oil (0.16 g, 76%). ¹H NMR (400 MHz, DMSO-d₆): δ 7.13 (td, J=7.4, 1.3 Hz, 1H), 6.78 (s, 1H), 6.77-6.70 (m, 2H), 4.76 (tt, J=10.9, 5.8 Hz, 1H), 4.16-4.07 (m, 2H), 2.26 (s, 3H), 2.14-2.00 (m, 2H), 1.96-1.69 (m, 4H), 1.57-1.46 (m, 2H), 1.41 (s, 9H).

tert-Butyl (1R,3r,5S)-3-(3-methylphenoxy)-8-azabicyclo[3.2.1]octane-8-carboxylate

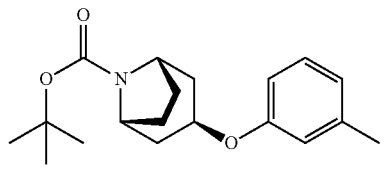

Following GP1, under N₂ atmosphere, to a 0° C. solution of tert-butyl (1R,3s,5S)-3-hydroxybicyclo[3.2.1]octane-8-carboxylate (0.18 g, 1.05 eq., 0.77 mmol), 3-methylphenol (0.08 mL, 1 eq., 0.73 mmol), and PPh₃ (0.2 g, 1.05 eq., 0.77 mmol) in dry THF (4 mL) was added dropwise diisopropyl azodicarboxylate (0.15 mL, 1.05 eq., 0.77 mmol). The reaction crude was allowed to warm to room temperature and stirred for 16 h. Then, the mixture was quenched with HCl (10 mL) and extracted with EtOAc (2×5 mL). The organic extracts were washed with brine (10 mL), dried over Na₂SO₄ and concentrated in vacuo to furnish the crude product, which was purified by flash chromatography eluting with cyclohexane/EtOAc (0 to 100%) to give the pure title compound as colourless oil (0.18 g, 85%). ¹H NMR (400 MHz, DMSO-d₆): δ 7.16 (t, J=7.8 Hz, 1H), 6.77-6.70 (m, 2H), 6.67 (dd, J=8.1, 2.5 Hz, 1H), 4.69 (t, J=4.9 Hz, 1H), 4.09-4.04 (m, 2H), 2.27 (s, 3H), 2.08-1.97 (m, 4H), 1.83 (d, J=17.4 Hz, 4H), 1.42 (s, 9H).

tert-Butyl (1R,3r,5S)-3-(4-ethylphenoxy)-8-azabicyclo[3.2.1]octane-8-carboxylate

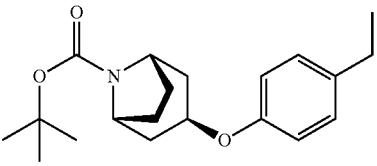

Following GP1, under N₂ atmosphere, to a 0° C. solution of tert-butyl (1R,3s,5S)-3-hydroxybicyclo[3.2.1]octane-8-carboxylate (0.18 g, 1.05 eq., 0.77 mmol), 3-ethylphenol (0.09 g, 1 eq., 0.73 mmol), and PPh₃ (0.2 g, 1.05 eq., 0.77 mmol) in dry THF (4 mL) was added dropwise diisopropyl azodicarboxylate (0.15 mL, 1.05 eq., 0.77 mmol). The reaction crude was allowed to warm to room temperature and stirred for 16 h. Then, the mixture was quenched with HCl (10 mL) and extracted with EtOAc (2×5 mL). The organic extracts were washed with brine (10 mL), dried over Na₂SO₄ and concentrated in vacuo to furnish the crude product, which was purified by flash chromatography eluting with cyclohexane/EtOAc (0 to 100%) to give the pure title compound as colourless oil (0.12 g, 50%). UPLC-MS (method A): Rt. 2.72 min (TIC); ionization ES+332 [M+H]⁺. ¹H NMR (400 MHz, DMSO-d₆): δ 7.15-7.08 (m, 2H), 6.84-6.77 (m, 2H), 4.67 (t, J=4.8 Hz, 1H), 4.09-4.03 (m, 2H), 2.58-2.51 (m, 2H), 2.10-1.94 (m, 4H), 1.92-1.80 (m, 4H), 1.42 (s, 9H), 1.15 (t, J=7.6 Hz, 3H).

tert-Butyl (1R,3r,5S)-3-(4-butylphenoxy)-8-azabicyclo[3.2.1]octane-8-carboxylate

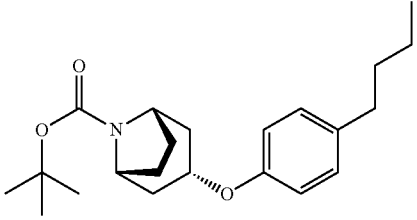

Following GP1, under N₂ atmosphere, to a 0° C. solution of tert-butyl (1R,3r,5S)-3-hydroxybicyclo[3.2.1]octane-8-carboxylate (0.18 g, 1.05 eq., 0.77 mmol), 4-butylphenol (0.11 mL, 1 eq., 0.73 mmol), and PPh₃ (0.2 g, 1.05 eq., 0.77 mmol) in dry THF (4 mL) was added dropwise diisopropyl azodicarboxylate (0.15 mL, 1.05 eq., 0.77 mmol). The reaction crude was allowed to warm to room temperature and stirred for 16 h. Then, the mixture was quenched with HCl (10 mL) and extracted with EtOAc (2×5 mL). The organic extracts were washed with brine (10 mL), dried over Na₂SO₄ and concentrated in vacuo to furnish the crude product, which was purified by flash chromatography eluting with cyclohexane/EtOAc (0 to 100%) to give the pure title compound as colourless oil (0.15 g, 57%). ¹H NMR (400 MHz, DMSO-d₆): δ 7.10-7.03 (m, 2H), 6.91-6.84 (m, 2H), 4.77-4.67 (m, 1H), 4.18-4.02 (m, 2H), 2.51-2.46 (m, 2H), 2.13-1.98 (m, 2H), 1.95-1.70 (m, 4H), 1.60-1.44 (m, 4H), 1.42 (s, 9H), 1.28 (h, J=7.3 Hz, 2H), 0.88 (td, J=7.3, 1.9 Hz, 3H).

tert-Butyl (1R,3r,5S)-3-(4-Butylphenoxy)-8-azabicyclo[3.2.1]octane-8-carboxylate

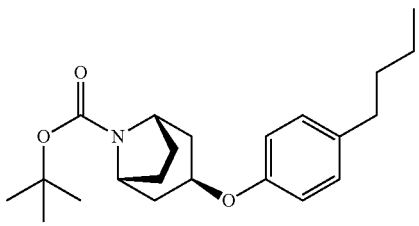

Following GP1, under $N_2$ atmosphere, to a 0° C. solution of tert-butyl (1R,3s,5S)-3-hydroxybicyclo[3.2.1]octane-8-carboxylate (0.18 g, 1.05 eq., 0.77 mmol), 4-butylphenol (0.11 mL, 1 eq., 0.73 mmol), and $PPh_3$ (0.2 g, 1.05 eq., 0.77 mmol) in dry THF (4 mL) was added dropwise diisopropyl azodicarboxylate (0.15 mL, 1.05 eq., 0.77 mmol). The reaction crude was allowed to warm to room temperature and stirred for 16 h. Then, the mixture was quenched with HCl (10 mL) and extracted with EtOAc (2×5 mL). The organic extracts were washed with brine (10 mL), dried over $Na_2SO_4$ and concentrated in vacuo to furnish the crude product, which was purified by flash chromatography eluting with cyclohexane/EtOAc (0 to 100%) to give the pure title compound as colourless oil (0.21 g, 78%). $^1H$ NMR (400 MHz, DMSO-$d_6$): δ 7.13-7.06 (m, 2H), 6.82-6.76 (m, 2H), 4.66 (t, J=4.9 Hz, 1H), 4.10-4.04 (m, 2H), 2.08-1.96 (m, 4H), 1.92-1.77 (m, 4H), 1.51 (tt, J=7.9, 6.4 Hz, 2H), 1.42 (s, 9H), 1.34-1.23 (m, 3H), 1.18 (t, J=7.1 Hz, 1H), 0.89 (td, J=7.3, 3.2 Hz, 3H).

tert-Butyl (1R,3r,5S)-3-(4-hexylphenoxy)-8-azabicyclo[3.2.1]octane-8-carboxylate

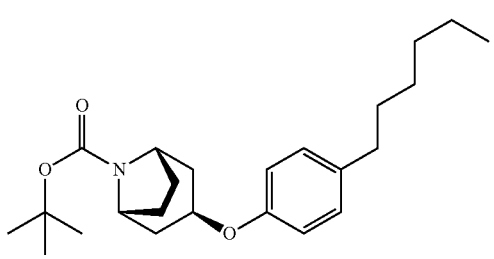

Following GP1, under $N_2$ atmosphere, to a 0° C. solution of tert-butyl (1R,3s,5S)-3-hydroxybicyclo[3.2.1]octane-8-carboxylate (0.18 g, 1.05 eq., 0.77 mmol), 4-hexylphenol (0.13 g, 1 eq., 0.73 mmol), and $PPh_3$ (0.2 g, 1.05 eq., 0.77 mmol) in dry THF (4 mL) was added dropwise diisopropyl azodicarboxylate (0.15 mL, 1.05 eq., 0.77 mmol). The reaction crude was allowed to warm to room temperature and stirred for 16 h. Then, the mixture was quenched with HCl (10 mL) and extracted with EtOAc (2×5 mL). The organic extracts were washed with brine (10 mL), dried over $Na_2SO_4$ and concentrated in vacuo to furnish the crude product, which was purified by flash chromatography eluting with cyclohexane/EtOAc (0 to 80%) to give the pure title compound as colourless oil (0.19 g, 67%). UPLC-MS (method A): Rt. 3.06 min (TIC); ionization $ES^+388$ [M+H]$^+$. $^1H$ NMR (400 MHz, DMSO-$d_6$): δ 7.12-7.05 (m, 2H), 6.87-6.74 (m, 2H), 4.66 (t, J=4.8 Hz, 1H), 4.09-4.02 (m, 2H), 2.50-2.46 (m, 2H), 2.02 (d, J=18.3 Hz, 4H), 1.84 (d, J=17.2 Hz, 4H), 1.59-1.47 (m, 2H), 1.42 (d, J=4.6 Hz, 9H), 1.32-1.21 (m, 6H), 0.90-0.82 (m, 3H).

tert-Butyl (1R,3r,5S)-3-(4-isopropylphenoxy)-8-azabicyclo[3.2.1]octane-8-carboxylate

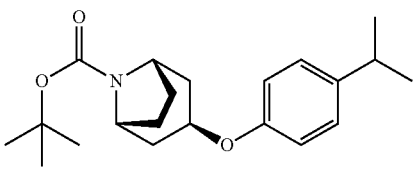

Following GP1, under $N_2$ atmosphere, to a 0° C. solution of tert-butyl (1R,3s,5S)-3-hydroxybicyclo[3.2.1]octane-8-carboxylate (0.18 g, 1.05 eq., 0.77 mmol), 4-isopropylphenol (0.1 g, 1 eq., 0.73 mmol), and $PPh_3$ (0.2 g, 1.05 eq., 0.77 mmol) in dry THF (4 mL) was added dropwise diisopropyl azodicarboxylate (0.15 mL, 1.05 eq., 0.77 mmol). The reaction crude was allowed to warm to room temperature and stirred for 16 h. Then, the mixture was quenched with HCl (10 mL) and extracted with EtOAc (2×5 mL). The organic extracts were washed with brine (10 mL), dried over $Na_2SO_4$ and concentrated in vacuo to furnish the crude product, which was purified by flash chromatography eluting with cyclohexane/EtOAc (0 to 100%) to give the pure title compound as colourless oil (0.14 g, 57%). UPLC-MS (method A): Rt. 2.93 min (TIC); ionization $ES^+346$ [M+H]$^+$. $^1H$ NMR (400 MHz, DMSO-$d_6$): δ 7.18-7.11 (m, 2H), 6.83-6.77 (m, 2H), 4.67 (t, J=4.8 Hz, 1H), 4.10-4.01 (m, 2H), 2.89-2.76 (m, 1H), 2.10-1.94 (m, 4H), 1.93-1.79 (m, 4H), 1.42 (s, 9H), 1.18 (d, J=6.9 Hz, 6H).

tert-Butyl (1R,3r,5S)-3-(4-methoxyphenoxy)-8-azabicyclo[3.2.1]octane-8-carboxylate

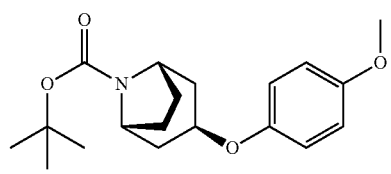

Following GP1, under $N_2$ atmosphere, to a 0° C. solution of tert-butyl (1R,3s,5S)-3-hydroxybicyclo[3.2.1]octane-8-carboxylate (0.18 g, 1.05 eq., 0.77 mmol), 4-methoxyphenol (0.09 g, 1 eq., 0.73 mmol), and $PPh_3$ (0.2 g, 1.05 eq., 0.77 mmol) in dry THF (4 mL) was added dropwise diisopropyl azodicarboxylate (0.15 mL, 1.05 eq., 0.77 mmol). The reaction crude was allowed to warm to room temperature and stirred for 16 h. Then, the mixture was quenched with HCl (10 mL) and extracted with EtOAc (2×5 mL). The organic extracts were washed with brine (10 mL), dried over $Na_2SO_4$ and concentrated in vacuo to furnish the crude product, which was purified by flash chromatography eluting with cyclohexane/EtOAc (0 to 100%) to give the pure title compound as colourless oil (0.09 g, 37%). UPLC-MS (method A): Rt. 1.92 min (TIC); ionization $ES^+334$ [M+H]$^+$. $^1H$ NMR (400 MHz, DMSO-$d_6$): δ 6.90-6.78 (m, 4H), 4.60

(t, J=4.8 Hz, 1H), 4.10-4.00 (m, 2H), 3.70 (s, 3H), 2.15-1.94 (m, 4H), 1.92-1.77 (m, 4H), 1.41 (d, J=4.0 Hz, 9H).

tert-Butyl (1R,3r,5S)-3-(4-propoxyphenoxy)-8-azabicyclo[3.2.1]octane-8-carboxylate

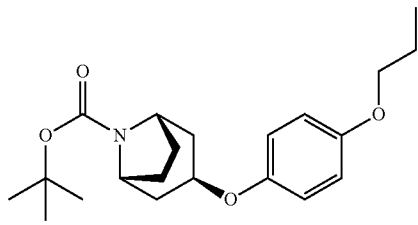

Following GP1, under N$_2$ atmosphere, to a 0° C. solution of tert-butyl (1R,3s,5S)-3-hydroxybicyclo[3.2.1]octane-8-carboxylate (0.18 g, 1.05 eq., 0.77 mmol), 4-propoxyphenol (0.11 g, 1 eq., 0.73 mmol), and PPh$_3$ (0.2 g, 1.05 eq., 0.77 mmol) in dry THF (4 mL) was added dropwise diisopropyl azodicarboxylate (0.15 mL, 1.05 eq., 0.77 mmol). The reaction crude was allowed to warm to room temperature and stirred for 16 h. Then, the mixture was quenched with HCl (10 mL) and extracted with EtOAc (2×5 mL). The organic extracts were washed with brine (10 mL), dried over Na$_2$SO$_4$ and concentrated in vacuo to furnish the crude product, which was purified by flash chromatography eluting with cyclohexane/EtOAc (0 to 100%) to give the pure title compound as colourless oil (0.13 g, 50%). UPLC-MS (method A): Rt. 2.66 min (TIC); ionization ES$^+$362 [M+H]$^+$.

tert-Butyl (1R,3s,5S)-3-(4-cyanophenoxy)-8-azabicyclo[3.2.1]octane-8-carboxylate

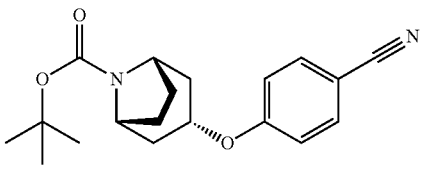

Following GP1, under N$_2$ atmosphere, to a 0° C. solution of tert-butyl (1R,3r,5S)-3-hydroxybicyclo[3.2.1]octane-8-carboxylate (0.18 g, 1.05 eq., 0.77 mmol), 4-cyanophenol (0.09 g, 1 eq., 0.73 mmol), and PPh$_3$ (0.2 g, 1.05 eq., 0.77 mmol) in dry THF (4 mL) was added dropwise diisopropyl azodicarboxylate (0.15 mL, 1.05 eq., 0.77 mmol). The reaction crude was allowed to warm to room temperature and stirred for 16 h. Then, the mixture was quenched with HCl (10 mL) and extracted with EtOAc (2×5 mL). The organic extracts were washed with brine (10 mL), dried over Na$_2$SO$_4$ and concentrated in vacuo to furnish the crude product, which was purified by flash chromatography eluting with cyclohexane/EtOAc (0 to 100%) to give the pure title compound as colourless oil (0.13 g, 56%). UPLC-MS (method A): Rt. 1.61 min (TIC); ionization ES$^+$329 [M+H]$^+$. $^1$H NMR (400 MHz, DMSO-d$_6$): δ 7.72 (dd, J=9.3, 2.5 Hz, 2H), 7.63 (dd, J=9.1, 2.3 Hz, 2H), 5.00-4.87 (m, 1H), 4.18-4.09 (m, 2H), 2.10 (s, 2H), 1.84 (t, J=10.1 Hz, 4H), 1.54 (d, J=17.5 Hz, 2H), 1.41 (s, 9H).

tert-Butyl (1R,3r,5S)-3-(4-cyanophenoxy)-8-azabicyclo[3.2.1]octane-8-carboxylate

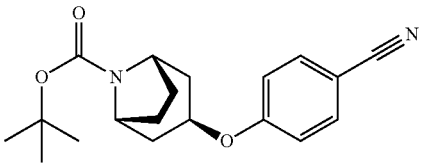

Following GP1, under N$_2$ atmosphere, to a 0° C. solution of tert-butyl (1R,3s,5S)-3-hydroxybicyclo[3.2.1]octane-8-carboxylate (0.18 g, 1.05 eq., 0.77 mmol), 4-cyanophenol (0.09 g, 1 eq., 0.73 mmol), and PPh$_3$ (0.2 g, 1.05 eq., 0.77 mmol) in dry THF (4 mL) was added dropwise diisopropyl azodicarboxylate (0.15 mL, 1.05 eq., 0.77 mmol). The reaction crude was allowed to warm to room temperature and stirred for 16 h. Then, the mixture was quenched with HCl (10 mL) and extracted with EtOAc (2×5 mL). The organic extracts were washed with brine (10 mL), dried over Na$_2$SO$_4$ and concentrated in vacuo to furnish the crude product, which was purified by flash chromatography eluting with cyclohexane/EtOAc (0 to 100%) to give the pure title compound as colourless oil (0.19 g, 77%). UPLC-MS (method A): Rt. 1.66 min (TIC); ionization ES$^+$329 [M+H]$^+$. $^1$H NMR (400 MHz, DMSO-d$_6$): δ 7.80-7.66 (m, 2H), 7.29-7.01 (m, 2H), 4.83 (t, J=4.8 Hz, 1H), 4.10-4.00 (m, 2H), 2.04-1.75 (m, 8H), 1.40 (d, J=7.0 Hz, 9H).

tert-Butyl (1R,3r,5S)-3-(2-fluoro-4-methylphenoxy)-8-azabicyclo[3.2.1]octane-8-carboxylate

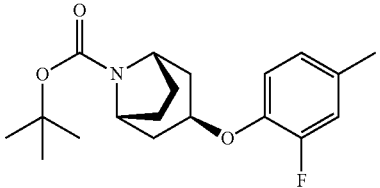

Following GP1, under N$_2$ atmosphere, to a 0° C. solution of tert-butyl (1R,3s,5S)-3-hydroxybicyclo[3.2.1]octane-8-carboxylate (0.18 g, 1.05 eq., 0.77 mmol), 2-fluoro-4-methylphenol (0.09 g, 1 eq., 0.73 mmol), and PPh$_3$ (0.2 g, 1.05 eq., 0.77 mmol) in dry THF (4 mL) was added dropwise diisopropyl azodicarboxylate (0.15 mL, 1.05 eq., 0.77 mmol). The reaction crude was allowed to warm to room temperature and stirred for 16 h. Then, the mixture was quenched with HCl (10 mL) and extracted with EtOAc (2×5 mL). The organic extracts were washed with brine (10 mL), dried over Na$_2$SO$_4$ and concentrated in vacuo to furnish the crude product, which was purified by flash chromatography eluting with cyclohexane/EtOAc (0 to 100%) to give the pure title compound as colourless oil (0.18 g, 74%). UPLC-MS (method A): Rt. 2.32 min (TIC); ionization ES$^+$336 [M+H]$^+$. $^1$H NMR (400 MHz, DMSO-d$_6$): δ 7.05 (dd, J=12.5, 2.0 Hz, 1H), 6.98 (t, J=8.6 Hz, 1H), 6.91 (dt, J=8.5, 1.3 Hz, 1H), 4.70 (t, J=4.8 Hz, 1H), 4.14-4.00 (m, 2H), 2.24 (s, 3H), 2.14-1.93 (m, 4H), 1.92-1.79 (m, 4H), 1.42 (s, 9H).

tert-Butyl (1R,3r,5S)-3-(4-formylphenoxy)-8-azabicyclo[3.2.1]octane-8-carboxylate

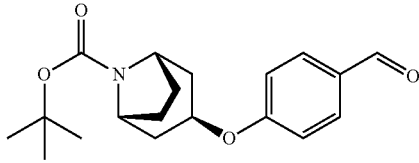

Following GP1, under N₂ atmosphere, to a 0° C. solution of tert-butyl (1R,3s,5S)-3-hydroxybicyclo[3.2.1]octane-8-carboxylate (0.18 g, 1.05 eq., 0.77 mmol), 4-hydroxybenzaldehyde (0.089 g, 1 eq., 0.73 mmol), and PPh$_3$ (0.2 g, 1.05 eq., 0.77 mmol) in dry THF (4 mL) was added dropwise diisopropyl azodicarboxylate (0.15 mL, 1.05 eq., 0.77 mmol). The reaction crude was allowed to warm to room temperature and stirred for 16 h. Then, the mixture was quenched with HCl (10 mL) and extracted with EtOAc (2×5 mL). The organic extracts were washed with brine (10 mL), dried over Na$_2$SO$_4$ and concentrated in vacuo to furnish the crude product, which was purified by flash chromatography eluting with cyclohexane/EtOAc (80:20) to give the pure title compound as a white solid (0.36 g, 55%). UPLC-MS: tR=2.89 min (generic method); MS (ESI) m/z calcd for C$_{15}$H$_{18}$NO$_4$ (M−tBu+2H)$^+$: 276.1, found: 276.2. $^1$H NMR (400 MHz, DMSO-d$_6$) δ 9.86 (s, 1H), 7.86 (d, J=8.7 Hz, 2H), 7.08 (d, J=8.7 Hz, 2H), 4.88 (app-t, J=4.8 Hz, 1H), 4.07 (br s, 2H), 2.23-1.72 (m, 8H), 1.42 (s, 9H).

tert-Butyl (1R,3r,5S)-3-(4-(trifluoromethyl)phenoxy)-8-azabicyclo[3.2.1]octane-8-carboxylate

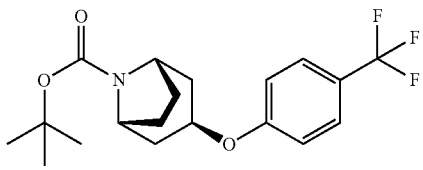

Following GP1, under N₂ atmosphere, to a 0° C. solution of tert-butyl (1R,3s,5S)-3-hydroxybicyclo[3.2.1]octane-8-carboxylate (0.18 g, 1.05 eq., 0.77 mmol), 4-(trifluoromethyl)phenol (0.118 g, 1 eq., 0.73 mmol), and PPh$_3$ (0.2 g, 1.05 eq., 0.77 mmol) in dry THF (4 mL) was added dropwise diisopropyl azodicarboxylate (0.15 mL, 1.05 eq., 0.77 mmol). The reaction crude was allowed to warm to room temperature and stirred for 16 h. Then, the mixture was quenched with HCl (10 mL) and extracted with EtOAc (2×5 mL). The organic extracts were washed with brine (10 mL), dried over Na$_2$SO$_4$ and concentrated in vacuo to furnish the crude product, which was purified by flash chromatography eluting with cyclohexane/EtOAc (90:10) to give the pure title compound as a white solid (0.21 g, 64%). UPLC-MS: tR=2.53 min (apolar method); MS (ESI) m/z calcd for C$_{15}$H$_{17}$F$_3$NO$_3$ (M−$^t$Bu+2H)$^+$: 316.1, found: 316.2. $^1$H NMR (400 MHz, DMSO-d$_6$) δ 7.64 (d, J=8.6 Hz, 2H), 7.07 (d, J=8.6 Hz, 2H), 4.83 (app-t, J=4.9 Hz, 1H), 4.07 (br s, 2H), 2.14-1.70 (m, 8H), 1.42 (s, 9H).

tert-Butyl (1R,3r,5S)-3-[4-[(E/Z)-3-methylbut-1-enyl]phenoxy]-8-azabicyclo[3.2.1]octane-8-carboxylate

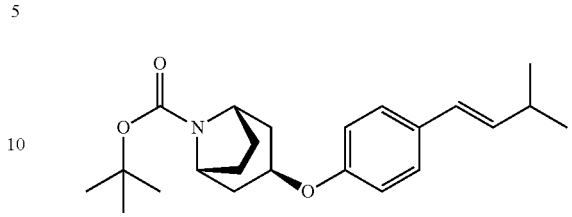

Following GP1, under N₂ atmosphere, to a 0° C. solution of tert-butyl (1R,3s,5S)-3-hydroxybicyclo[3.2.1]octane-8-carboxylate (0.105 g, 1.05 eq., 0.45 mmol), 4-[(E)-3-methylbut-1-enyl]phenol (0.072 g, 1 eq., 0.44 mmol), and PPh$_3$ (0.118 g, 1.05 eq., 0.45 mmol) in dry THF (4 mL) was added dropwise diisopropyl azodicarboxylate (0.089 mL, 1.05 eq., 0.45 mmol). The reaction crude was allowed to warm to room temperature and stirred for 16 h. Then, the mixture was quenched with HCl (10 mL) and extracted with EtOAc (2×5 mL). The organic extracts were washed with brine (10 mL), dried over Na$_2$SO$_4$ and concentrated in vacuo to furnish the crude product, which was purified by flash chromatography eluting with cyclohexane/EtOAc (90:10) to give the pure title compound as a pale-yellow oil (0.90 g, 55%), as a mixture of cis/trans isomers. UPLC-MS: t$_R$=3.22 min (apolar method); MS (ESI) m/z calcd for C$_{19}$H$_{26}$NO$_3$ (M−$^t$Bu+2H)$^+$: 316.2, found: 316.2. $^1$H NMR (400 MHz, DMSO-d$_6$) δ 7.19 (d, J=8.6 Hz, 2H), 6.87 (d, J=8.6 Hz, 2H), 6.20 (d, J=11.6 Hz, 1H), 5.36 (dd, J=11.6, 10.1 Hz, 1H), 4.71 (app-t, J=4.9 Hz, 1H), 4.06 (br s, 2H), 2.98-2.69 (m, 1H), 2.24-1.66 (m, 8H), 1.41 (s, 9H), 1.01 (d, J=6.6 Hz, 6H).

tert-Butyl (1R,3r,5S)-3-[4-chloro-phenoxy]-8-azabicyclo[3.2.1]octane-8-carboxylate

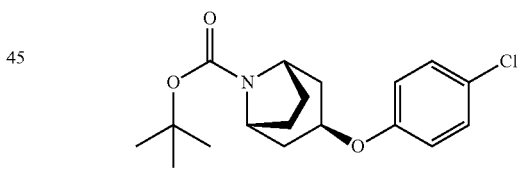

Following GP1, under N₂ atmosphere, to a 0° C. solution of tert-butyl (1R,3s,5S)-3-hydroxybicyclo[3.2.1]octane-8-carboxylate (0.251 g, 1.05 eq., 1.11 mmol), 4-chloro-phenol (0.135 g, 1 eq., 1.06 mmol), and PPh$_3$ (0.290 g, 1.05 eq., 1.11 mmol) in dry THF (6 mL) was added dropwise diisopropyl azodicarboxylate (0.22 mL, 1.05 eq., 1.11 mmol). The reaction crude was allowed to warm to room temperature and stirred for 16 h. Then, the mixture was quenched with HCl (10 mL) and extracted with EtOAc (2×5 mL). The organic extracts were washed with brine (10 mL), dried over Na$_2$SO$_4$ and concentrated in vacuo to furnish the crude product, which was purified by flash chromatography eluting with cyclohexane/EtOAc (90:10) to give the pure title compound as a white solid (0.29 g, 81%). UPLC-MS: t$_R$=2.45 min (apolar method); MS (ESI) m/z calcd for C$_{14}$H$_{17}$ClNO$_3$ (M−$^t$Bu+2H)$^+$: 282.1, found: 282.1.

tert-Butyl (1R,3r,5S)-3-[4-fluoro-phenoxy]-8-azabicyclo[3.2.1]octane-8-carboxylate

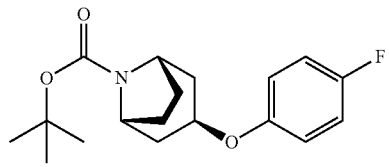

Following GP1, under $N_2$ atmosphere, to a 0° C. solution of tert-butyl (1R,3s,5S)-3-hydroxybicyclo[3.2.1]octane-8-carboxylate (0.251 g, 1.05 eq., 1.11 mmol), 4-fluoro-phenol (0.118 g, 1 eq., 1.06 mmol), and $PPh_3$ (0.290 g, 1.05 eq., 1.11 mmol) in dry THF (6 mL) was added dropwise diisopropyl azodicarboxylate (0.22 mL, 1.05 eq., 1.11 mmol). The reaction crude was allowed to warm to room temperature and stirred for 16 h. Then, the mixture was quenched with HCl (10 mL) and extracted with EtOAc (2×5 mL). The organic extracts were washed with brine (10 mL), dried over $Na_2SO_4$ and concentrated in vacuo to furnish the crude product, which was purified by flash chromatography eluting with cyclohexane/EtOAc (90:10) to give the pure title compound as a white solid (0.174 g, 62%). UPLC-MS: $t_R$=1.98 min (apolar method); MS (ESI) m/z calcd for $C_{14}H_{17}FNO_3$ (M−$^t$Bu+2H)$^+$: 266.1, found: 266.1.

tert-Butyl (1R,s5S)-3-(pyrazin-2-yloxy)-9-azabicyclo[3.3.1]nonane-9-carboxylate

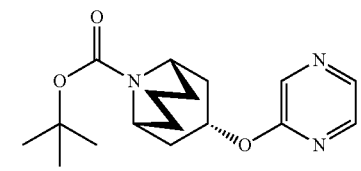

Following GP1, under $N_2$ atmosphere, to a 0° C. solution of tert-butyl (1R,3r,5S)-3-hydroxy-9-azabicyclo[3.3.1]nonane-9-carboxylate (0.18 g, 1.05 eq., 0.73 mmol), pyrazine-2-ol (0.07 g, 1 eq., 0.70 mmol), and $PPh_3$ (0.19 g, 1.05 eq., 0.73 mmol) in dry THF (4 mL) was added dropwise diisopropyl azodicarboxylate (0.14 mL, 1.05 eq., 0.73 mmol). The reaction crude was allowed to warm to room temperature and stirred for 16 h. Then, the mixture was quenched with HCl (10 mL) and extracted with EtOAc (2×5 mL). The organic extracts were washed with brine (10 mL), dried over $Na_2SO_4$ and concentrated in vacuo to furnish the crude product, which was purified by flash chromatography eluting with cyclohexane/EtOAc (0 to 60%) to give the pure title compound as colourless oil (0.06 g, 24%). UPLC-MS (method A): Rt. 1.33 min (TIC); ionization ES$^+$320 [M+H]$^+$.

tert-Butyl (1R,s5S)-7-pyrazin-2-yloxy3-oxa-9-azabicyclo[3.3.1]nonane-9-carboxylate

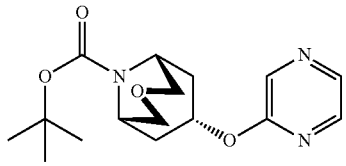

Following GP1, under $N_2$ atmosphere, to a 0° C. solution of tert-butyl (1R,3r,5S)-7-hydroxy-3-oxa-9-azabicyclo[3.3.1]nonane-9-carboxylate (0.18 g, 1.05 eq., 0.72 mmol), pyrazine-2-ol (0.07 g, 1 eq., 0.69 mmol), and $PPh_3$ (0.19 g, 1.05 eq., 0.72 mmol) in dry THF (4 mL) was added dropwise diisopropyl azodicarboxylate (0.14 mL, 1.05 eq., 0.72 mmol). The reaction crude was allowed to warm to room temperature and stirred for 16 h. Then, the mixture was quenched with HCl (10 mL) and extracted with EtOAc (2×5 mL). The organic extracts were washed with brine (10 mL), dried over $Na_2SO_4$ and concentrated in vacuo to furnish the crude product, which was purified by flash chromatography eluting with cyclohexane/EtOAc (0 to 80%) to give the pure title compound as colourless oil (0.14 g, 61%). UPLC-MS (method A): Rt. 0.91 min (TIC); ionization ES$^+$322 [M+H]$^+$. $^1$H NMR (400 MHz, DMSO-d$_6$): δ 8.23 (d, J=1.3 Hz, 1H), 8.22-8.20 (m, 1H), 8.18 (d, J=2.8 Hz, 1H), 6.27-5.89 (m, 1H), 4.05 (d, J=10.8 Hz, 2H), 3.84 (t, J=10.5 Hz, 2H), 3.57 (dt, J=11.5, 2.3 Hz, 2H), 2.36-2.19 (m, 2H), 1.72-1.58 (m, 2H), 1.44 (s, 9H).

tert-Butyl (1R,3r,5S)-3-(2-pyridyloxy)-8-azabicyclo[3.2.1]octane-8-carboxylate

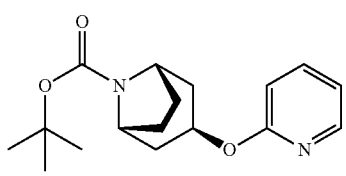

Following GP2, t-BuOK (0.1 g, 1 eq., 0.88 mmol) was added to a solution of tert-butyl (1R,3r,5S)-3-hydroxy-8-azabicyclo[3.2.1]octane-8-carboxylate (0.2 g, 1 eq., 0.88 mmol), and 2-chloropyridine (0.08 mL, 1 eq., 0.88 mmol) in dry THF (7 mL). The reaction mixture was refluxed for 16 h. Then, the mixture was quenched with water (15 mL) and extracted with DCM (2×10 mL). The organic extracts were washed with brine (15 mL), dried over $Na_2SO_4$ and concentrated in vacuo to furnish the crude product, which was purified by flash chromatography eluting with cyclohexane/EtOAc (0 to 60%) to give the pure title compound as colourless oil (0.04 g, 14%). UPLC-MS (method A): Rt. 1.57 min (TIC); ionization ES+305 [M+H]+. $^1$H NMR (400 MHz, DMSO-d$_6$): δ 8.15 (ddd, J=5.0, 2.1, 0.8 Hz, 1H), 7.71 (ddd, J=8.3, 7.1, 2.0 Hz, 1H), 6.95 (ddd, J=7.1, 5.0, 0.9 Hz, 1H), 6.79 (dt, J=8.3, 0.9 Hz, 1H), 5.31 (t, J=5.0 Hz, 1H), 4.15-4.03 (m, 2H), 2.13-1.98 (m, 4H), 1.93-1.77 (m, 4H), 1.42 (s, 9H).

tert-Butyl (1R,3r,5S)-3-[(5-methyl-2-pyridyl)oxy]-8-azabicyclo[3.2.1]octane-8-carboxylate

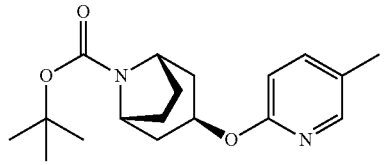

Following GP2, t-BuOK (0.1 g, 1 eq., 0.88 mmol) was added to a solution of tert-butyl (1R,3r,5S)-3-hydroxy-8-azabicyclo[3.2.1]octane-8-carboxylate (0.2 g, 1 eq., 0.88 mmol), and 2-chloro-5-methylpyridine (0.1 mL, 1 eq., 0.88 mmol) in dry THF (7 mL). The reaction mixture was refluxed for 16 h. Then, the mixture was quenched with water (15 mL) and extracted with DCM (2×10 mL). The organic extracts were washed with brine (15 mL), dried over $Na_2SO_4$ and concentrated in vacuo to furnish the crude product, which was purified by flash chromatography eluting with cyclohexane/EtOAc (0 to 60%) to give the pure title compound as colourless oil (0.02 g, 7%). UPLC-MS (method A): Rt. 3.15 min (TIC); ionization $ES^+$ 319 $[M+H]^+$. $^1$H NMR (400 MHz, DMSO-$d_6$): δ 7.99-7.90 (m, 1H), 7.54 (dd, J=8.4, 2.5 Hz, 1H), 6.70 (d, J=8.4 Hz, 1H), 5.25 (t, J=5.0 Hz, 1H), 4.17-3.97 (m, 2H), 2.20 (s, 3H), 2.11-1.98 (m, 4H), 1.93-1.76 (m, 4H), 1.42 (s, 9H).

tert-Butyl (1R,3r,5S)-3-pyrazin-2-yloxy-8-azabicyclo[3.2.1]octane-8-carboxylate

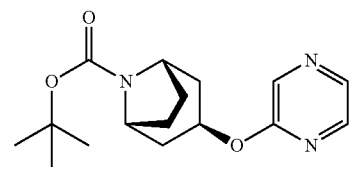

Following GP2, t-BuOK (0.1 g, 1 eq., 0.88 mmol) was added to a solution of tert-butyl (1R,3r,5S)-3-hydroxy-8-azabicyclo[3.2.1]octane-8-carboxylate (0.2 g, 1 eq., 0.88 mmol), and 2-chloropyrazine (0.08 mL, 1 eq., 0.88 mmol) in dry THF (7 mL). The reaction mixture was refluxed for 16 h. Then, the mixture was quenched with water (15 mL) and extracted with DCM (2×10 mL). The organic extracts were washed with brine (15 mL), dried over $Na_2SO_4$ and concentrated in vacuo to furnish the crude product, which was purified by flash chromatography eluting with cyclohexane/EtOAc (0 to 50%) to give the pure title compound as colourless oil (0.1 g, 39%). UPLC-MS (method A): Rt. 1.16 min (TIC); ionization $ES^+$ 306 $[M+H]^+$. $^1$H NMR (400 MHz, DMSO-$d_6$): δ 8.26 (d, J=1.0 Hz, 1H), 8.19-8.15 (m, 2H), 5.29 (t, J=5.0 Hz, 1H), 4.12-4.03 (m, 2H), 2.14-2.00 (m, 4H), 1.86 (t, J=14.9 Hz, 4H), 1.39 (s, 9H).

tert-Butyl (1R,3s,5S)-3-pyrazin-2-yloxy-8-azabicyclo[3.2.1]octane-8-carboxylate

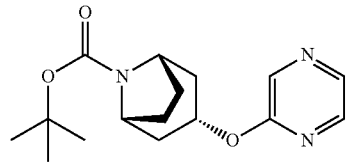

Following GP2, t-BuOK (0.1 g, 1 eq., 0.88 mmol) was added to a solution of tert-butyl (1R,3s,5S)-3-hydroxy-8-azabicyclo[3.2.1]octane-8-carboxylate (0.2 g, 1 eq., 0.88 mmol), and 2-chloropyrazine (0.08 mL, 1 eq., 0.88 mmol) in dry THF (7 mL). The reaction mixture was refluxed for 16 h. Then, the mixture was quenched with water (15 mL) and extracted with DCM (2×10 mL). The organic extracts were washed with brine (15 mL), dried over $Na_2SO_4$ and concentrated in vacuo to furnish the crude product, which was purified by flash chromatography eluting with DCM/MeOH (95:5) to give the pure title compound as white solid (0.096 g, 36%). UPLC-MS: $t_R$=2.27 min (generic method); MS (ESI) m/z calcd for $C_{16}H_{24}N_3O_3$ $(M+H)^+$: 306.2, found: 306.2.

tert-Butyl (1R,3r,5S)-3-(5-methylpyrazin-2-yl)oxy-8-azabicyclo[3.2.1]octane-8-carboxylate

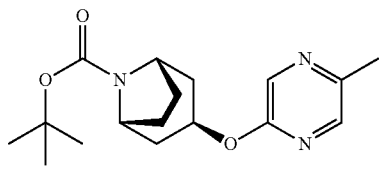

Following GP2, t-BuOK (0.1 g, 1 eq., 0.88 mmol) was added to a solution of tert-butyl (1R,3r,5S)-3-hydroxy-8-azabicyclo[3.2.1]octane-8-carboxylate (0.2 g, 1 eq., 0.88 mmol), and 2-chloro-5-methylpyrazine (0.11 g, 1 eq., 0.88 mmol) in dry THF (7 mL). The reaction mixture was refluxed for 16 h. Then, the mixture was quenched with water (15 mL) and extracted with DCM (2×10 mL). The organic extracts were washed with brine (15 mL), dried over $Na_2SO_4$ and concentrated in vacuo to furnish the crude product, which was purified by flash chromatography eluting with cyclohexane/EtOAc (0 to 80%) to give the pure title compound as colourless oil (0.07 g, 25%). UPLC-MS (method A): Rt. 2.58 min (TIC); ionization $ES^+$ 320 $[M+H]^+$. $^1$H NMR (400 MHz, DMSO-$d_6$): δ 8.17 (d, J=1.3 Hz, 1H), 8.06 (s, 1H), 5.26 (t, J=5.0 Hz, 1H), 4.18-4.03 (m, 2H), 2.39 (s, 3H), 2.17-1.97 (m, 4H), 1.96-1.77 (m, 4H), 1.42 (s, 9H).

tert-Butyl(1R,3r,5S)-3-[5-(ethoxymethyl)pyrazin-2-yl]oxy-8-azabicyclo[3.2.1]octane-8-carboxylate

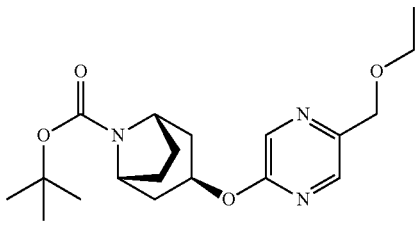

Following GP2, t-BuOK (0.02 g, 1 eq., 0.14 mmol) was added to a solution of tert-butyl (1R,3r,5S)-3-hydroxy-8-azabicyclo[3.2.1]octane-8-carboxylate (0.2 g, 1 eq., 0.88 mmol), and 2-chloro-5-(ethoxymethyl)pyrazine (0.03 g, 1 eq., 0.14 mmol) in dry THF (2 mL). The reaction mixture was refluxed for 16 h. Then, the mixture was quenched with water (15 mL) and extracted with DCM (2×10 mL). The organic extracts were washed with brine (15 mL), dried over Na$_2$SO$_4$ and concentrated in vacuo to furnish the crude product, which was purified by flash chromatography eluting with cyclohexane/EtOAc (0 to 80%) to give the pure title compound as colourless oil (0.01 g, 22%). UPLC-MS (method A): Rt. 2.63 min (TIC); ionization ES$^+$364 [M+H]$^+$. $^1$H NMR (400 MHz, DMSO-d$_6$): δ 8.25 (d, J=1.4 Hz, 1H), 8.20 (d, J=1.3 Hz, 1H), 5.32 (t, J=4.9 Hz, 1H), 4.50 (s, 2H), 4.18-4.01 (m, 2H), 3.55 (q, J=7.0 Hz, 2H), 2.13-2.01 (m, 4H), 1.96-1.78 (m, 4H), 1.43 (s, 9H), 1.16 (t, J=7.0 Hz, 3H).

tert-Butyl (1R,3r,5S)-3-[5-butylpyrazin-2-yl]oxy-8-azabicyclo[3.2.1]octane-8-carboxylate

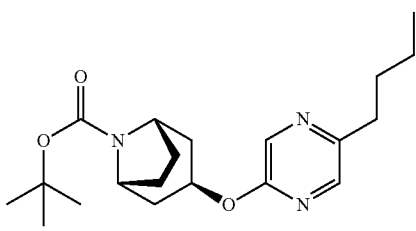

Step 1. To a solution of n-propyl-triphenylphosphonium bromide (0.745 g, 1.1 eq., 1.94 mmol) in dry THF (168 mL) n-BuLi (2.5M in hexane) (0.785 mL, 1.1 eq., 1.94 mmol) was added dropwise at 0° C. and the reaction mixture was stirred at the same temperature for 45 min. 5-Chloropyrazine-2-carbaldehyde (0.745 g, 1.1 eq., 1.94 mmol) was added and the crude mixture stirred at room temperature for 16 h, quenched with water (20 mL) and extracted with EtOAc (2×30 mL). The organic extracts were washed with brine, dried over Na$_2$SO$_4$ and concentrated in vacuo to furnish a crude product, which was purified by flash chromatography eluting with cyclohexane/EtOAc (9:1) to give (E/Z)-2-(but-1-enyl)-5-chloro-pyrazine (90 mg, 30%), as a 1:2 cis/trans mixture of isomers.

Step 2. Following GP2, t-BuOK (0.06 g, 1 eq., 0.54 mmol) was added to a solution of tert-butyl (1R,3r,5S)-3-hydroxy-8-azabicyclo[3.2.1]octane-8-carboxylate (0.123 g, 1 eq., 0.54 mmol), and (E/Z)-2-(but-1-enyl)-5-chloro-pyrazine (0.90 g, 1 eq., 0.54 mmol) in dry THF (2 mL). The reaction mixture was refluxed for 16 h. Then, the mixture was quenched with water (20 mL) and extracted with DCM (2×20 mL). The organic extracts were washed with brine, dried over Na$_2$SO$_4$ and concentrated in vacuo to furnish the crude product, which was purified by flash chromatography eluting with DCM/MeOH (95:5) to give tert-butyl (1R,3r,5S)-3-[5-[(E/Z)-butyl-1-enyl]-pyrazin-2-yl]oxy-8-azabicyclo[3.2.1]octane-8-carboxylate as a white solid (0.035 g, 16%), as a 1:2 cis/trans mixture of isomers.

Step 3. To a solution of tert-butyl (1R,3r,5S)-3-[5-[(E/Z)-butyl-1-enyl]-pyrazin-2-yl]oxy-8-azabicyclo[3.2.1]octane-8-carboxylate (0.030 g, 1.0 eq., 0.084 mmol) in EtOH (4.0 mL) were added cyclohexene (0.069 g, 10 eq., 0.84 mmol) and 10% Pd/C (ca. 30 mg). The mixture was kept under refluxing for 2 h, cooled to room temperature and the resulting suspension filtered and the residue concentrated to dryness. The crude product was partitioned between EtOAc and brine, dried over Na$_2$SO$_4$ and concentrated in vacuo to furnish the title compound (0.031 g, quant.), which was used in the next step without any further purification. UPLC-MS: t$_R$=2.33 min (apolar method); MS (ESI) m/z calcd for C$_{20}$H$_{32}$N$_3$O$_3$ (M+H)$^+$: 362.2, found: 362.2.

tert-Butyl (1R,3r,5S)-3-pyridazin-3-yloxy-8-N azabicyclo[3.2.1]octane-8-carboxylate

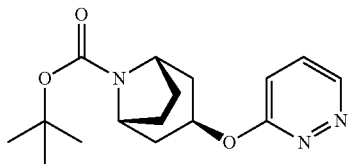

Following GP2, t-BuOK (0.1 g, 1 eq., 0.88 mmol) was added to a solution of tert-butyl (1R,3r,5S)-3-hydroxy-8-azabicyclo[3.2.1]octane-8-carboxylate (0.2 g, 1 eq., 0.88 mmol), and 3-chloropyridazine (0.1 g, 1 eq., 0.88 mmol) in dry THF (7 mL). The reaction mixture was refluxed for 16 h. Then, the mixture was quenched with water (15 mL) and extracted with DCM (2×10 mL). The organic extracts were washed with brine (15 mL), dried over Na$_2$SO$_4$ and concentrated in vacuo to furnish the crude product, which was purified by flash chromatography eluting with cyclohexane/EtOAc (0 to 70%) to give the pure title compound as colourless oil (0.06 g, 21%). UPLC-MS (method A): Rt. 2.26 min (TIC); ionization ES$^+$306 [M+H]$^+$. $^1$H NMR (400 MHz, DMSO-d$_6$): δ 8.87 (dd, J=4.4, 1.3 Hz, 1H), 7.62 (dd, J=8.9, 4.4 Hz, 1H), 7.20 (dd, J=9.0, 1.3 Hz, 1H), 5.52 (t, J=5.0 Hz, 1H), 4.18-3.99 (m, 2H), 2.19-2.00 (m, 4H), 1.99-1.84 (m, 4H), 1.43 (s, 9H).

tert-Butyl (1R,3r,5S)-3-(6-methylpyridazin-3-yl)oxy-8-azabicyclo[3.2.1]octane-8-carboxylate

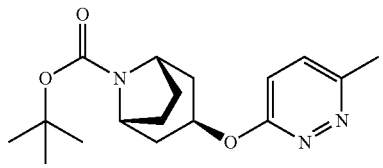

Following GP2, t-BuOK (0.1 g, 1 eq., 0.88 mmol) was added to a solution of tert-butyl (1R,3r,5S)-3-hydroxy-8-azabicyclo[3.2.1]octane-8-carboxylate (0.2 g, 1 eq., 0.88 mmol), and 3-chloro-6-methylpyridazine (0.11 g, 1 eq., 0.88 mmol) in dry THF (7 mL). The reaction mixture was refluxed for 16 h. Then, the mixture was quenched with water (15 mL) and extracted with DCM (2×10 mL). The organic extracts were washed with brine (15 mL), dried over Na$_2$SO$_4$ and concentrated in vacuo to furnish the crude product, which was purified by flash chromatography eluting with cyclohexane/EtOAc (0 to 70%) to give the pure title compound as colourless oil (0.04 g, 16%). UPLC-MS (method A): Rt. 2.43 min (TIC); ionization ES$^+$320 [M+H]$^+$. $^1$H NMR (400 MHz, DMSO-d$_6$): δ 7.49 (d, J=9.0 Hz, 1H), 7.09 (d, J=9.0 Hz, 1H), 5.44 (t, J=4.9 Hz, 1H), 4.25-4.00 (m, 2H), 2.62 (s, 3H), 2.13-1.99 (m, 4H), 1.94-1.85 (m, 4H), 1.42 (s, 9H).

tert-Butyl (1R,3r,5S)-3-(2-quinolyloxy)-8-azabicyclo[3.2.1]octane-8-carboxylate

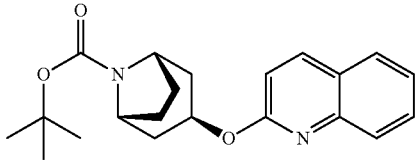

Following GP2, t-BuOK (0.1 g, 1 eq., 0.88 mmol) was added to a solution of tert-butyl (1R,3r,5S)-3-hydroxy-8-azabicyclo[3.2.1]octane-8-carboxylate (0.2 g, 1 eq., 0.88 mmol), and 2-chloroquinoline (0.14 g, 1 eq., 0.88 mmol) in dry THF (7 mL). The reaction mixture was refluxed for 16 h. Then, the mixture was quenched with water (15 mL) and extracted with DCM (2×10 mL). The organic extracts were washed with brine (15 mL), dried over Na$_2$SO$_4$ and concentrated in vacuo to furnish the crude product, which was purified by flash chromatography eluting with DCM/MeOH (0 to 2%) to give the pure title compound as colourless oil (0.05 g, 17%). UPLC-MS (method A): Rt. 2.46 min (TIC); ionization ES$^+$355 [M+H]$^+$. $^1$H NMR (400 MHz, DMSO-d$_6$): 8.25 (d, J=8.8 Hz, 1H), 7.91-7.84 (m, 1H), 7.72 (d, J=8.4 Hz, 1H), 7.66 (ddd, J=8.4, 6.8, 1.5 Hz, 1H), 7.43 (ddd, J=8.1, 6.9, 1.3 Hz, 1H), 7.01 (d, J=8.8 Hz, 1H), 5.56 (t, J=5.0 Hz, 1H), 4.17-4.10 (m, 2H), 2.20-2.05 (m, 4H), 2.01-1.87 (m, 4H), 1.44 (s, 9H).

tert-Butyl (1R,3r,5S)-3-quinoxalin-2-yloxy-8-azabicyclo[3.2.1]octane-8-carboxylate

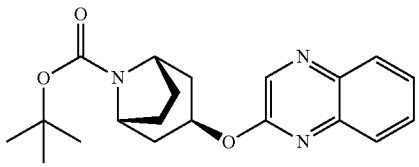

Following GP2, t-BuOK (0.09 g, 1 eq., 0.82 mmol) was added to a solution of tert-butyl (1R,3r,5S)-3-hydroxy-8-azabicyclo[3.2.1]octane-8-carboxylate (0.2 g, 1 eq., 0.82 mmol), and 2-chloroquinoxaline (0.14 g, 1 eq., 0.82 mmol) in dry THF (7 mL). The reaction mixture was refluxed for 16 h. Then, the mixture was quenched with water (15 mL) and extracted with DCM (2×10 mL). The organic extracts were washed with brine (15 mL), dried over Na$_2$SO$_4$ and concentrated in vacuo to furnish the crude product, which was purified by flash chromatography eluting with DCM/MeOH (0 to 2%) to give the pure title compound as colourless oil (0.1 g, 34%). UPLC-MS (method A): Rt. 3.20 min (TIC); ionization ES$^+$356 [M+H]$^+$. $^1$H NMR (400 MHz, DMSO-d$_6$): δ 8.59 (s, 1H), 8.01 (dd, J=8.2, 1.3 Hz, 1H), 7.85-7.71 (m, 2H), 7.64 (ddd, J=8.3, 6.7, 1.7 Hz, 1H), 5.54 (t, J=5.0 Hz, 1H), 4.21-4.08 (m, 2H), 2.25-2.07 (m, 4H), 2.02-1.88 (m, 4H), 1.44 (s, 9H).

tert-Butyl (1R,3r,5S)-3-(1,3-benzoxazol-2-yloxy-8-azabicyclo[3.2.1]octane-8-carboxylate

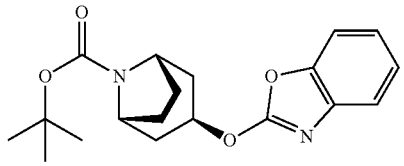

Following GP2, t-BuOK (0.1 g, 1 eq., 0.88 mmol) was added to a solution of tert-butyl (1R,3r,5S)-3-hydroxy-8-azabicyclo[3.2.1]octane-8-carboxylate (0.2 g, 1 eq., 0.88 mmol), and 2-chloro-1,3-benzoxazole (0.1 mL, 1 eq., 0.88 mmol) in dry THF (7 mL). The reaction mixture was refluxed for 16 h. Then, the mixture was quenched with water (15 mL) and extracted with DCM (2×10 mL). The organic extracts were washed with brine (15 mL), dried over Na$_2$SO$_4$ and concentrated in vacuo to furnish the crude product, which was purified by flash chromatography eluting with cyclohexane/EtOAc (0 to 60%) to give the pure title compound as colourless oil (0.06 g, 20%). UPLC-MS (method A): Rt. 1.75 min (TIC); ionization ES$^+$345 [M+H]$^+$. $^1$H NMR (400 MHz, DMSO-d$_6$): δ 7.53 (dd, J=7.5, 1.2 Hz, 1H), 7.51-7.47 (m, 1H), 7.27 (td, J=7.6, 1.4 Hz, 1H), 7.22 (td, J=7.7, 1.5 Hz, 1H), 5.36-5.24 (m, 1H), 4.19-4.03 (m, 2H), 2.23-1.85 (m, 8H), 1.43 (s, 9H).

tert-Butyl (1R,3r,5S)-3(4-methyl-1,3-benzoxazol-2-yloxy-8-azabicyclo[3.2.1]octane-8-carboxylate

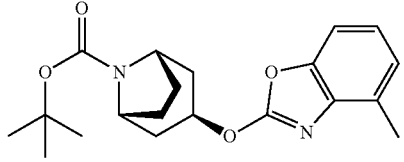

Following GP2, t-BuOK (0.14 g, 1 eq., 1.28 mmol) was added to a solution of tert-butyl (1R,3r,5S)-3-hydroxy-8-azabicyclo[3.2.1]octane-8-carboxylate (0.3 g, 1 eq., 1.28 mmol), and 2-chloro-4-methyl-1,3-benzoxazole (0.21 g, 1 eq., 1.28 mmol) in dry THF (8 mL). The reaction mixture was refluxed for 16 h. Then, the mixture was quenched with water (15 mL) and extracted with DCM (2×10 mL). The organic extracts were washed with brine (15 mL), dried over Na$_2$SO$_4$ and concentrated in vacuo to furnish the crude product, which was purified by flash chromatography eluting with cyclohexane/EtOAc (0 to 60%) to give the pure title compound as colourless oil (0.14 g, 39%). UPLC-MS (method A): Rt. 2.27 min (TIC); ionization ES+359 [M+H]+. $^1$H NMR (400 MHz, DMSO-d$_6$): δ 7.33 (dd, J=6.9, 2.3 Hz, 1H), 7.15-7.06 (m, 2H), 5.37-5.31 (m, 1H), 4.18-4.04 (m, 2H), 2.42 (s, 3H), 2.22-2.13 (m, 2H), 2.10-1.90 (m, 6H), 1.43 (s, 9H).

tert-Butyl (1R,3r,5S)-3-(5-methyl-1,3-benzoxazol-2-yloxy-8-azabicyclo[3.2.1]octane-8-carboxylate

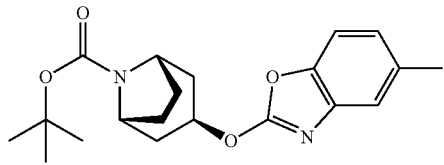

Following GP2, t-BuOK (0.17 g, 1 eq., 1.49 mmol) was added to a solution of tert-butyl (1R,3r,5S)-3-hydroxy-8-azabicyclo[3.2.1]octane-8-carboxylate (0.34 g, 1 eq., 1.49 mmol), and 2-chloro-5-methyl-1,3-benzoxazole (0.25 g, 1 eq., 1.49 mmol) in dry THF (9 mL). The reaction mixture was refluxed for 16 h. Then, the mixture was quenched with water (15 mL) and extracted with DCM (2×10 mL). The organic extracts were washed with brine (15 mL), dried over Na$_2$SO$_4$ and concentrated in vacuo to furnish the crude product, which was purified by flash chromatography eluting with cyclohexane/EtOAc (0 to 80%) to give the pure title compound as colourless oil (0.06 g, 11%). UPLC-MS (method A): Rt. 3.24 min (TIC); ionization ES$^+$359 [M+H]$^+$. $^1$H NMR (400 MHz, DMSO-d$_6$): δ 7.39 (d, J=8.2 Hz, 1H), 7.33-7.27 (m, 1H), 7.06-6.97 (m, 1H), 5.33-5.24 (m, 1H), 4.19-4.06 (m, 2H), 2.38 (s, 3H), 2.16 (d, J=15.9 Hz, 2H), 2.09-1.82 (m, 6H), 1.43 (s, 9H).

tert-Butyl (1R,3r,5S)-3-(pyrazin-2-yloxy)-9-azabicyclo[3.3.1]nonane-9-carboxylate

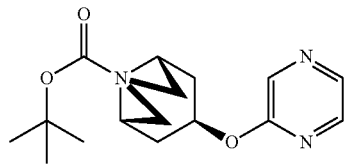

Following GP2, t-BuOK (0.09 g, 1 eq., 0.83 mmol) was added to a solution of tert-butyl (1R,3r,5S)-3-hydroxy-9-azabicyclo[3.3.1]nonane-9-carboxylate (0.2 g, 1 eq., 0.83 mmol), and 2-chloropyrazine (0.07 mL, 1 eq., 0.83 mmol) in dry THF (7 mL). The reaction mixture was refluxed for 16 h. Then, the mixture was quenched with water (15 mL) and extracted with DCM (2×10 mL). The organic extracts were washed with brine (15 mL), dried over Na$_2$SO$_4$ and concentrated in vacuo to furnish the crude product, which was purified by flash chromatography eluting with cyclohexane/EtOAc (0 to 50%) to give the pure title compound as colourless oil (0.09 g, 34%). UPLC-MS (method A): Rt. 2.77 min (TIC); ionization ES+320 [M+H]+. $^1$H NMR (400 MHz, DMSO-d$_6$): δ 8.27 (d, J=1.3 Hz, 1H), 8.23-8.17 (m, 2H), 5.02-4.92 (m, 1H), 4.35 (t, J=13.4 Hz, 2H), 2.46-2.29 (m, 2H), 2.28-2.13 (m, 1H), 1.65-1.45 (m, 7H), 1.43 (s, 9H).

tert-Butyl (1R,3r, 5S)-7-pyrazin-2-yloxy3-oxa-9-azabicyclo[3.3.1]nonane-9-carboxylate

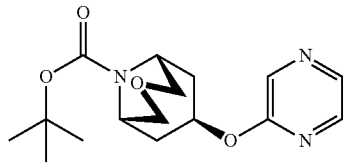

Following GP2, t-BuOK (0.09 g, 1 eq., 0.83 mmol) was added to a solution of tert-butyl (1R,3r,5S)-7-hydroxy-3-oxa-9-azabicyclo[3.3.1]nonane-9-carboxylate (0.2 g, 1 eq., 0.83 mmol), and 2-chloropyrazine (0.07 mL, 1 eq., 0.83 mmol) in dry THF (7 mL). The reaction mixture was refluxed for 16 h. Then, the mixture was quenched with water (15 mL) and extracted with DCM (2×10 mL). The organic extracts were washed with brine (15 mL), dried over Na$_2$SO$_4$ and concentrated in vacuo to furnish the crude product, which was purified by flash chromatography eluting with cyclohexane/EtOAc (0 to 80%) to give the pure title compound as colourless oil (0.14 g, 53%). UPLC-MS (method A): Rt. 2.24 min (TIC); ionization ES$^+$322 [M+H]$^+$. $^1$H NMR (400 MHz, DMSO-d$_6$). δ 8.22 (d, J=1.3 Hz, 1H), 8.21-8.18 (m, 1H), 8.18-8.16 (m, 1H), 5.03-4.95 (m, 1H), 4.13-3.99 (m, 2H), 3.67-3.60 (m, 2H), 3.47 (dd, J=11.1, 2.5 Hz, 2H), 2.44-2.31 (m, 2H), 1.84-1.71 (m, 2H), 1.44 (s, 9H).

(1R,5S)-7-Benzyl-9-pyrazin-2-yloxy-3-oxa-7-azabicyclo[3.3.1]nonane

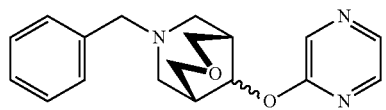

Following GP2, t-BuOK (0.432 g, 1 eq., 3.86 mmol) was added to a solution of 7-benzyl-3-oxa-7-azabicyclo[3.3.1]nonan-9-ol (0.9 g, 1 eq., 3.86 mmol), and 2-chloropyrazine (0.343 mL, 1 eq., 3.86 mmol) in dry THF (20 mL). The reaction mixture was left at room temperature for 4 h. Then, the mixture was quenched with water (15 mL) and extracted with EtOAc (2×20 mL). The organic extracts were washed with brine (15 mL), dried over Na$_2$SO$_4$ and concentrated in vacuo to furnish the crude product, which was purified by flash chromatography eluting with DCM/MeOH (95:5) to give the pure title compound as pale yellow oil (0.90 g, 75%), as a mixture of two stereoisomers. UPLC-MS: t$_R$=1.42 min (generic method); MS (ESI) m/z calcd for C$_{18}$H$_{22}$N$_3$O$_2$ (M+H)$^+$: 312.2, found: 312.2.

(1R,5S,8r)-3-Benzyl-8-pyrazin-2-yloxy-3-azabicyclo[3.2.1]octane

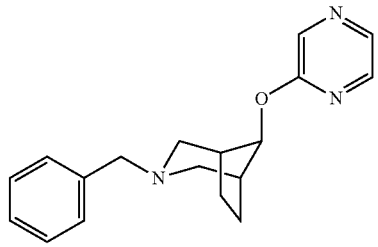 [SMILES: c1ccc(CN2CC3CCC(C2)C3Oc2cnccn2)cc1]

Following GP2, t-BuOK (0.052 g, 1 eq., 0.46 mmol) was added to a solution of 3-benzyl-3-azabicyclo[3.2.1]octan-8-ol (0.1 g, 1 eq., 0.46 mmol), and 2-chloropyrazine (0.04 mL, 1 eq., 0.46 mmol) in dry THF (5 mL). The reaction mixture was left at room temperature for 16 h. Then, the mixture was quenched with water (5 mL) and extracted with EtOAc (2×10 mL). The organic extracts were washed with brine, dried over $Na_2SO_4$ and concentrated in vacuo to furnish the crude product, which was purified by flash chromatography eluting with DCM/MeOH (95:5) to give the pure title compound as pale yellow oil (0.08 g, 59%). UPLC-MS: $t_R$=1.71 min (generic method); MS (ESI) m/z calcd for $C_{18}H_{22}N_3O$ (M+H)$^+$: 296.2, found: 296.1.

tert-Butyl (1r,5S)-9-(pyrazin-2-yloxy)-3-azabicyclo[3.3.1]nonane-3-carboxylate

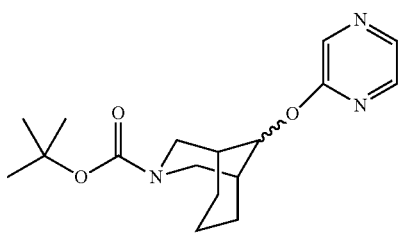 [SMILES: CC(C)(C)OC(=O)N1CC2CCCC(C1)C2Oc1cnccn1]

Following GP2, t-BuOK (0.116 g, 1 eq., 1.0 mmol) was added to a solution of tert-butyl (1R,5S)-9-hydroxy-3-azabicyclo[3.3.1]nonane-3-carboxylate (0.24 g, 1 eq., 1.0 mmol), and 2-chloropyrazine (0.092 mL, 1 eq., 1.0 mmol) in dry THF (20 mL). The reaction mixture was left at room temperature for 16 h. Then, the mixture was quenched with water (15 mL) and extracted with EtOAc (2×20 mL). The organic extracts were washed with brine (15 mL), dried over $Na_2SO_4$ and concentrated in vacuo to furnish the crude product, which was purified by flash chromatography eluting with DCM/MeOH (95:5) to give the pure title compound as colorless oil (0.25 g, 79%), as a 8:2 mixture of two stereoisomers. UPLC-MS: $t_R$=2.82 min (generic method); MS (ESI) m/z calcd for $C_{17}H_{26}N_3O_3$ (M+H)$^+$: 320.2, found: 320.2.

(1R,3s,5S)-3-Phenoxy-8-azabicyclo[3.2.1]octane trifluoroacetate

Following GP3, the title compound was obtained in quantitative yield and used in the next step without any further purification. UPLC-MS (method A): Rt. 0.41 min (TIC); ionization ES$^+$204 [M+H]$^+$. $^1$H NMR (400 MHz, DMSO-d$_6$): δ 8.64 (s, 2H), 7.33-7.23 (m, 2H), 7.02 (d, J=8.1 Hz, 2H), 6.95 (t, J=7.3 Hz, 1H), 4.84-4.69 (m, 1H), 4.16-4.02 (m, 2H), 2.30-2.18 (m, 2H), 2.14-2.02 (m, 2H), 2.01-1.92 (m, 2H), 1.84-1.71 (m, 2H).

(1R,3r,5S)-3-Phenoxy-8-azabicyclo[3.2.1]octane trifluoroacetate

Following GP3, the title compound was obtained in quantitative yield and used in the next step without any further purification. UPLC-MS (method A): Rt. 0.41 min (TIC); ionization ES$^+$204 [M+H]$^+$.

(1R,3s,5S)-3-(3-Methylphenoxy)-8-azabicyclo[3.2.1]octane trifluoroacetate

Following GP3, the title compound was obtained in quantitative yield and used in the next step without any further purification. $^1$H NMR (400 MHz, DMSO-d$_6$): δ 8.66 (bs, 2H), 7.16 (t, J=7.6 Hz, 1H), 6.81 (s, 1H), 6.80-6.72 (m, 2H), 5.03-4.55 (m, 1H), 4.32-3.79 (m, 2H), 2.27 (s, 3H), 2.26-2.18 (m, 2H), 2.12-2.02 (m, 2H), 2.02-1.91 (m, 2H), 1.84-1.69 (m, 2H).

(1R,3r,5S)-3-(3-Methylphenoxy)-8-azabicyclo[3.2.1]octane trifluoroacetate

Following GP3, the title compound was obtained in quantitative yield and used in the next step without any further purification. $^1$H NMR (400 MHz, DMSO-d$_6$): δ 8.60 (bs, 2H), 7.19 (t, J=7.8 Hz, 1H), 6.82-6.69 (m, 3H), 4.70 (t, J=4.7 Hz, 1H), 4.01-3.95 (m, 2H), 2.28 (s, 3H), 2.25-2.17 (m, 4H), 2.08-2.01 (m, 2H), 2.00-1.93 (m, 2H).

(1R,3r,5S)-3-(4-Ethylphenoxy)-8-azabicyclo[3.2.1]octane trifluoroacetate

Following GP3, the title compound was obtained in quantitative yield and used in the next step without any further purification. UPLC-MS (method A): Rt. 0.69 min (TIC); ionization ES$^+$232 [M+H]$^+$.

(1R,3s,5S)-3-(4-Butylphenoxy)-8-azabicyclo[3.2.1]octane trifluoroacetate

Following GP3, the title compound was obtained in quantitative yield and used in the next step without any further purification. $^1$H NMR (400 MHz, DMSO-d$_6$): δ 8.63 (bs, 2H), 7.09 (d, J=8.4 Hz, 2H), 6.9-6.87 (m, 2H), 4.74-4.62 (m, 1H), 4.11-4.02 (m, 2H), 2.50-2.47 (m, 2H), 2.27-2.15 (m, 2H), 2.08-1.88 (m, 4H), 1.82-1.71 (m, 2H), 1.56-1.42 (m, 2H), 1.35-1.21 (m, 2H), 0.89 (t, J=7.3 Hz, 3H).

(1R,3r,5S)-3-(4-Butylphenoxy)-8-azabicyclo[3.2.1]octane trifluoroacetate

Following GP3, the title compound was obtained in quantitative yield and used in the next step without any further purification. $^1$H NMR (400 MHz, DMSO-d$_6$): δ 8.58 (bs, J=37.3 Hz, 2H), 7.17-7.08 (m, 2H), 6.89-6.81 (m, 2H), 4.67 (t, J=4.7 Hz, 1H), 4.01-3.95 (m, 2H), 2.27-2.13 (m, 4H), 2.07-1.89 (m, 4H), 1.57-1.45 (m, 3H), 1.34-1.21 (m, 3H), 0.89 (t, J=7.4, 3.8 Hz, 3H).

(1R,3r,5S)-3-(4-Hexylphenoxy)-8-azabicyclo[3.2.1]octane trifluoroacetate

Following GP3, the title compound was obtained in quantitative yield and used in the next step without any further purification. UPLC-MS (method A): Rt. 1.87 min (TIC); ionization ES⁺288 [M+H]⁺.

(1R,3r,5S)-3-(4-Isopropylphenoxy)-8-azabicyclo[3.2.1]octane trifluoroacetate Following GP3, the title compound was obtained in quantitative yield and used in the next step without any further purification. UPLC-MS (method A): Rt. 0.41 min (TIC); ionization ES⁺229 [M+H]⁺.

(1R,3r,5S)-3-(4-Methoxyphenoxy)-8-azabicyclo[3.2.1]octane trifluoroacetate

Following GP3, the title compound was obtained in quantitative yield and used in the next step without any further purification. UPLC-MS (method A): Rt. 0.45 min (TIC); ionization ES⁺234 [M+H]⁺.

(1R,3r,5S)-3-(4-Propoxyphenoxy)-8-azabicyclo[3.2.1]octane trifluoroacetate

Following GP3, the title compound was obtained in quantitative yield and used in the next step without any further purification. UPLC-MS (method A): Rt. 0.65 min (TIC); ionization ES⁺262 [M+H]⁺.

(1R,3s,5S)-3-(4-Cyanophenoxy)-8-azabicyclo[3.2.1]octane trifluoroacetate

Following GP3, the title compound was obtained in quantitative yield and used in the next step without any further purification UPLC-MS (method A): Rt. 0.41 min (TIC); ionization ES⁺229 [M+H]⁺. ¹H NMR (400 MHz, DMSO-d₆): δ 8.69 (s, 2H), 7.77-7.72 (m, 2H), 7.64-7.60 (m, 2H), 4.93-4.82 (m, 1H), 4.12-4.03 (m, 2H), 2.32-2.20 (m, 2H), 2.16-2.05 (m, 2H), 2.01-1.90 (m, 2H), 1.88-1.74 (m, 2H).

(1R,3r,5S)-3-(4-Cyanophenoxy)-8-azabicyclo[3.2.1]octane trifluoroacetate

Following GP3, the title compound was obtained in quantitative yield and used in the next step without any further purification UPLC-MS (method A): Rt. 0.39 min (TIC); ionization ES⁺229 [M+H]⁺. ¹H NMR (400 MHz, DMSO-d₆): δ 8.64 (d, J=44.2 Hz, 2H), 7.83-7.75 (m, 2H), 7.15-7.08 (m, 2H), 4.83 (t, J=4.6 Hz, 1H), 4.00-3.94 (m, 2H), 2.25 (dt, J=16.1, 4.1 Hz, 2H), 2.21-2.13 (m, 2H), 2.08-1.95 (m, 4H).

(1R,3r,5S)-3-(2-Fluoro-4-methyl-phenoxy)-8-azabicyclo[3.2.1]octane trifluoroacetate Following GP3, the title compound was obtained in quantitative yield and used in the next step without any further purification. UPLC-MS (method A): Rt. 0.53 min (TIC); ionization ES⁺236 [M+H]⁺.

(1R,3r,5S)-3-(Pyrid-2-yloxy)-8-azabicyclo[3.2.1]octane trifluoroacetate

Following GP3, the title compound was obtained in quantitative yield and used in the next step without any further purification. UPLC-MS (method A): Rt. 0.41 min (TIC); ionization ES⁺205 [M+H]⁺.

(1R,3r,5S)-3-[(5-Methyl-2-pyridyl)oxy]-8-azabicyclo[3.2.1]octane trifluoroacetate Following GP3, the title compound was obtained in quantitative yield and used in the next step without any further purification. UPLC-MS (method A): Rt. 1.57 min (TIC); ionization ES⁺219 [M+H]⁺.

(1R,3r,5S)-3-Pyrazin-2-yloxy-8-azabicyclo[3.2.1]octane trifluoroacetate

Following GP3, the title compound was obtained in quantitative yield and used in the next step without any further purification. UPLC-MS (method A): Rt. 0.36 min (TIC); ionization ES⁺206 [M+H]⁺. ¹H NMR (400 MHz, DMSO-d₆): δ 8.66 (d, J=46.1 Hz, 2H), 8.34-8.29 (m, 1H), 8.24-8.17 (m, 2H), 5.27 (t, J=4.8 Hz, 1H), 4.06-3.94 (m, 2H), 2.34-2.21 (m, 4H), 2.07 (d, J=15.9 Hz, 2H), 2.02-1.95 (m, 2H).

(1R,3r,5S)-3-(5-Methylpyrazin-2-yl)oxy-8-azabicyclo[3.2.1]octane trifluoroacetate Following GP3, the title compound was obtained in quantitative yield and used in the next step without any further purification. UPLC-MS (method A): Rt. 1.25 min (TIC); ionization ES⁺220 [M+H]+.

(1R,3r,5S)-3-[5-(Ethoxymethyl)pyrazin-2-yl]oxy-8-azabicyclo[3.2.1]octane trifluoroacetate Following GP3, the title compound was obtained in quantitative yield and used in the next step without any further purification. UPLC-MS (method A): Rt. 1.23 min (TIC); ionization ES⁺264 [M+H]⁺.

(1R,3r,5S)-3-Pyridazin-3-yloxy-8-azabicyclo[3.2.1]octane trifluoroacetate

Following GP3, the title compound was obtained in quantitative yield and used in the next step without any further purification. UPLC-MS (method A): Rt. 0.92 min (TIC); ionization ES⁺206 [M+H]⁺.

(1R,3r,5S)-3-(6-Methylpyridazin-3-yl)oxy-8-azabicyclo[3.2.1]octane trifluoroacetate Following GP3, the title compound was obtained in quantitative yield and used in the next step without any further purification. UPLC-MS (method A): Rt. 1.10 min (TIC); ionization ES⁺220 [M+H]⁺. ¹H NMR (400 MHz, DMSO-d₆): δ 8.62 (d, J=41.8 Hz, 2H), 7.68-7.43 (m, 1H), 7.20 (d, J=9.0 Hz, 1H), 5.53-5.20 (m, 1H), 4.02 (s, 2H), 2.53 (s, 3H), 2.36-2.26 (m, 2H), 2.23 (d, J=8.0 Hz, 2H), 2.13 (d, J=15.8 Hz, 2H), 1.99 (td, J=7.5, 4.3 Hz, 2H).

2-[(1R,3r,5S)-8-Azabicyclo[3.2.1]octan-3-yloxy]quinoline trifluoroacetate

Following GP3, the title compound was obtained in quantitative yield and used in the next step without any further purification. UPLC-MS (method A): Rt. 0.56 min (TIC); ionization ES⁺255 [M+H]⁺.

2-[(1R,3r,5S)-8-Azabicyclo[3.2.1]octan-3-yloxy]-quinoxaline trifluoroacetate Following GP3, the title compound was obtained in quantitative yield and used in the next step without any further purification. UPLC-MS (method A): Rt. 1.58 min (TIC); ionization ES⁺256 [M+H]⁺.

2-[(1R,3r,5S)-8-Azabicyclo[3.2.1]octan-3-yloxy]-1,3-benzoxazole trifluoroacetate Following GP3, the title compound was obtained in quantitative yield and used in the next step without any further purification. UPLC-MS (method A): Rt. 0.44 min (TIC); ionization ES⁺245 [M+H]⁺.

2-[(1R,3r,5S)-8-Azabicyclo[3.2.1]octan-3-yloxy]-4-methyl-1,3-benzoxazole trifluoroacetate Following GP3, the title compound was obtained in quantitative yield and used in the next step without any further purification. UPLC-MS (method A): Rt. 0.49 min (TIC); ionization ES⁺259 [M+H]⁺.

2-[(1R,3r,5S)-8-Azabicyclo[3.2.1]octan-3-yloxy]-5-methyl-1,3-benzoxazole trifluoroacetate Following GP3, the title compound was obtained in quantitative yield and used in the next step without any further purification. UPLC-MS (method A): Rt. 1.81 min (TIC); ionization ES⁺259 [M+H]⁺.

(1R,3r,5S)-3-(4-Formyl-phenoxy)-8-azabicyclo[3.2.1]octane trifluoroacetate

Following GP3, the title compound was obtained in quantitative yield and used in the next step without any further purification. UPLC-MS: $t_R$=1.35 min (generic method); MS (ESI) m/z calcd for $C_{14}H_{18}NO_2$ (M+H)⁺: 232.1, found: 232.2.

(1R,3r,5S)-3-(4-Trifluoromethyl-phenoxy)-8-azabicyclo[3.2.1]octane trifluoroacetate Following GP3, the title compound was obtained in quantitative yield and used in the next step without any further purification. UPLC-MS: $t_R$=2.04 min (generic method); MS (ESI) m/z calcd for $C_{14}H_{17}F_3NO$ (M+H)⁺: 272.1, found: 272.2. ¹H NMR (400 MHz, DMSO-d₆) δ 8.69 (br d, J=31.8 Hz, 1H), 7.67 (d, J=8.6 Hz, 2H), 7.14 (d, J=8.6 Hz, 2H), 4.84 (app-t, J=4.6 Hz, 1H), 3.99 (br s, 2H), 2.32-2.11 (m, 4H), 2.10-1.90 (m, 4H).

(1R,3r,5S)-3-(Pyrazin-2-yloxy)-9-azabicyclo[3.3.1]nonane trifluoroacetate

Following GP3, the title compound was obtained in quantitative yield and used in the next step without any further purification. UPLC-MS (method A): Rt. 1.18 min (TIC); ionization ES⁺220 [M+H]⁺.

(1R,3s,5S)-3-(Pyrazin-2-yloxy)-9-azabicyclo[3.3.1]nonane trifluoroacetate

Following GP3, the title compound was obtained in quantitative yield and used in the next step without any further purification. UPLC-MS (method A): Rt. 0.39 min (TIC); ionization ES⁺220 [M+H]⁺.

(1R,3r,5S)-7-Pyrazin-2-yloxy-3-oxa-9-azabicyclo[3.3.1]nonane trifluoroacetate

Following GP3, the title compound was obtained in quantitative yield and used in the next step without any further purification. UPLC-MS (method A): Rt. 0.81 min (TIC); ionization ES⁺222 [M+H]⁺.

(1R,3s,5S)-7-Pyrazin-2-yloxy-3-oxa-9-azabicyclo[3.3.1]nonane trifluoroacetate

Following GP3, the title compound was obtained in quantitative yield and used in the next step without any further purification. UPLC-MS (method A): Rt. 1.59 min (TIC); ionization ES⁺222 [M+H]⁺.

(1R,5s,9R)-9-Pyrazin-2-yloxy-3-azabicyclo[3.3.1]nonane trifluoroacetate

Following GP3, the title compound was obtained in quantitative yield as a white solid, as a ca. 8:2 mixture of two stereoisomers, which was used in the next step without any further purification. UPLC-MS: $t_R$=1.17 min (generic method); MS (ESI) m/z calcd for $C_{12}H_{18}N_3O$ (M+H)⁺: 220.1, found: 220.1.

Example 1. (1R,3s,5S)-8-[(3,5-Dimethyl-1H-pyrazol-4-yl)sulfonyl]-3-phenoxy-8-azabicyclo[3.2.1]octane Following GP4, (1R,3s,5S)-3-phenoxy-8-azabicyclo[3.2.1]octane trifluoroacetate (0.07 g, 1.1 eq., 0.24 mmol) was dissolved in THF (5 mL). Triethylamine (0.12 mL, 4 eq., 0.88 mmol) was then added followed by 3,5-dimethyl-1H-pyrazole-4-sulfonyl chloride (0.04 g, 1 eq., 0.22 mmol). The reaction mixture was stirred at room temperature for 16 h. Then it was quenched by the addition of HCl 2N (5 mL) and extracted with EtOAc (2×5 mL). The organic extracts were dried over Na₂SO₄ and concentrated in vacuo to furnish the crude product, which was purified by flash chromatography eluting with DCM/MeOH (0 to 2%) to give the pure title compound as white solid (0.05 g, 57%). UPLC-MS (method A): Rt. 2.32 min (TIC); ionization ES⁺362 [M+H]⁺. ¹H NMR (400 MHz, DMSO-d₆): δ 13.00 (s, 1H), 7.30-7.21 (m, 2H), 6.99-6.94 (m, 2H), 6.92 (td, J=7.3, 1.1 Hz, 1H), 4.77-4.57 (m, 1H), 4.20-4.10 (m, 2H), 2.38 (s, 3H), 2.29 (s, 3H), 2.23-2.08 (m, 2H), 1.89-1.76 (m, 2H), 1.71-1.63 (m, 2H), 1.63-1.52 (m, 2H). ¹³C NMR (101 MHz, DMSO-d₆): δ 157.51, 129.97, 121.22, 116.25, 114.93, 69.31, 55.84, 38.40, 28.53, 13.39, 10.98.

Example 2. (1R,3r,5S)-8-[(3,5-Dimethyl-1H-pyrazol-4-yl)sulfonyl]-3-phenoxy-8-azabicyclo[3.2.1]octane Following GP4, (1R,3r,5S)-3-phenoxy-8-azabicyclo[3.2.1]octane trifluoroacetate (0.07 g, 1.1 eq., 0.22 mmol) was dissolved in THF (3 mL). Triethylamine (0.11 mL, 4 eq., 0.8 mmol) was then added followed by 3,5-dimethyl-1H-pyrazole-4-sulfonyl chloride (0.04 g, 1 eq., 0.2 mmol). The reaction mixture was stirred at room temperature for 16 h. Then it was quenched by the addition of HCl 2N (5 mL) and extracted with EtOAc (2×5 mL). The organic extracts were dried over Na₂SO₄ and concentrated in vacuo to furnish the crude product, which was purified by flash chromatography eluting with DCM/MeOH (0 to 2%) to give the pure title compound as white solid (0.02 g, 33%). UPLC-MS (method A): Rt. 2.44 min (TIC); ionization ES⁺362 [M+H]⁺. ¹H NMR (400 MHz, DMSO-d₆): δ 13.04 (bs, 1H), 7.34-7.24 (m, 2H), 6.92 (t, J=7.3 Hz, 1H), 6.87 (d, J=8.1 Hz, 2H), 4.68 (t, J=4.7 Hz, 1H), 4.21-3.95 (m, 2H), 2.33 (s, 6H), 2.13-1.90 (m, 6H), 1.69-1.57 (m, 2H).

Example 3. (1R,3s,5S)-3-(4-Butylphenoxy)-8-[(3,5-dimethyl-1H-pyrazol-4-yl)sulfonyl]-8-azabicyclo[3.2.1]octane Following GP4, (1R,3s,5S)-3-(4-butylphenoxy)-8-azabicyclo[3.2.1]octane trifluoroacetate (0.15 g, 1.1 eq., 0.41 mmol) was dissolved in THF (3 mL). Triethylamine (0.21 mL, 4 eq., 1.48 mmol) was then added followed by 3,5-dimethyl-1H-pyrazole-4-sulfonyl chloride (0.07 g, 1 eq., 0.37 mmol). The reaction mixture was stirred at room temperature for 16 h. Then it was quenched by the addition of HCl 2N (5 mL) and extracted with EtOAc (2×5 mL). The organic extracts were dried over $Na_2SO_4$ and concentrated in vacuo to furnish the crude product, which was purified by flash chromatography eluting with DCM/MeOH (0 to 5%) to give the pure title compound as white solid (0.06 g, 36%). UPLC-MS (method A): Rt. 3.03 min (TIC); ionization $ES^+418$ [M+H]$^+$. $^1$H NMR (400 MHz, DMSO-$d_6$): δ 13.01 (bs, 1H), 7.11-7.01 (m, 2H), 6.91-6.80 (m, 2H), 4.61 (tt, J=10.8, 6.0 Hz, 1H), 4.19-4.11 (m, 2H), 2.50-2.45 (m, 2H), 2.32 (s, 6H), 2.19-2.08 (m, 2H), 1.84-1.74 (m, 2H), 1.68-1.61 (m, 2H), 1.60-1.42 (m, 4H), 1.34-1.18 (m, 2H), 0.88 (t, J=7.3 Hz, 3H). $^{13}$C NMR (101 MHz, DMSO-$d_6$): δ 155.51, 135.04, 129.63, 116.18, 114.92, 69.46, 55.84, 38.48, 34.35, 33.81, 28.51, 22.11, 14.22.

Example 4. (1R,3r,5S)-3-(3-Methylphenoxy)-8-[(3,5-dimethyl-1H-pyrazol-4-yl)sulfonyl]-8-azabicyclo[3.2.1]octane Following GP4, (1R,3r,5S)-3-(3-methylphenoxy)-8-azabicyclo[3.2.1]octane trifluoroacetate (0.19 g, 1.1 eq., 0.57 mmol) was dissolved in THF (4 mL). Triethylamine (0.29 mL, 4 eq., 2.08 mmol) was then added followed by 3,5-dimethyl-1H-pyrazole-4-sulfonyl chloride (0.1 g, 1 eq., 0.52 mmol). The reaction mixture was stirred at room temperature for 16 h. Then it was quenched by the addition of HCl 2N (5 mL) and extracted with EtOAc (2×5 mL). The organic extracts were dried over $Na_2SO_4$ and concentrated in vacuo to furnish the crude product, which was purified by flash chromatography eluting with DCM/MeOH (0 to 5%) and then by preparative HPLC purification to give the pure title compound as white solid (0.02 g, 10%). UPLC-MS (method A): Rt. 2.61 min (TIC); ionization $ES^+376$ [M+H]$^+$. $^1$H NMR (400 MHz, DMSO-$d_6$): δ 7.14 (t, J=7.8 Hz, 1H), 6.73 (d, J=7.5 Hz, 1H), 6.70-6.67 (m, 1H), 6.65 (dd, J=8.1, 2.5 Hz, 1H), 4.64 (t, J=4.7 Hz, 1H), 4.11-4.03 (m, 2H), 2.31 (s, 6H), 2.25 (s, 3H), 2.07-1.89 (m, 6H), 1.65-1.56 (m, 2H). $^{13}$C NMR (101 MHz, DMSO-$d_6$): δ 157.14, 139.66, 129.82, 121.83, 116.81, 114.93, 112.78, 69.19, 55.44, 36.85, 28.39, 21.51, 11.91.

Example 5. (1R,3s,5S)-3-(3-Methylphenoxy)-8-[(3,5-dimethyl-1H-pyrazol-4-yl)sulfonyl]-8-azabicyclo[3.2.1]octane Following GP4, (1R,3s,5S)-3-(3-methylphenoxy)-8-azabicyclo[3.2.1]octane trifluoroacetate (0.17 g, 1.1 eq., 0.51 mmol) was dissolved in THF (3 mL). Triethylamine (0.26 mL, 4 eq., 1.84 mmol) was then added followed by 3,5-dimethyl-1H-pyrazole-4-sulfonyl chloride (0.09 g, 1 eq., 0.46 mmol). The reaction mixture was stirred at room temperature for 16 h. Then it was quenched by the addition of HCl 2N (5 mL) and extracted with EtOAc (2×5 mL). The organic extracts were dried over $Na_2SO_4$ and concentrated in vacuo to furnish the crude product, which was purified by flash chromatography eluting with DCM/MeOH (0 to 5%) and then by preparative HPLC purification to give the pure title compound as white solid (0.05 g, 30%). UPLC-MS (method A): Rt. 2.49 min (TIC); ionization $ES^+376$ [M+H]$^+$. $^1$H NMR (400 MHz, DMSO-$d_6$): δ 7.12 (t, J=7.7 Hz, 1H), 6.79-6.68 (m, 3H), 4.65 (tt, J=10.8, 6.0 Hz, 1H), 4.20-4.09 (m, 2H), 2.32 (s, 6H), 2.25 (s, 3H), 2.20-2.10 (m, 2H), 1.85-1.74 (m, 2H), 1.68-1.61 (m, 2H), 1.61-1.49 (m, 2H). $^{13}$C NMR (101 MHz, DMSO-$d_6$): δ 157.49, 139.51, 129.68, 122.00, 116.92, 114.93, 113.20, 69.20, 55.84, 38.43, 28.52, 21.49, 12.34.

Example 8. (1R,3r,5S)-3-(4-Cyanophenoxy)-8-[(3,5-dimethyl-1H-pyrazol-4-yl)sulfonyl]-8-azabicyclo[3.2.1]octane Following GP4, (1R,3r,5S)-3-(4-cyanophenoxy)-8-azabicyclo[3.2.1]octane trifluoroacetate (0.2 g, 1.1 eq., 0.57 mmol) was dissolved in THF (4 mL). Triethylamine (0.29 mL, 4 eq., 2.08 mmol) was then added followed by 3,5-dimethyl-1H-pyrazole-4-sulfonyl chloride (0.1 g, 1 eq., 0.52 mmol). The reaction mixture was stirred at room temperature for 16 h. Then it was quenched by the addition of HCl 2N (5 mL) and extracted with EtOAc (2×5 mL). The organic extracts were dried over $Na_2SO_4$ and concentrated in vacuo to furnish the crude product, which was purified by flash chromatography eluting with cyclohexane/EtOAc (0 to 100%) to give the pure title compound as white solid (0.11 g, 57%). UPLC-MS (method A): Rt. 2.16 min (TIC); ionization $ES^-$ 385 [M−H]$^-$. $^1$H NMR (400 MHz, DMSO-$d_6$): δ 13.05 (s, 1H), 7.84-7.65 (m, 2H), 7.10-7.01 (m, 2H), 4.80 (t, J=4.8 Hz, 1H), 4.15-4.05 (m, 2H), 2.31 (bs, 6H), 2.08 (dt, J=15.0, 4.3 Hz, 2H), 1.98-1.88 (m, 4H), 1.68-1.55 (m, 2H). $^{13}$C NMR (101 MHz, DMSO-$d_6$): δ 160.79, 134.78, 134.78, 119.59, 116.78, 114.83, 103.11, 70.29, 55.31, 36.74, 28.35.

Example 9. (1R,3s,5S)-3-(4-Cyanophenoxy)-8-[(3,5-dimethyl-1H-pyrazol-4-yl)sulfonyl]-8-azabicyclo[3.2.1]octane Following GP4, (1R,3s,5S)-3-(4-cyanophenoxy)-8-azabicyclo[3.2.1]octane trifluoroacetate (0.14 g, 1.1 eq., 0.41 mmol) was dissolved in THF (3 mL). Triethylamine (0.21 mL, 4 eq., 1.48 mmol) was then added followed by 3,5-dimethyl-1H-pyrazole-4-sulfonyl chloride (0.07 g, 1 eq., 0.37 mmol). The reaction mixture was stirred at room temperature for 16 h. Then it was quenched by the addition of HCl 2N (5 mL) and extracted with EtOAc (2×5 mL). The organic extracts were dried over $Na_2SO_4$ and concentrated in vacuo to furnish the crude product, which was purified by flash chromatography eluting with cyclohexane/EtOAc (0 to 100%) to give the pure title compound as white solid (0.09 g, 57%). UPLC-MS (method A): Rt. 2.12 min (TIC); ionization $ES^+387$ [M+H]$^+$. $^1$H NMR (400 MHz, DMSO-$d_6$): δ 13.05 (bs, 1H), 7.99-7.49 (m, 2H), 7.42-7.07 (m, 2H), 4.83 (tt, J=10.7, 6.0 Hz, 1H), 4.36-4.11 (m, 2H), 2.32 (bs, 6H), 2.23-2.14 (m, 2H), 1.89-1.79 (m, 2H), 1.71-1.54 (m, 4H). $^{13}$C NMR (101 MHz, DMSO-$d_6$): δ 161.09, 151.84, 134.65, 119.59, 116.94, 114.85, 103.23, 70.04, 55.78, 37.94, 28.38, 11.77.

Example 13. (1R,3r,5S)-8-[(3,5-Dimethyl-1H-pyrazol-4-yl)sulfonyl]-3-pyrazin-2-yloxy-8-azabicyclo[3.2.1]octane Following GP4, (1R,3r,5S)-3-pyrazin-2-yloxy-8-azabicyclo[3.2.1]octane trifluoroacetate (0.11 g, 1.1 eq., 0.34 mmol)

was dissolved in THF (3 mL). Triethylamine (0.17 mL, 4 eq., 2.08 mmol) was then added followed by 3,5-dimethyl-1H-pyrazole-4-sulfonyl chloride (0.06 g, 1 eq., 0.31 mmol). The reaction mixture was stirred at room temperature for 16 h. Then it was quenched by the addition of HCl 2N (5 mL) and extracted with EtOAc (2×5 mL). The organic extracts were dried over $Na_2SO_4$ and concentrated in vacuo to furnish the crude product, which was purified by flash chromatography eluting with cyclohexane/EtOAc (0 to 80%) to give the pure title compound as white solid (0.04 g, 57%). UPLC-MS (method A): Rt. 1.82 min (TIC); ionization ES$^+$364 [M+H]$^+$. $^1$H NMR (400 MHz, DMSO-d$_6$): δ 8.23 (s, 1H), 8.19-8.12 (m, 2H), 5.26 (t, J=4.9 Hz, 1H), 4.15-4.07 (m, 2H), 2.31 (s, 6H), 2.14-2.05 (m, 2H), 2.05-2.00 (m, 2H), 2.00-1.92 (m, 2H), 1.68-1.56 (m, 2H). $^{13}$C NMR (101 MHz, DMSO-d$_6$): δ 159.24, 141.21, 137.08, 136.31, 114.87, 68.85, 55.47, 37.30, 28.36, 12.14.

Example 14. (1R,3r,5S)-3-(4-Butylphenoxy)-8-(1,3,5-trimethylpyrazol-4-yl)sulfonyl-8-azabicyclo[3.2.1]octane Following GP4, (1R,3r,5S)-3-(4-butylphenoxy)-8-azabicyclo[3.2.1]octane trifluoroacetate (0.24 g, 1.1 eq., 0.64 mmol) was dissolved in THF (4 mL). Triethylamine (0.32 mL, 4 eq., 2.32 mmol) was then added followed by 1,3,5-trimethylpyrazole-4-sulfonyl chloride (0.12 g, 1 eq., 0.58 mmol). The reaction mixture was stirred at room temperature for 16 h. Then it was quenched by the addition of HCl 2N (5 mL) and extracted with EtOAc (2×5 mL). The organic extracts were dried over $Na_2SO_4$ and concentrated in vacuo to furnish the crude product, which was purified by flash chromatography eluting with cyclohexane/EtOAc (0 to 100%) to give the pure title compound as white solid (0.14 g, 55%). UPLC-MS (method A): Rt. 2.37 min (TIC); ionization ES$^+$432 [M+H]$^+$. $^1$H NMR (400 MHz, DMSO-d$_6$): δ 7.17-7.03 (m, 2H), 6.85-6.68 (m, 2H), 4.63 (t, J=4.4 Hz, 1H), 4.14-4.02 (m, 2H), 3.71 (s, 3H), 2.50-2.48 (m, 2H), 2.42 (s, 3H), 2.26 (s, 3H), 2.09-1.89 (m, 6H), 1.69-1.59 (m, 2H), 1.57-1.45 (m, 2H), 1.35-1.22 (m, 2H), 0.89 (t, J=7.3 Hz, 3H). $^{13}$C NMR (101 MHz, DMSO-d$_6$): δ 155.13, 146.38, 142.19, 129.78, 115.86, 115.37, 69.34, 55.45, 36.74, 36.69, 34.38, 33.81, 28.42, 22.17, 14.24, 13.32, 10.64.

Example 15. 4-[[(1R,3r,5S)-3-(4-Butylphenoxy)-8-azabicyclo[3.2.1]octan-8-yl]sulfonyl]-3,5-dimethyl-isoxazole Following GP4, (1R,3r,5S)-3-(4-butylphenoxy)-8-azabicyclo[3.2.1]octane trifluoroacetate (0.24 g, 1.1 eq., 0.64 mmol) was dissolved in THF (4 mL). Triethylamine (0.32 mL, 4 eq., 2.32 mmol) was then added followed by 3,5-dimethylisoxazole-4-sulfonyl chloride (0.11 g, 1 eq., 0.58 mmol). The reaction mixture was stirred at room temperature for 16 h. Then it was quenched by the addition of HCl 2N (5 mL) and extracted with EtOAc (2×5 mL). The organic extracts were dried over $Na_2SO_4$ and concentrated in vacuo to furnish the crude product, which was purified by flash chromatography eluting with cyclohexane/EtOAc (0 to 100%) to give the pure title compound as white solid (0.11 g, 45%). UPLC-MS (method A): Rt. 2.74 min (TIC); ionization ES$^+$419 [M+H]$^+$. $^1$H NMR (400 MHz, DMSO-d$_6$): δ 7.18-7.00 (m, 2H), 6.86-6.76 (m, 2H), 4.65 (t, J=4.6 Hz, 1H), 4.27-4.16 (m, 2H), 2.63 (s, 3H), 2.50-2.45 (m, 2H), 2.35 (s, 3H), 2.15-1.92 (m, 6H), 1.77-1.64 (m, 2H), 1.56-1.45 (m, 2H), 1.36-1.21 (m, 2H), 0.89 (t, J=7.3 Hz, 3H). $^{13}$C NMR (101 MHz, DMSO-d$_6$): δ 173.57, 157.74, 155.06, 134.92, 129.81, 115.86, 36.63, 34.38, 33.81, 28.57, 22.16, 14.24, 12.80, 11.01.

Example 16. (1R,3r,5S)-3-(4-Butylphenoxy)-8-[(2,5-dimethyl-3-thienyl)sulfonyl]-8-azabicyclo[3.2.1]octane Following GP4, (1R,3r,5S)-3-(4-butylphenoxy)-8-azabicyclo[3.2.1]octane trifluoroacetate (0.24 g, 1.1 eq., 0.64 mmol) was dissolved in THF (4 mL). Triethylamine (0.32 mL, 4 eq., 2.32 mmol) was then added followed by 2,5-dimethylthiophene-3-sulfonyl chloride (0.12 g, 1 eq., 0.58 mmol). The reaction mixture was stirred at room temperature for 16 h. Then it was quenched by the addition of HCl 2N (5 mL) and extracted with EtOAc (2×5 mL). The organic extracts were dried over $Na_2SO_4$ and concentrated in vacuo to furnish the crude product, which was purified by flash chromatography eluting with cyclohexane/EtOAc (0 to 100%) and then by preparative HPLC to give the pure title compound as white solid (0.01 g, 6%). UPLC-MS (method A): Rt. 3.17 min (TIC); ionization ES$^+$434 [M+H]$^+$. $^1$H NMR (400 MHz, DMSO-d$_6$): δ 7.13-7.03 (m, 2H), 6.95 (d, J=1.3 Hz, 1H), 6.83-6.71 (m, 2H), 4.64 (t, J=4.9 Hz, 1H), 4.23-4.07 (m, 2H), 2.58 (s, 3H), 2.50-2.45 (m, 2H), 2.38 (s, 3H), 2.06 (dt, J=14.8, 4.3 Hz, 2H), 2.02-1.93 (m, 4H), 1.59-1.43 (m, 4H), 1.35-1.21 (m, 2H), 0.89 (t, J=7.3 Hz, 3H). $^{13}$C NMR (101 MHz, DMSO-d$_6$): δ 155.11, 142.51, 137.02, 134.86, 134.31, 129.79, 126.12, 115.86, 69.31, 55.84, 37.02, 34.38, 33.81, 28.36, 22.17, 14.94, 14.48, 14.24.

Example 17. (1R,3r,5S)-3-(4-Ethylphenoxy)-8-[(3,5-dimethyl-1H-pyrazol-4-yl)sulfonyl]-8-azabicyclo[3.2.1]octane Following GP4, (1R,3r,5S)-3-(4-ethylphenoxy)-8-azabicyclo[3.2.1]octane trifluoroacetate (0.13 g, 1.1 eq., 0.37 mmol) was dissolved in THF (3 mL). Triethylamine (0.19 mL, 4 eq., 1.36 mmol) was then added followed by 3,5-dimethyl-1H-pyrazole-4-sulfonyl chloride (0.07 g, 1 eq., 0.34 mmol). The reaction mixture was stirred at room temperature for 16 h. Then it was quenched by the addition of HCl 2N (5 mL) and extracted with EtOAc (2×5 mL). The organic extracts were dried over $Na_2SO_4$ and concentrated in vacuo to furnish the crude product, which was purified by flash chromatography eluting with cyclohexane/EtOAc (0 to 60%) to give the pure title compound as white solid (0.08 g, 57%). UPLC-MS (method A): Rt. 2.76 min (TIC); ionization ES$^+$390 [M+H]$^+$. $^1$H NMR (400 MHz, DMSO-d$_6$): δ 12.97 (s, 1H), 7.17-7.06 (m, 2H), 6.84-6.72 (m, 2H), 4.63 (t, J=4.1 Hz, 1H), 4.15-4.04 (m, 2H), 2.57-2.52 (m, 2H), 2.37 (s, 3H), 2.28 (s, 3H), 2.09-1.92 (m, 6H), 1.67-1.58 (m, 2H), 1.14 (t, J=7.6 Hz, 3H). $^{13}$C NMR (101 MHz, DMSO-d$_6$): δ 155.14, 136.28, 129.27, 115.94, 114.95, 69.35, 55.45, 36.81, 28.40, 27.74, 26.81, 16.31, 13.49, 10.97.

Example 18. (1R,3r,5S)-3-(4-Isopropylphenoxy)-8-[(3,5-dimethyl-1H-pyrazol-4-yl)sulfonyl]-8-azabicyclo[3.2.1]octane Following GP4, (1R,3r,5S)-3-(4-isopropylphenoxy)-8-azabicyclo[3.2.1]octane trifluoroacetate (0.15 g, 1.1 eq., 0.41 mmol) was dissolved in THF (3 mL). Triethylamine (0.21 mL, 4 eq., 1.48 mmol) was then added followed by 3,5-dimethyl-1H-pyrazole-4-sulfonyl chloride (0.07 g, 1 eq., 0.37 mmol). The reaction mixture was stirred at room temperature for 16 h. Then it was quenched by the addition of HCl 2N (5 mL) and extracted with EtOAc (2×5 mL). The organic extracts were dried over $Na_2SO_4$ and concentrated in vacuo to furnish the crude product, which was purified by flash chromatography eluting with cyclohexane/EtOAc (0 to 60%) to give the pure title compound as white solid (0.09 g, 59%). UPLC-MS (method A): Rt. 2.94 min (TIC); ionization $ES^+$404 $[M+H]^+$. $^1H$ NMR (400 MHz, DMSO-$d_6$): δ 12.98 (bs, 1H), 7.20-7.07 (m, 2H), 6.83-6.68 (m, 2H), 4.63 (t, J=4.6 Hz, 1H), 4.18-3.96 (m, 2H), 2.82 (hept, J=6.9 Hz, 1H), 2.32 (bs, 6H), 2.08-1.88 (m, 6H), 1.73-1.55 (m, 2H), 1.17 (d, J=6.9 Hz, 6H). $^{13}C$ NMR (101 MHz, DMSO-$d_6$): δ 155.17, 140.94, 127.77, 115.84, 114.94, 69.32, 55.46, 36.82, 33.03, 28.40, 24.56, 16.24.

Example 19. (1R,3r,5S)-3-(4-Hexylphenoxy)-8-[(3,5-dimethyl-1H-pyrazol-4-yl)sulfonyl]-8-azabicyclo[3.2.1]octane Following GP4, (1R,3r,5S)-3-(4-hexylphenoxy)-8-azabicyclo[3.2.1]octane trifluoroacetate (0.2 g, 1.1 eq., 0.49 mmol) was dissolved in THF (3 mL). Triethylamine (0.25 mL, 4 eq., 1.8 mmol) was then added followed by 3,5-dimethyl-1H-pyrazole-4-sulfonyl chloride (0.09 g, 1 eq., 0.45 mmol). The reaction mixture was stirred at room temperature for 16 h. Then it was quenched by the addition of HCl 2N (5 mL) and extracted with EtOAc (2×5 mL). The organic extracts were dried over $Na_2SO_4$ and concentrated in vacuo to furnish the crude product, which was purified by flash chromatography eluting with cyclohexane/EtOAc (0 to 70%) to give the pure title compound as white solid (0.08 g, 40%). UPLC-MS (method A): Rt. 2.63 min (TIC); ionization $ES^+$446 $[M+H]^+$. $^1H$ NMR (400 MHz, DMSO-$d_6$): δ 12.97 (s, 1H), 7.19-7.00 (m, 2H), 6.84-6.70 (m, 2H), 4.62 (t, J=4.4 Hz, 1H), 4.21-4.01 (m, 2H), 2.50-2.46 (m, 2H), 2.37 (bs, 3H), 2.28 (bs, 3H), 2.08-1.88 (m, 6H), 1.66-1.59 (m, 2H), 1.56-1.43 (m, 2H), 1.35-1.22 (m, 6H), 0.94-0.76 (m, 3H). $^{13}C$ NMR (101 MHz, DMSO-$d_6$): δ 155.13, 134.86, 129.77, 115.85, 114.94, 69.34, 55.45, 36.83, 34.73, 31.61, 31.57, 28.77, 28.40, 22.53, 14.41, 13.48, 10.96.

Example 20. (1R,3r,5S)-3-(4-Butylphenoxy)-8-[(3-isopropyl-5-methyl-1H-pyrazol-4-yl)sulfonyl]-8-azabicyclo[3.2.1]octane Following GP4, (1R,3r,5S)-3-(4-butylphenoxy)-8-azabicyclo[3.2.1]octane trifluoroacetate (0.2 g, 1.1 eq., 0.53 mmol) was dissolved in THF (4 mL). Triethylamine (0.27 mL, 4 eq., 1.92 mmol) was then added followed by 3-isopropyl-5-methyl-1H-pyrazole-4-sulfonyl chloride (0.11 g, 1 eq., 0.58 mmol). The reaction mixture was stirred at room temperature for 16 h. Then it was quenched by the addition of HCl 2N (5 mL) and extracted with EtOAc (2×5 mL). The organic extracts were dried over $Na_2SO_4$ and concentrated in vacuo to furnish the crude product, which was purified by flash chromatography eluting with cyclohexane/EtOAc (0 to 80%) to give the pure title compound as white solid (0.06 g, 27%). UPLC-MS (method A): Rt. 2.37 min (TIC); ionization $ES^+$446 $[M+H]^+$. $^1H$ NMR (400 MHz, DMSO-$d_6$): δ 13.00 (s, 1H), 7.15-7.01 (m, 2H), 6.84-6.74 (m, 2H), 4.62 (t, J=4.5 Hz, 1H), 4.16-3.96 (m, 2H), 3.56-3.44 (m, 1H), 2.50-2.45 (m, 2H), 2.42-2.21 (m, 3H), 2.09-1.87 (m, 6H), 1.74-1.64 (m, 2H), 1.57-1.43 (m, 2H), 1.35-1.24 (m, 2H), 1.27-1.17 (m, 6H), 0.88 (t, J=7.3 Hz, 3H). $^{13}C$ NMR (101 MHz, DMSO-$d_6$): δ 155.11, 134.81, 129.78, 115.85, 111.36, 69.27, 55.42, 36.68, 34.38, 33.82, 28.52, 22.17, 14.24.

Example 21. (1R,3r,5S)-3-(2-Fluoro-4-methylphenoxy)-8-[(3,5-dimethyl-1H-pyrazol-4-yl)sulfonyl]-8-azabicyclo[3.2.1]octane Following GP4, (1R,3r,5S)-3-(2-fluoro-4-methylphenoxy)-8-azabicyclo[3.2.1]octane trifluoroacetate (0.19 g, 1.1 eq., 0.54 mmol) was dissolved in THF (3 mL). Triethylamine (0.27 mL, 4 eq., 1.96 mmol) was then added followed by 3,5-dimethyl-1H-pyrazole-4-sulfonyl chloride (0.1 g, 1 eq., 0.49 mmol). The reaction mixture was stirred at room temperature for 16 h. Then it was quenched by the addition of HCl 2N (5 mL) and extracted with EtOAc (2×5 mL). The organic extracts were dried over $Na_2SO_4$ and concentrated in vacuo to furnish the crude product, which was purified by flash chromatography eluting with cyclohexane/EtOAc (0 to 80%) to give the pure title compound as white solid (0.12 g, 63%). UPLC-MS (method A): Rt. 2.56 min (TIC); ionization $ES^+$394 $[M+H]^+$. $^1H$ NMR (400 MHz, DMSO-$d_6$): δ 12.98 (s, 1H), 7.03 (ddd, J=12.4, 2.1, 0.8 Hz, 1H), 6.97 (t, J=8.6 Hz, 1H), 6.94-6.89 (m, 1H), 4.72-4.56 (m, 1H), 4.17-4.02 (m, 2H), 2.37 (s, 3H), 2.28 (s, 3H), 2.23 (s, 3H), 2.11-1.92 (m, 6H), 1.72-1.43 (m, 2H). $^{13}C$ NMR (101 MHz, DMSO-$d_6$): δ 142.52, 131.36, 125.35, 117.39, 117.21, 116.96, 116.95, 114.90, 71.28, 55.32, 36.91, 28.29, 20.46, 13.49, 11.29.

Example 22. (1R,3r,5S)-8-[(3,5-Dimethyl-1H-pyrazol-4-yl)sulfonyl]-3-(2-quinolyloxy)-8-azabicyclo[3.2.1]octane Following GP4, (1R,3r,5S)-3-(2-quinolyloxy)-8-azabicyclo[3.2.1]octane trifluoroacetate (0.05 g, 1.1 eq., 0.15 mmol) was dissolved in THF (2 mL). Triethylamine (0.08 mL, 4 eq., 0.56 mmol) was then added followed by 3,5-dimethyl-1H-pyrazole-4-sulfonyl chloride (0.03 g, 1 eq., 0.14 mmol). The reaction mixture was stirred at room temperature for 16 h. Then it was quenched by the addition of HCl 2N (5 mL) and extracted with EtOAc (2×5 mL). The organic extracts were dried over $Na_2SO_4$ and concentrated in vacuo to furnish the crude product, which was purified by flash chromatography eluting with cyclohexane/EtOAc (0 to 80%) to give the pure title compound as white solid (0.04 g, 67%). UPLC-MS (method A): Rt. 2.64 min (TIC); ionization $ES^+$413 $[M+H]^+$. $^1H$ NMR (400 MHz, DMSO-$d_6$): δ 13.00 (s, 1H), 8.23 (d, J=8.8 Hz, 1H), 7.92-7.82 (m, 1H), 7.77-7.69 (m, 1H), 7.65 (ddd, J=8.4, 6.9, 1.5 Hz, 1H), 7.42 (ddd, J=8.1, 6.8, 1.3 Hz, 1H), 6.96 (d, J=8.8 Hz, 1H), 5.52 (t, J=4.9 Hz, 1H), 4.19-4.04 (m, 2H), 2.44-2.34 (m, 3H), 2.34-2.27 (m, 3H), 2.22-1.97 (m, 6H), 1.77-1.58 (m, 2H). $^{13}C$ NMR (101 MHz, DMSO-$d_6$): δ 166.92, 161.02, 146.30, 140.01, 130.21, 128.19, 127.15, 125.21, 124.56, 114.92, 114.01, 110.73, 67.83, 55.56, 37.57, 28.51, 13.52, 10.97.

Example 23. (1R,3r,5S)-8-[(3,5-Dimethyl-1H-pyrazol-4-yl)sulfonyl]-3-(2-benzoxazoloxy)-8-azabicyclo[3.2.1]octane Following GP4, 2-[(1R,3r,5S)-8-azabicyclo[3.2.1]octan-3-yloxy]-1,3-benzoxazole trifluoroacetate (0.06 g, 1.1 eq., 0.17 mmol) was dissolved in THF (2 mL). Triethylamine (0.08 mL, 4 eq., 0.6 mmol) was then added followed by 3,5-dimethyl-1H-pyrazole-4-sulfonyl chloride (0.03 g, 1 eq., 0.15 mmol). The reaction mixture was stirred at room temperature for 16 h. Then it was quenched by the addition of HCl 2N (5 mL) and extracted with EtOAc (2×5 mL). The organic extracts were dried over $Na_2SO_4$ and concentrated in vacuo to furnish the crude product, which was purified by flash chromatography eluting with DCM/MeOH (0 to 5%) to give the pure title compound as white solid (0.03 g, 56%). UPLC-MS (method A): Rt. 2.22 min (TIC); ionization ES$^+$403 [M+H]$^+$. $^1$H NMR (400 MHz, DMSO-d$_6$): δ 13.01 (s, 1H), 7.58-7.39 (m, 2H), 7.27 (td, J=7.6, 1.4 Hz, 1H), 7.21 (td, J=7.7, 1.5 Hz, 1H), 5.36-5.25 (m, 1H), 4.23-3.97 (m, 2H), 2.38 (s, 3H), 2.29 (s, 3H), 2.19 (d, J=2.9 Hz, 4H), 2.02-1.93 (m, 2H), 1.74-1.51 (m, 2H). $^{13}$C NMR (101 MHz, DMSO-d$_6$): δ 162.65, 148.20, 141.20, 124.77, 123.30, 118.10, 114.78, 110.28, 77.07, 55.14, 37.36, 28.20, 13.54, 11.02.

Example 24. (1R,3r,5S)-3-(4-Methoxyphenoxy)-8-[(3,5-dimethyl-1H-pyrazol-4-yl)sulfonyl]-8-azabicyclo[3.2.1]octane Following GP4, (1R,3r,5S)-3-(4-methoxyphenoxy)-8-azabicyclo[3.2.1]octane trifluoroacetate (0.09 g, 1.1 eq., 0.27 mmol) was dissolved in THF (3 mL). Triethylamine (0.14 mL, 4 eq., 1 mmol) was then added followed by 3,5-dimethyl-1H-pyrazole-4-sulfonyl chloride (0.05 g, 1 eq., 0.25 mmol). The reaction mixture was stirred at room temperature for 16 h. Then it was quenched by the addition of HCl 2N (5 mL) and extracted with EtOAc (2×5 mL). The organic extracts were dried over Na$_2$SO$_4$ and concentrated in vacuo to furnish the crude product, which was purified by flash chromatography eluting with DCM/MeOH (0 to 2%) to give the pure title compound as white solid (0.06 g, 56%). UPLC-MS (method A): Rt. 2.94 min (TIC); ionization ES$^+$404 [M+H]$^+$. $^1$H NMR (400 MHz, DMSO-d$_6$): δ 12.97 (s, 1H), 6.91-6.74 (m, 4H), 4.56 (t, J=4.4 Hz, 1H), 4.14-3.98 (m, 2H), 3.69 (s, 3H), 2.37 (s, 3H), 2.27 (s, 3H), 2.06-1.91 (m, 6H), 1.66-1.56 (m, 2H). $^{13}$C NMR (101 MHz, DMSO-d$_6$): δ 153.89, 151.02, 144.55, 117.24, 115.25, 114.94, 99.99, 70.03, 55.80, 55.46, 36.77, 28.40, 13.49, 11.00.

Example 25. (1R,3r,5S)-8-[(3,5-Dimethyl-1H-pyrazol-4-yl)sulfonyl]-3-(2-pyridiloxy)-8-azabicyclo[3.2.1]octane Following GP4, (1R,3r,5S)-3-(2-pyridyloxy)-8-azabicyclo[3.2.1]octane trifluoroacetate (0.04 g, 1.1 eq., 0.13 mmol) was dissolved in THF (2 mL). Triethylamine (0.07 mL, 4 eq., 0.48 mmol) was then added followed by 3,5-dimethyl-1H-pyrazole-4-sulfonyl chloride (0.02 g, 1 eq., 0.12 mmol). The reaction mixture was stirred at room temperature for 16 h. Then it was quenched by the addition of HCl 2N (5 mL) and extracted with EtOAc (2×5 mL). The organic extracts were dried over Na$_2$SO$_4$ and concentrated in vacuo to furnish the crude product, which was purified by flash chromatography eluting with cyclohexane/EtOAc (0 to 80%) to give the pure title compound as white solid (0.03 g, 70%). UPLC-MS (method A): Rt. 2.08 min (TIC); ionization ES$^+$363 [M+H]$^+$. $^1$H NMR (400 MHz, DMSO-d$_6$): δ 12.99 (s, 1H), 8.14 (dd, J=5.0, 2.0 Hz, 1H), 7.69 (ddd, J=8.7, 7.1, 2.1 Hz, 1H), 6.95 (dd, J=7.0, 5.0 Hz, 1H), 6.75 (d, J=8.3 Hz, 1H), 5.28 (t, J=4.8 Hz, 1H), 4.18-4.05 (m, 2H), 2.37 (s, 3H), 2.28 (s, 3H), 2.15-1.89 (m, 6H), 1.75-1.53 (m, 2H). $^{13}$C NMR (101 MHz, DMSO-d$_6$): δ 162.69, 147.31, 139.84, 117.40, 114.96, 111.88, 67.59, 55.55, 37.54, 28.43, 13.52, 10.98.

Example 26. (1R,3r,5S)-3-(4-Propoxyphenoxy)-8-[(3,5-dimethyl-1H-pyrazol-4-yl)sulfonyl]-8-azabicyclo[3.2.1]octane Following GP4, (1R,3r,5 S)-3-(4-propoxyphenoxy)-8-azabicyclo[3.2.1]octane trifluoroacetate (0.14 g, 1.1 eq., 0.37 mmol) was dissolved in THF (3 mL). Triethylamine (0.19 mL, 4 eq., 1.36 mmol) was then added followed by 3,5-dimethyl-1H-pyrazole-4-sulfonyl chloride (0.07 g, 1 eq., 0.34 mmol). The reaction mixture was stirred at room temperature for 16 h. Then it was quenched by the addition of HCl 2N (5 mL) and extracted with EtOAc (2×5 mL). The organic extracts were dried over Na$_2$SO$_4$ and concentrated in vacuo to furnish the crude product, which was purified by flash chromatography eluting with DCM/MeOH (0 to 2%) to give the pure title compound as white solid (0.08 g, 56%). UPLC-MS (method A): Rt. 2.77 min (TIC); ionization ES$^+$420 [M+H]$^+$. $^1$H NMR (400 MHz, DMSO-d$_6$): δ 12.98 (s, 1H), 7.09-6.58 (m, 4H), 4.59-4.49 (m, 1H), 4.13-4.01 (m, 2H), 3.84 (t, J=6.5 Hz, 2H), 2.32 (d, J=35.9 Hz, 6H), 2.07-1.87 (m, 6H), 1.79-1.63 (m, 2H), 1.63-1.56 (m, 2H), 0.96 (t, J=7.4 Hz, 3H). $^{13}$C NMR (101 MHz, CDCl$_3$): δ 158.05, 155.69, 121.97, 120.64, 119.69, 99.98, 74.75, 74.52, 60.21, 41.52, 33.13, 27.33, 15.63, 13.35, 10.89.

Example 27. (1R,3r,5S)-8-[(3,5-Dimethyl-1H-pyrazol-4-yl)sulfonyl]-3-[(5-methyl-2-pyridil)oxy]-8-azabicyclo[3.2.1]octane Following GP4, (1R,3r,5S)-3-[(5-methyl-2-pyridyl)oxy]-8-azabicyclo[3.2.1]octane trifluoroacetate (0.02 g, 1.1 eq., 0.06 mmol) was dissolved in THF (2 mL). Triethylamine (0.03 mL, 4 eq., 0.22 mmol) was then added followed by 3,5-dimethyl-1H-pyrazole-4-sulfonyl chloride (0.01 g, 1 eq., 0.06 mmol). The reaction mixture was stirred at room temperature for 16 h. Then it was quenched by the addition of HCl 2N (5 mL) and extracted with EtOAc (2×5 mL). The organic extracts were dried over Na$_2$SO$_4$ and concentrated in vacuo to furnish the crude product, which was purified by flash chromatography eluting with DCM/MeOH (0 to 2%) to give the pure title compound as white solid (0.02 g, 76%). UPLC-MS (method A): Rt. 2.32 min (TIC); ionization ES$^+$377 [M+H]$^+$. $^1$H NMR (400 MHz, DMSO-d$_6$): δ 12.98 (s, 1H), 8.05-7.91 (m, 1H), 7.52 (dd, J=8.4, 2.5 Hz, 1H), 6.67 (d, J=8.4 Hz, 1H), 5.28-5.17 (m, 1H), 4.10 (dt, J=5.7, 2.8 Hz, 2H), 2.37 (s, 3H), 2.28 (s, 3H), 2.19 (s, 3H), 2.11-1.98 (m, 4H), 1.98-1.89 (m, 2H), 1.70-1.54 (m, 2H). $^{13}$C NMR (101 MHz, DMSO-d$_6$): δ 160.93, 146.58, 142.68, 140.65, 134.64, 125.98, 114.95, 111.27, 67.45, 55.56, 37.49, 28.41, 17.34, 13.50, 10.97.

Example 28. (1R,3r,5S)-8-[(3,5-Dimethyl-1H-pyrazol-4-yl)sulfonyl]-3-(2-(4-methyl)-benzoxazoloxy)-8-azabicyclo[3.2.1]octane Following GP4, 2-[(1R,3r,5S)-8-azabicyclo[3.2.1]octan-3-yloxy]-4-methyl-1,3-benzoxazole trifluoroacetate (0.15 g, 1.1 eq., 0.39 mmol) was dissolved in THF (4 mL). Triethylamine (0.2 mL, 4 eq., 1.4 mmol) was then added followed by 3,5-dimethyl-1H-pyrazole-4-sulfonyl chloride (0.07 g, 1 eq., 0.35 mmol). The reaction mixture was stirred at room temperature for 16 h. Then it was quenched by the addition of HCl 2N (5 mL) and extracted with EtOAc (2×5 mL). The organic extracts were dried over Na$_2$SO$_4$ and concentrated in vacuo to furnish the crude product, which was purified by flash chromatography eluting with DCM/MeOH (0 to 5%) to give the pure title compound as white solid (0.07 g, 45%). UPLC-MS (method A): Rt. 2.54 min (TIC); ionization ES$^+$417 [M+H]$^+$. $^1$H NMR (400 MHz, DMSO-d$_6$): δ 13.03 (s, 1H), 7.37-7.28 (m, 1H), 7.15-7.05 (m, 2H), 5.34-5.27 (m, 1H), 4.16 (dd, J=5.0, 2.9 Hz, 2H), 2.42 (s, 3H), 2.41-2.36 (m, 3H), 2.30 (s, 3H), 2.19 (dd, J=3.9, 1.7 Hz, 4H), 1.98 (t, J=7.0 Hz, 2H), 1.66 (dd, J=8.1, 4.3 Hz, 2H). $^{13}$C NMR (101 MHz, DMSO-d$_6$): δ 162.12, 150.48, 147.83, 127.89, 125.41, 122.98, 107.63, 99.99, 76.85, 55.16, 37.39, 28.21, 16.54, 13.42, 11.00.

Example 29. (1R,3r,5S)-3-(4-Trifluoromethyl-phenoxy)-8-[(3,5-dimethyl-1H-pyrazol-4-yl)sulfonyl]-8-azabicyclo[3.2.1]octane Following GP4, (1R,3r,5S)-3-(4-trifluoromethyl-phenoxy)-8-azabicyclo[3.2.1]octane trifluoroacetate (0.208 g, 1.1 eq., 0.54 mmol) was dissolved in THF (3 mL). Triethylamine (0.27 mL, 4 eq., 1.96 mmol) was then added followed by 3,5-dimethyl-1H-pyrazole-4-sulfonyl chloride (0.1 g, 1 eq., 0.49 mmol). The reaction mixture was stirred at room temperature for 16 h. Then it was quenched by the addition of HCl 2N (5 mL) and extracted with EtOAc (2×5 mL). The organic extracts were dried over Na$_2$SO$_4$ and concentrated in vacuo to furnish the crude product, which was purified by flash chromatography eluting with cyclohexane/EtOAc (1:1) to give the pure title compound as a white solid (0.12 g, 54%). UPLC-MS: t$_R$=2.72 min (generic method); MS (ESI) m/z calcd for C$_{19}$H$_{23}$F$_3$N$_3$O$_3$S (M+H)$^+$: 430.1, found: 429.2. $^1$H NMR (400 MHz, DMSO-d$_6$) δ 12.98 (br s, 1H), 7.64 (d, J=8.6 Hz, 2H), 7.05 (d, J=8.6 Hz, 2H), 4.80 (app-t, J=4.8 Hz, 1H), 4.10 (br s, 2H), 2.32 (br s, 6H), 2.14-2.02 (m, 2H), 2.03-1.89 (m, 4H), 1.73-1.55 (m, 2H).

Example 30. (1R,3r,5S)-3-(4-Formyl-phenoxy)-8-[(3,5-dimethyl-1H-pyrazol-4-yl)sulfonyl]-8-azabicyclo[3.2.1]octane Following GP4, (1R,3r,5S)-3-(4-formyl-phenoxy)-8-azabicyclo[3.2.1]octane trifluoroacetate (0.186 g, 1.1 eq., 0.54 mmol) was dissolved in THF (3 mL). Triethylamine (0.27 mL, 4 eq., 1.96 mmol) was then added followed by 3,5-dimethyl-1H-pyrazole-4-sulfonyl chloride (0.1 g, 1 eq., 0.49 mmol). The reaction mixture was stirred at room temperature for 16 h. Then it was quenched by the addition of HCl 2N (5 mL) and extracted with EtOAc (2×5 mL). The organic extracts were dried over Na$_2$SO$_4$ and concentrated in vacuo to furnish the crude product, which was purified by flash chromatography eluting with cyclohexane/EtOAc (40:60) to give the pure title compound as a white solid (0.16 g, 55%). UPLC-MS: t$_R$=2.12 min (generic method); MS (ESI) m/z calcd for C$_{19}$H$_{24}$F$_3$N$_3$O$_4$S (M+H)$^+$: 390.2, found: 390.1. $^1$H NMR (400 MHz, DMSO-d$_6$) δ 12.98 (br s, 1H), 9.85 (s, 1H), 7.85 (d, J=8.7 Hz, 2H), 7.06 (d, J=8.7 Hz, 2H), 4.84 (app-t, J=4.9 Hz, 1H), 4.11 (br s, 2H), 2.32 (br s, 6H), 2.16-2.03 (m, 2H), 2.02-1.91 (m, 4H), 1.70-1.57 (m, 2H).

Example 31. (1R,3r,5S)-3-(4-Hydroxymethyl-phenoxy)-8-[(3,5-dimethyl-1H-pyrazol-4-yl)sulfonyl]-8-azabicyclo[3.2.1]octane A solution of (1R,3r,5 S)-3-(4-formyl-phenoxy)-8-[(3,5-dimethyl-1H-pyrazol-4-yl)sulfonyl]-8-azabicyclo[3.2.1]octane (0.10 g, 1.0 eq., 0.26 mmol) in MeOH (5.0 mL) was treated with NaBH$_4$ (0.025 g, 2.5 eq., 0.64 mmol) to give the title compound as a white solid (0.099 g, 98%) with no chromatographic purification. UPLC-MS: t$_R$=1.85 min (generic method); MS (ESI) m/z calcd for C$_{19}$H$_{26}$N$_3$O$_4$S (M+H)$^+$: 392.2, found: 392.2. $^1$H NMR (400 MHz, DMSO-d$_6$) δ 12.97 (br s, 1H), 7.21 (d, J=8.5 Hz, 2H), 6.81 (d, J=8.5 Hz, 2H), 5.01 (t, J=5.7 Hz, 1H), 4.65 (app-t, J=4.7 Hz, 1H), 4.39 (d, J=5.7 Hz, 2H), 4.08 (br s, 2H), 2.36 (s, 3H), 2.27 (s, 3H), 2.12-1.83 (m, 6H), 1.67-1.55 (m, 2H).

Example 33. (1R,3r,5S)-3-[4-Isopentyl-phenoxy]-8-[(3,5-dimethyl-1H-pyrazol-4-yl)sulfonyl]-8-azabicyclo[3.2.1]octane Step 1. Following GP4, (1R,3r,5S)-3-[4-[(E)-3-methylbut-1-enyl]phenoxy]-8-azabicyclo[3.2.1]octane trifluoroacetate (0.108 g, 1.1 eq., 0.28 mmol) was dissolved in THF (3 mL). Triethylamine (0.14 mL, 4 eq., 1 mmol) was then added followed by 3,5-dimethyl-1H-pyrazole-4-sulfonyl chloride (0.05 g, 1 eq., 0.25 mmol). The reaction mixture was stirred at room temperature for 16 h. Then it was quenched by the addition of HCl 2N (5 mL) and extracted with EtOAc (2×5 mL). The organic extracts were dried over Na$_2$SO$_4$ and concentrated in vacuo to furnish the crude product, which was purified by flash chromatography eluting with cyclohexane/EtOAc (40:60) to give (1R,3R,5S)-3-[4-[(E)-3-methylbut-1-enyl]phenoxy]-8-[(3,5-dimethyl-1H-pyrazol-4-yl)sulfonyl]-8-azabicyclo[3.2.1]octane as white solid (0.042 g, 38%). $^1$H NMR (400 MHz, DMSO-d$_6$) δ 12.97 (br s, 1H), 7.30 (d, J=8.7 Hz, 2H), 6.81 (d, J=8.7 Hz, 2H), 6.27 (d, J=16.0 Hz, 1H), 6.09 (dd, J=6.7, 16.0 Hz, 1H), 4.67 (app-t, J=4.2 Hz, 1H), 4.09 (br s, 2H), 2.46-2.37 (m, 1H), 2.32 (br s, 6H), 2.09-1.90 (m, 6H), 1.67-1.55 (m, 2H), 1.04 (d, J=6.7 Hz, 6H).

Step 2. To a solution of (1R,3r,5S)-3-[4-[(E)-3-methylbut-1-enyl]phenoxy]-8-[(3,5-dimethyl-1H-pyrazol-4-yl)sulfonyl]-8-azabicyclo[3.2.1]octane (0.015 g, 1.0 eq., 0.035 mmol) in EtOH (5.0 mL) were added ammonium formate (0.022 g, 10 eq., 0.35 mmol) and 10% Pd/C (ca. 3 mg). The resulting mixture was sonicated at room temperature for ca. 30 min. The suspension was then filtered and the residue concentrated to dryness. The crude product was partitioned between EtOAc and brine, dried over Na$_2$SO$_4$ and concentrated in vacuo to furnish the crude product, which was purified by flash chromatography eluting with cyclohexane/EtOAc (1:1) to give the title compound as a white solid (0.01 g, 67%). UPLC-MS: t$_R$=2.28 min (apolar method); MS (ESI) m/z calcd for C$_{23}$H$_{32}$N$_3$O$_3$S (M−H)$^-$: 430.2, found: 430.3. $^1$H NMR (400 MHz, DMSO-d$_6$) δ 12.96 (s, 1H), 7.08 (d, J=8.6 Hz, 2H), 6.76 (d, J=8.6 Hz, 2H), 4.61 (app-t, J=4.3 Hz, 1H), 4.08 (br s, 2H), 2.51-2.46 (m, 2H), 2.31 (br s, 6H), 2.08-1.87 (m, 6H), 1.66-1.56 (m, 2H), 1.55-1.46 (m, 1H), 1.45-1.36 (m, 2H), 0.89 (d, J=6.5 Hz, 6H);

Example 34. (1R,3r,5S)-8-[(3,5-Dimethyl-1H-pyrazol-4-yl)sulfonyl]-3-(2-quinoxalyloxy)-8-azabicyclo[3.2.1]octane Following GP4, (1R,3r,5S)-3-(2-quinoxalyloxy)-8-azabicyclo[3.2.1]octane trifluoroacetate (0.1 g, 1.1 eq., 0.28 mmol) was dissolved in THF (3 mL). Triethylamine (0.14 mL, 4 eq., 1 mmol) was then added followed by 3,5-dimethyl-1H-pyrazole-4-sulfonyl chloride (0.05 g, 1 eq., 0.25 mmol). The reaction mixture was stirred at room temperature for 16 h. Then it was quenched by the addition of HCl 2N (5 mL) and extracted with EtOAc (2×5 mL). The organic extracts were dried over Na$_2$SO$_4$ and concentrated in vacuo to furnish the crude product, which was purified by flash chromatography eluting with DCM/MeOH (0 to 2%) to give the pure title compound as white solid (0.04 g, 39%). UPLC-MS (method A): Rt. 2.36 min (TIC); ionization ES$^+$414 [M+H]$^+$. $^1$H NMR (400 MHz, DMSO-d$_6$): δ 13.00 (s, 1H), 8.56 (s, 1H), 8.01 (dd, J=8.1, 1.4 Hz, 1H), 7.81 (dd, J=8.3, 1.5 Hz, 1H), 7.75 (ddd, J=8.3, 6.8, 1.5 Hz, 1H), 7.64

(ddd, J=8.3, 6.9, 1.6 Hz, 1H), 5.51 (t, J=4.9 Hz, 1H), 4.19-4.11 (m, 2H), 2.40 (s, 3H), 2.30 (s, 3H), 2.19 (dt, J=15.0, 4.4 Hz, 2H), 2.16-2.01 (m, 4H), 1.75-1.63 (m, 2H). $^{13}$C NMR (101 MHz, DMSO-d$_6$): δ 156.50, 147.86, 140.90, 140.00, 138.74, 130.88, 129.11, 127.31, 127.20, 114.88, 99.97, 69.16, 55.46, 37.36, 28.48, 13.52, 10.99.

Example 35. (1R,3r,5S)-3-(4-Ethoxymethyl-phenoxy)-8-[(3,5-dimethyl-1H-pyrazol-4-yl)sulfonyl]-8-azabicyclo[3.2.1]octane A solution of (1R,3r,5S)-3-(4-hydroxymethyl-phenoxy)-8-[(3,5-dimethyl-1H-pyrazol-4-yl)sulfonyl]-8-azabicyclo[3.2.1]octane (0.16 g, 1.0 eq., 0.41 mmol) in EtOH (3.0 mL) was treated with Amberlist-15® (1.0 eq.). The reaction was left at reflux for 16 h. Upon completion of the reaction, the solution was filtered and the solvent evaporated to give the title compound as a white solid (0.110 g, 64%). UPLC-MS: $t_R$=2.25 min (generic method); MS (ESI) m/z calcd for $C_{21}H_{30}N_3O_4S$ (M+H)$^+$: 420.2, found: 420.1. $^1$H NMR (400 MHz, DMSO-d$_6$) δ 12.96 (br s, 1H), 7.22 (d, J=8.6 Hz, 2H), 6.83 (d, J=8.6 Hz, 2H), 4.66 (app-t, J=4.8 Hz, 1H), 4.34 (s, 2H), 4.08 (br s, 2H), 3.43 (q, J=7.0 Hz, 2H), 2.31 (br s, 6H), 2.13-1.80 (m, 6H), 1.67-1.52 (m, 2H), 1.12 (t, J=7.0 Hz, 3H).

Example 36. (1R,3r,5S)-8-[(3,5-Dimethyl-1H-pyrazol-4-yl)sulfonyl]-3-(5-methylpyrazin-2-yl)oxy-8-azabicyclo[3.2.1]octane Following GP4, (1R,3r,5S)-3-(5-methylpyrazin-2-yl)oxy-8-azabicyclo[3.2.1]octane trifluoroacetate (0.07 g, 1.1 eq., 0.22 mmol) was dissolved in THF (3 mL). Triethylamine (0.11 mL, 4 eq., 0.8 mmol) was then added followed by 3,5-dimethyl-1H-pyrazole-4-sulfonyl chloride (0.04 g, 1 eq., 0.2 mmol). The reaction mixture was stirred at room temperature for 16 h. Then it was quenched by the addition of HCl 2N (5 mL) and extracted with EtOAc (2×5 mL). The organic extracts were dried over Na$_2$SO$_4$ and concentrated in vacuo to furnish the crude product, which was purified by flash chromatography eluting with DCM/MeOH (0 to 2%) to give the pure title compound as white solid (0.06 g, 78%). UPLC-MS (method A): Rt. 1.97 min (TIC); ionization ES$^+$378 [M+H]$^+$. $^1$H NMR (400 MHz, DMSO-d$_6$): δ 12.97 (bs, 1H), 8.14 (d, J=1.3 Hz, 1H), 8.09-7.99 (m, 1H), 5.23 (t, J=5.0 Hz, 1H), 4.18-4.06 (m, 2H), 2.38 (s, 3H), 2.33 (bs, 6H), 2.09 (dt, J=15.0, 4.4 Hz, 2H), 2.05-1.99 (m, 2H), 1.95 (dd, J=15.1, 2.3 Hz, 2H), 1.71-1.59 (m, 2H). $^{13}$C NMR (101 MHz, DMSO-d$_6$): δ 157.51, 145.36, 139.77, 134.77, 114.91, 68.63, 55.45, 37.34, 28.43, 20.20, 13.95, 11.26.

Example 37. (1R,3r,5S)-8-[(3,5-Dimethyl-1H-pyrazol-4-yl)sulfonyl]-3-pyridazin-3-yloxy-8-azabicyclo[3.2.1]octane Following GP4, (1R,3r,5S)-3-pyridazin-3-yloxy-8-azabicyclo[3.2.1]octane trifluoroacetate (0.06 g, 1.1 eq., 0.19 mmol) was dissolved in THF (3 mL). Triethylamine (0.1 mL, 4 eq., 0.68 mmol) was then added followed by 3,5-dimethyl-1H-pyrazole-4-sulfonyl chloride (0.03 g, 1 eq., 0.17 mmol). The reaction mixture was stirred at room temperature for 16 h. Then it was quenched by the addition of HCl 2N (5 mL) and extracted with EtOAc (2×5 mL). The organic extracts were dried over Na$_2$SO$_4$ and concentrated in vacuo to furnish the crude product, which was purified by flash chromatography eluting with DCM/MeOH (0 to 2%) to give the pure title compound as white solid (0.02 g, 40%). UPLC-MS (method A): Rt. 1.62 min (TIC); ionization ES$^+$364 [M+H]$^+$. $^1$H NMR (400 MHz, DMSO-d$_6$): δ 8.87 (dd, J=4.4, 1.3 Hz, 1H), 7.61 (dd, J=8.9, 4.5 Hz, 1H), 7.17 (dd, J=8.9, 1.3 Hz, 1H), 5.49 (t, J=4.9 Hz, 1H), 4.17-4.08 (m, 2H), 2.34 (s, 6H), 2.19-2.08 (m, 2H), 2.08-1.97 (m, 4H), 1.68-1.60 (m, 2H). $^{13}$C NMR (101 MHz, DMSO-d$_6$): δ 164.22, 147.95, 130.58, 118.09, 69.33, 55.45, 37.41, 28.45, 12.26.

Example 38. (1R,3r,5S)-8-[(3,5-Dimethyl-1H-pyrazol-4-yl)sulfonyl]-3-(2-(5-methyl)-benzoxazoloxy)-8-azabicyclo[3.2.1]octane Following GP4, 2-[(1R,3r,5S)-8-azabicyclo[3.2.1]octan-3-yloxy]-5-methyl-1,3-benzoxazole trifluoroacetate (0.06 g, 1.1 eq., 0.17 mmol) was dissolved in THF (2 mL). Triethylamine (0.08 mL, 4 eq., 0.6 mmol) was then added followed by 3,5-dimethyl-1H-pyrazole-4-sulfonyl chloride (0.03 g, 1 eq., 0.15 mmol). The reaction mixture was stirred at room temperature for 16 h. Then it was quenched by the addition of HCl 2N (5 mL) and extracted with EtOAc (2×5 mL). The organic extracts were dried over Na$_2$SO$_4$ and concentrated in vacuo to furnish the crude product, which was purified by flash chromatography eluting with DCM/MeOH (0 to 5%) to give the pure title compound as white solid (0.03 g, 44%). UPLC-MS (method A): Rt. 2.49 min (TIC); ionization ES$^+$417 [M+H]$^+$. $^1$H NMR (400 MHz, DMSO-d$_6$): δ 13.02 (bs, 1H), 7.38 (d, J=8.2 Hz, 1H), 7.30 (s, 1H), 7.02 (d, 1H), 5.30-5.22 (m, 1H), 4.20-4.05 (m, 2H), 2.37 (s, 3H), 2.34 (s, 6H), 2.24-2.11 (m, 4H), 2.02-1.90 (m, 2H), 1.70-1.60 (m, 2H). $^{13}$C NMR (101 MHz, DMSO-d$_6$): δ 162.74, 146.34, 141.31, 134.04, 123.92, 118.26, 114.79, 111.21, 109.70, 99.97, 76.91, 55.14, 37.38, 28.21, 21.51, 11.05.

Example 39. (1R,3r,5S)-3-(4-Chloro-phenoxy)-8-[(3,5-dimethyl-1H-pyrazol-4-yl)sulfonyl]-8-azabicyclo[3.2.1]octane Following GP4, (1R,3r,5S)-3-(4-chloro-phenoxy)-8-azabicyclo[3.2.1]octane trifluoroacetate (0.328 g, 1.1 eq., 0.94 mmol) was dissolved in THF (5 mL). Triethylamine (0.47 mL, 4 eq., 3.4 mmol) was then added followed by 3,5-dimethyl-1H-pyrazole-4-sulfonyl chloride (0.166 g, 1 eq., 0.85 mmol). The reaction mixture was stirred at room temperature for 16 h. Then it was quenched by the addition of HCl 2N (5 mL) and extracted with EtOAc (2×5 mL). The organic extracts were dried over Na$_2$SO$_4$ and concentrated in vacuo to furnish the crude product, which was purified by flash chromatography eluting with cyclohexane/EtOAc (1:1) to give the pure title compound as a white solid (0.84 g, 25%). UPLC-MS: $t_R$=1.17 min (apolar method); MS (ESI) m/z calcd for $C_{18}H_{23}ClN_3O_3S$ (M+H)$^+$: 396.1, found: 396.1. $^1$H NMR (400 MHz, DMSO-d$_6$) δ 12.96 (s, 1H), 7.31 (d, J=8.9 Hz, 2H), 6.89 (d, J=8.9 Hz, 2H), 4.66 (app-t, J=4.8 Hz, 1H), 4.08 (br s, 2H), 2.36 (s, 3H), 2.26 (s, 3H), 2.08-1.89 (m, 6H), 1.67-1.56 (m, 2H);

Example 40. (1R,3r,5S)-8-[(3,5-Dimethyl-1H-pyrazol-4-yl)sulfonyl]-3-[5-butylpyrazin-2-yl]oxy-8-azabicyclo[3.2.1]octane Following GP4, (1R,3r,5S)-3-[5-butyl-pyrazin-2-yl]oxy-8-azabicyclo[3.2.1]octane trifluoroacetate (0.041 g, 1.1 eq., 0.11 mmol) was dissolved in THF (1 mL). Triethylamine (0.056 mL, 4 eq., 0.4 mmol) was then added followed by 3,5-dimethyl-1H-pyrazole-4-sulfonyl chloride (0.02 g, 1 eq., 0.10 mmol). The reaction mixture was stirred at room temperature for 16 h. Then it was quenched by the addition of HCl 2N (5 mL) and extracted with EtOAc (2×5 mL). The organic extracts were dried over $Na_2SO_4$ and concentrated in vacuo to furnish the crude product, which was purified by flash chromatography eluting with DCM/MeOH (95:5) to give the pure title compound as white solid (0.021 g, 51%). UPLC-MS: $t_R$=2.39 min (generic method); MS (ESI) m/z calcd for $C_{20}H_{30}N_5O_3S$ $(M+H)^+$: 420.2, found: 420.2. $^1H$ NMR (400 MHz, DMSO-$d_6$) δ 12.97 (s, 1H), 8.15 (d, J=1.4 Hz, 1H), 8.04 (d, J=1.4 Hz, 1H), 5.23 (app-t, J=5.0 Hz, 1H), 4.11 (br s, 2H), 2.66 (t, J=7.4 Hz, 2H), 2.37 (br s, 3H), 2.27 (br s, 3H), 2.14-1.90 (m, 6H), 1.68-1.54 (m, 4H), 1.35-1.21 (m, 2H), 0.88 (t, J=7.3 Hz, 3H).

Example 41. (1R,3r,5S)-8-[(3,5-Dimethyl-1H-pyrazol-4-yl)sulfonyl]-3-[5-(ethoxymethyl)pyrazin-2-yl]oxy-8-azabicyclo[3.2.1]octane Following GP4, (1R,3r,5S)-3-[5-(ethoxymethyl)pyrazin-2-yl]oxy-8-azabicyclo[3.2.1]octane trifluoroacetate (0.01 g, 1.1 eq., 0.03 mmol) was dissolved in THF (1 mL). Triethylamine (0.02 mL, 4 eq., 0.12 mmol) was then added followed by 3,5-dimethyl-1H-pyrazole-4-sulfonyl chloride (0.01 g, 1 eq., 0.03 mmol). The reaction mixture was stirred at room temperature for 16 h. Then it was quenched by the addition of HCl 2N (5 mL) and extracted with EtOAc (2×5 mL). The organic extracts were dried over $Na_2SO_4$ and concentrated in vacuo to furnish the crude product, which was purified by flash chromatography eluting with DCM/MeOH (0 to 2%) to give the pure title compound as white solid (0.01 g, 55%). UPLC-MS (method A): Rt. 1.93 min (TIC); ionization $ES^+422$ $[M+H]^+$. $^1H$ NMR (400 MHz, DMSO-$d_6$): δ 12.94 (s, 1H), 8.21 (d, J=1.4 Hz, 1H), 8.19 (s, 1H), 5.28 (t, J=4.9 Hz, 1H), 4.48 (s, 2H), 4.16-4.08 (m, 2H), 3.53 (q, J=7.0 Hz, 2H), 2.33 (s, 6H), 2.15-2.06 (m, 2H), 2.07-2.01 (m, 2H), 2.00-1.93 (m, 2H), 1.72-1.59 (m, 2H), 1.15 (t, J=7.0 Hz, 3H).

Example 42. (1R,3r,5S)-3-(4-Fluoro-phenoxy)-8-[(3,5-dimethyl-1H-pyrazol-4-yl)sulfonyl]-8-azabicyclo[3.2.1]octane Following GP4, (1R,3r,5S)-3-(4-fluoro-phenoxy)-8-azabicyclo[3.2.1]octane trifluoroacetate (0.314 g, 1.1 eq., 0.94 mmol) was dissolved in THF (5 mL). Triethylamine (0.47 mL, 4 eq., 3.4 mmol) was then added followed by 3,5-dimethyl-1H-pyrazole-4-sulfonyl chloride (0.166 g, 1 eq., 0.85 mmol). The reaction mixture was stirred at room temperature for 16 h. Then it was quenched by the addition of HCl 2N (5 mL) and extracted with EtOAc (2×5 mL). The organic extracts were dried over $Na_2SO_4$ and concentrated in vacuo to furnish the crude product, which was purified by flash chromatography eluting with cyclohexane/EtOAc (1:1) to give the pure title compound as a white solid (0.099 g, 31%). UPLC-MS: $t_R$=0.93 min (apolar method); MS (ESI) m/z calcd for $C_{18}H_{23}FN_3O_3S$ $(M+H)^+$: 380.1, found: 380.2. $^1H$ NMR (400 MHz, DMSO-$d_6$) δ 12.97 (s, 1H), 7.15-7.05 (m, 2H), 6.92-6.84 (m, 2H), 4.62 (app-t, J=4.8 Hz, 1H), 4.08 (br s, 2H), 2.31 (br s, 6H), 2.08-1.87 (m, 6H), 1.70-1.52 (m, 2H).

Example 43. (1R,3s,5S)-8-[(3,5-Dimethyl-1H-pyrazol-4-yl)sulfonyl]-3-pyridazin-3-yloxy-8-azabicyclo[3.2.1]octane Following GP4, (1R,3s,5S)-3-pyridazin-3-yloxy-8-azabicyclo[3.2.1]octane trifluoroacetate (0.06 g, 1.1 eq., 0.19 mmol) was dissolved in THF (3 mL). Triethylamine (0.1 mL, 4 eq., 0.68 mmol) was then added followed by 3,5-dimethyl-1H-pyrazole-4-sulfonyl chloride (0.03 g, 1 eq., 0.17 mmol). The reaction mixture was stirred at room temperature for 16 h. Then it was quenched by the addition of HCl 2N (5 mL) and extracted with EtOAc (2×5 mL). The organic extracts were dried over $Na_2SO_4$ and concentrated in vacuo to furnish the crude product, which was purified by flash chromatography eluting with DCM/MeOH (95:5) to give the pure title compound as white solid (0.041 g, 66%). UPLC-MS: $t_R$=1.63 min (generic method); MS (ESI) m/z calcd for $C_{16}H_{22}N_5O_3S$ $(M+H)^+$: 364.1, found: 364.2. $^1H$ NMR (400 MHz, DMSO-$d_6$) δ 12.98 (br s, 1H), 8.24 (d, J=1.0 Hz, 1H), 8.20-8.17 (m, 2H), 5.33 (tt, J=6.1, 11.2 Hz, 1H), 4.19 (br s, 2H), 2.33 (br s, 6H), 2.27-2.16 (m, 2H), 1.79-1.60 (m, 6H).

Example 44. (1R,3r,5S)-9-[(3,5-Dimethyl-1H-pyrazol-4-yl)sulfonyl]-3-(pyrazin-2-yloxy)-9-azabicyclo[3.3.1]nonane Following GP4, (1R,3r,5S)-3-(pyrazin-2-yloxy)-9-azabicyclo[3.3.1]nonane trifluoroacetate (0.09 g, 1.1 eq., 0.28 mmol) was dissolved in THF (3 mL). Triethylamine (0.14 mL, 4 eq., 1 mmol) was then added followed by 3,5-dimethyl-1H-pyrazole-4-sulfonyl chloride (0.05 g, 1 eq., 0.25 mmol). The reaction mixture was stirred at room temperature for 16 h. Then it was quenched by the addition of HCl 2N (5 mL) and extracted with EtOAc (2×5 mL). The organic extracts were dried over $Na_2SO_4$ and concentrated in vacuo to furnish the crude product, which was purified by flash chromatography eluting with DCM/MeOH (0 to 2%) to give the pure title compound as white solid (0.02 g, 19%). UPLC-MS (method A): Rt. 1.98 min (TIC); ionization $ES^+378$ $[M+H]^+$. $^1H$ NMR (400 MHz, DMSO-$d_6$): δ 12.95 (s, 1H), 8.29-8.15 (m, 3H), 5.00-4.84 (m, 1H), 4.20-4.07 (m, 2H), 2.46-2.12 (m, 9H), 1.65-1.41 (m, 7H). $^{13}C$ NMR (101 MHz, DMSO-$d_6$): δ 159.34, 141.28, 138.91, 137.20, 135.97, 134.28, 116.09, 67.64, 46.63, 31.28, 30.29, 14.12, 13.44, 10.98.

Example 45. (1R,3s,5S)-9-[(3,5-Dimethyl-1H-pyrazol-4-yl)sulfonyl]-3-(pyrazin-2-yloxy)-9-azabicyclo[3.3.1]nonane Following GP4, (1R,3s,5S)-3-(pyrazin-2-yloxy)-9-azabicyclo[3.3.1]nonane trifluoroacetate (0.06 g, 1.1 eq., 0.17 mmol) was dissolved in THF (2 mL). Triethylamine (0.08 mL, 4 eq., 0.6 mmol) was then added followed by 3,5-dimethyl-1H-pyrazole-4-sulfonyl chloride (0.03 g, 1 eq., 0.15 mmol). The reaction mixture was stirred at room temperature for 16 h. Then it was quenched by the addition of HCl 2N (5 mL) and extracted with EtOAc (2×5 mL). The organic extracts were dried over $Na_2SO_4$ and concentrated in vacuo to furnish the crude product, which was purified by flash chromatography eluting with DCM/MeOH (0 to 2%) to give the pure title compound as white solid (0.02 g, 36%). UPLC-MS (method A): Rt. 2.00 min (TIC); ionization $ES^+378$ $[M+H]^+$. $^1H$ NMR (400 MHz, DMSO-$d_6$): δ 12.87 (bs, 1H), 8.57-7.90 (m, 3H), 5.89 (ddt, J=17.5, 11.5, 6.5 Hz, 1H), 4.08 (dd, J=5.3, 2.9 Hz, 2H), 2.32 (s, 6H), 2.21 (dd, J=12.9, 6.5 Hz, 2H), 1.91-1.54 (m, 8H). $^{13}C$ NMR (101 MHz, DMSO-$d_6$): δ 159.50, 141.21, 137.20, 136.12, 115.39, 99.98, 69.20, 48.56, 35.48, 29.30, 20.34, 12.06.

Example 46. (1R,3s,5S)-9-[(3,5-Dimethyl-1H-pyrazol-4-yl)sulfonyl]-7-pyrazin-2-yloxy-3-oxa-9-azabicyclo[3.3.1]nonane Following GP4, (1R,3s,5S)-7-pyrazin-2-yloxy-3-oxa-9-azabicyclo[3.3.1]nonane trifluoroacetate (0.14 g, 1.1 eq., 0.42 mmol) was dissolved in THF (3 mL). Triethylamine (0.21 mL, 4 eq., 1.52 mmol) was then added followed by 3,5-dimethyl-1H-pyrazole-4-sulfonyl chloride (0.07 g, 1 eq., 0.38 mmol). The reaction mixture was stirred at room temperature for 16 h. Then it was quenched by the addition of HCl 2N (5 mL) and extracted with EtOAc (2×5 mL). The organic extracts were dried over $Na_2SO_4$ and concentrated in vacuo to furnish the crude product, which was purified by flash chromatography eluting with DCM/MeOH (0 to 4%) to give the pure title compound as white solid (0.02 g, 17%). UPLC-MS (method A): Rt. 1.72 min (TIC); ionization ES$^+$380 [M+H]$^+$. $^1$H NMR (400 MHz, DMSO-d$_6$): δ 13.05 (s, 1H), 8.24 (d, J=1.3 Hz, 1H), 8.22-8.13 (m, 2H), 6.18-6.02 (m, 1H), 3.98-3.87 (m, 2H), 3.82 (d, J=11.4 Hz, 2H), 3.57 (dt, J=11.4, 2.2 Hz, 2H), 2.42-2.19 (m, 8H), 1.93-1.70 (m, 2H). $^{13}$C NMR (101 MHz, DMSO-d$_6$): δ 159.59, 141.19, 137.15, 136.11, 123.51, 114.72, 99.98, 70.63, 69.30, 50.22, 34.41, 13.41, 10.97.

Example 47. (1R,3r,5S)-9-[(3,5-Dimethyl-1H-pyrazol-4-yl)sulfonyl]-7-pyrazin-2-yloxy-3-oxa-9-azabicyclo[3.3.1]nonane Following GP4, (1R,3r,5S)-7-pyrazin-2-yloxy-3-oxa-9-azabicyclo[3.3.1]nonane trifluoroacetate (0.15 g, 1.1 eq., 0.44 mmol) was dissolved in THF (3 mL). Triethylamine (0.22 mL, 4 eq., 1.60 mmol) was then added followed by 3,5-dimethyl-1H-pyrazole-4-sulfonyl chloride (0.08 g, 1 eq., 0.40 mmol). The reaction mixture was stirred at room temperature for 16 h. Then it was quenched by the addition of HCl 2N (5 mL) and extracted with EtOAc (2×5 mL). The organic extracts were dried over $Na_2SO_4$ and concentrated in vacuo to furnish the crude product, which was purified by flash chromatography eluting with DCM/MeOH (0 to 4%) and then by preparative HPLC to give the pure title compound as white solid (0.02 g, 10%). UPLC-MS (method A): Rt. 1.62 min (TIC); ionization ES$^+$380 [M+H]$^+$. $^1$H NMR (400 MHz, DMSO-d$_6$): δ 8.41-7.98 (m, 3H), 5.01 (q, J=6.6 Hz, 1H), 3.91 (d, J=8.5 Hz, 2H), 3.64 (d, J=11.1 Hz, 2H), 3.47 (dd, J=11.2, 2.4 Hz, 2H), 2.45-2.35 (m, 2H), 2.33 (s, 6H), 1.86-1.73 (m, 2H). $^{13}$C NMR (101 MHz, DMSO-d$_6$): δ 159.54, 145.18, 141.20, 136.98, 136.14, 130.24, 115.33, 70.69, 67.54, 47.77, 31.06, 12.25.

Example 48. (1R,5S,9r)-7-((3,5-Dimethyl-1H-pyrazol-4-yl)sulfonyl)-9-(pyrazin-2-yloxy)-3-oxa-7-azabicyclo[3.3.1]nonane Step 1. To a solution of (1R,5S)-7-benzyl-9-pyrazin-2-yloxy-3-oxa-7-azabicyclo[3.3.1]nonane (0.9 g, 1.0 eq., 2.89 mmol) in EtOH (15.0 mL) were added ammonium formate (1.82 g, 10 eq., 28.9 mmol) and 10% Pd/C (ca. 90 mg). The resulting mixture was left at room temperature for 3 h. The suspension was then filtered and the residue concentrated to dryness. The crude product was partitioned between EtOAc and brine, dried over $Na_2SO_4$ and concentrated in vacuo to furnish (1R,5S)-9-pyrazin-2-yloxy-3-oxa-7-azabicyclo[3.3.1]nonane (0.40 g, 63%), as a yellow oil, as a ca. 1:1 mixture of two stereoisomers, which was used in the next step without any further purification.

Step 2. Following a slight modification of GP4, (1R,5S)-9-pyrazin-2-yloxy-3-oxa-7-azabicyclo[3.3.1]nonane (0.10 g, 1 eq., 0.45 mmol) was dissolved in dry DCM (5 mL). Triethylamine (0.252 mL, 4 eq., 1.80 mmol) was then added followed by 3,5-dimethyl-1H-pyrazole-4-sulfonyl chloride (0.106 g, 1.2 eq., 0.54 mmol). The reaction mixture was stirred at room temperature for 16 h. Then it was quenched by the addition of HCl 2N (5 mL) and extracted with EtOAc (2×5 mL). The organic extracts were dried over $Na_2SO_4$ and concentrated in vacuo to furnish the crude product, which was purified by flash chromatography eluting with cyclohexane/EtOAc (1:9) to give a ca 1:1 mixture of stereoisomers. The stereoisomeric mixture was then further purified by preparative HPLC to afford the pure title compound as white solid (0.017 g, 10%). UPLC-MS: t$_R$=1.55 min (generic method); MS (ESI) m/z calcd for $C_{16}H_{22}N_5O_4S$ (M+H)$^+$: 380.1, found: 380.1. $^1$H NMR (400 MHz, DMSO-d$_6$) δ 8.39 (d, J=1.4 Hz, 1H), 8.22 (d, J=2.8 Hz, 1H), 8.17 (dd, J=1.4, 2.8 Hz, 1H), 5.03 (t, J=3.5 Hz, 1H), 3.99-3.92 (m, 2H), 3.83-3.75 (m, 2H), 3.75-3.68 (m, 2H), 2.94-2.84 (m, 2H), 2.33 (s, 6H), 2.06 (br s, 2H).

Example 49. (1R,5S,9s)-7-((3,5-Dimethyl-1H-pyrazol-4-yl)sulfonyl)-9-(pyrazin-2-yloxy)-3-oxa-7-azabicyclo[3.3.1]nonane After preparative HPLC the pure title compound was isolated as white solid (0.022 g, 13%). UPLC-MS: t$_R$=1.52 min (generic method); MS (ESI) m/z calcd for $C_{16}H_{22}N_5O_4S$ (M+H)$^+$: 380.1, found: 380.1. $^1$H NMR (400 MHz, DMSO-d$_6$) δ 8.24-8.18 (m, 2H), 8.14 (d, J=1.3 Hz, 1H), 5.21 (t, J=3.6 Hz, 1H), 4.00-3.91 (m, 2H), 3.78-3.70 (m, 2H), 3.59-3.49 (m, 2H), 3.06-2.96 (m, 2H), 2.31 (s, 6H), 2.17 (br s, 2H).

Example 50. (1R,5S,8r)-3-((3,5-Dimethyl-1H-pyrazol-4-yl)sulfonyl)-8-(pyrazin-2-yloxy)-3-azabicyclo[3.2.1]octane Step 1. To a solution of (1R,5S,8r)-3-benzyl-8-pyrazin-2-yloxy-3-azabicyclo[3.2.1]octane (0.08 g, 1.0 eq., 0.27 mmol) in EtOH (5.0 mL) were added ammonium formate (0.171 g, 10 eq., 2.7 mmol) and 10% Pd/C (ca. 10 mg). The resulting mixture was left at room temperature for 3 h. The suspension was then filtered and the residue concentrated to dryness. The crude product was partitioned between EtOAc and brine, dried over $Na_2SO_4$ and concentrated in vacuo to furnish (1R,5S,8r)-8-pyrazin-2-yloxy-3-azabicyclo[3.2.1]octane (0.02 g, 36%), as a colorless oil, which was used in the next step without any further purification. UPLC-MS: t$_R$=0.99 min (generic method); MS (ESI) m/z calcd for $C_{11}H_{16}N_3O$ (M+H)$^+$: 206.1, found: 206.1.

Step 2. Following a slight modification of GP4, (1R,5S,8r)-8-pyrazin-2-yloxy-3-azabicyclo[3.2.1]octane (0.12 g, 1.0 eq., 0.58 mmol) was dissolved in dry DCM (5 mL). Triethylamine (0.32 mL, 4 eq., 2.34 mmol) was then added followed by 3,5-dimethyl-1H-pyrazole-4-sulfonyl chloride (0.135 g, 1.2 eq., 0.69 mmol). The reaction mixture was stirred at room temperature for 16 h. Then it was quenched by the addition of HCl 2N (5 mL) and extracted with EtOAc (2×5 mL). The organic extracts were dried over $Na_2SO_4$ and concentrated in vacuo to furnish the crude product, which was purified by flash chromatography eluting with DCM/MeOH (95:5) to afford the pure title compound as white solid (0.12 g, 57%). UPLC-MS: t$_R$=1.75 min (generic method); MS (ESI) m/z calcd for $C_{16}H_{22}N_5O_3S$ (M+H)$^+$: 364.1, found: 364.1. $^1$H NMR (400 MHz, DMSO-d$_6$) δ 13.02 (br s, 1H), 8.23-8.18 (m, 2H), 8.15 (d, J=1.3 Hz, 1H), 4.93 (t, J=4.9 Hz, 1H), 3.20 (dd, J=11.1, 3.4 Hz, 2H), 2.92 (d, J=10.8 Hz, 2H), 2.46 (br s, 2H), 2.40-2.17 (m, 6H), 1.83-1.72 (m, 2H), 1.65-1.55 (m, 2H).

Example 51. (1R,5S,9r)-3-((3,5-Dimethyl-1H-pyrazol-4-yl)sulfonyl)-9-(pyrazin-2-yloxy)-3-azabicyclo[3.3.1]nonane Following a slight modification of GP4, (1R,5S,9r)-9-pyrazin-2-yloxy-3-azabicyclo[3.3.1]nonane trifluoroacetate (0.336 g, 1 eq., 0.75 mmol) was dissolved in dry DCM (10 mL). Triethylamine (0.42 mL, 4 eq., 3.0 mmol) was then added followed by 3,5-dimethyl-1H-pyrazole-4-sulfonyl chloride (0.175 g, 1.2 eq., 0.54 mmol). The reaction mixture was stirred at room temperature for 16 h. Then it was quenched by the addition of HCl 2N (5 mL) and extracted with EtOAc (2×5 mL). The organic extracts were dried over $Na_2SO_4$ and concentrated in vacuo to furnish the crude product, which was purified by flash chromatography eluting with cyclohexane/EtOAc (2:8) to give a ca 7:3 mixture of stereoisomers. The stereoisomeric mixture was further purified by preparative HPLC to afford the pure title compound (syn stereoisomer) (0.018 g, 6%) as white solid. UPLC-MS: $t_R$=1.87 min (generic method); MS (ESI) m/z calcd for $C_{17}H_{24}N_5O_3S$ (M+H)$^+$: 378.2, found: 378.1. $^1$H NMR (400 MHz, DMSO-d$_6$) δ 8.18 (br s, 2H), 8.15 (br s, 1H), 4.96 (t, J=3.4 Hz, 1H), 3.55-3.45 (m, 2H), 2.95-2.84 (m, 2H), 2.31 (s, 6H), 2.28-2.15 (m, 3H), 1.97-1.87 (m, 2H), 1.86-1.74 (m, 2H), 1.46-1.35 (m, 1H).

Example 52. (1R,5S,9s)-3-((3,5-Dimethyl-1H-pyrazol-4-yl)sulfonyl)-9-(pyrazin-2-yloxy)-3-azabicyclo[3.3.1]nonane After preparative HPLC the pure title compound (anti stereoisomer) was isolated (0.015 g, 5%) as white solid. UPLC-MS: $t_R$=1.88 min (generic method); MS (ESI) m/z calcd for $C_{17}H_{24}N_5O_3S$ (M+H)$^+$: 378.2, found: 378.1. $^1$H NMR (400 MHz, DMSO-d$_6$) δ 8.34 (d, J=1.4 Hz, 1H), 8.19 (d, J=2.7 Hz, 1H), 8.14 (dd, J=2.7, 1.4 Hz, 1H), 4.93 (t, J=3.6 Hz, 1H), 3.78-3.67 (m, 2H), 2.81-2.72 (m, 2H), 2.40-2.25 (m, 7H), 2.18 (br s, 2H), 2.03-1.89 (m, 2H), 1.69-1.57 (m, 2H), 1.50-1.39 (m, 1H).

Example 53. (1R,3r,5S)-8-[(3,5-Dimethyl-1H-pyrazol-4-yl)sulfonyl]-3-(6-methylpyridazin-3-yl)oxy-8-azabicyclo[3.2.1]octane Following GP4, (1R,3r,5S)-3-(6-methylpyridazin-3-yl)oxy-8-azabicyclo[3.2.1]octane trifluoroacetate (0.05 g, 1.1 eq., 0.14 mmol) was dissolved in THF (2 mL). Triethylamine (0.07 mL, 4 eq., 0.22 mmol) was then added followed by 3,5-dimethyl-1H-pyrazole-4-sulfonyl chloride (0.03 g, 1 eq., 0.13 mmol). The reaction mixture was stirred at room temperature for 16 h. Then it was quenched by the addition of HCl 2N (5 mL) and extracted with EtOAc (2×5 mL). The organic extracts were dried over $Na_2SO_4$ and concentrated in vacuo to furnish the crude product, which was purified by flash chromatography eluting with DCM/MeOH (0 to 2%) to give the pure title compound as white solid (0.03 g, 56%). UPLC-MS (method A): Rt. 1.72 min (TIC); ionization ES$^+$378 [M+H]$^+$. $^1$H NMR (400 MHz, DMSO-d$_6$): δ 12.98 (s, 1H), 7.48 (d, J=9.0 Hz, 1H), 7.07 (d, J=9.0 Hz, 1H), 5.42 (t, J=4.8 Hz, 1H), 4.16-4.07 (m, 2H), 2.50 (s, 3H), 2.33 (bs, 6H), 2.11 (dt, J=15.0, 4.2 Hz, 2H), 2.05-1.98 (m, 4H), 1.64 (dt, J=6.7, 2.8 Hz, 2H). $^{13}$C NMR (101 MHz, DMSO-d$_6$): δ 162.39, 154.95, 133.48, 130.73, 117.69, 114.40, 99.50, 68.55, 54.98, 36.88, 27.96, 20.86, 13.49.

Example 54. (1R,3r,5S)-3-(4-Butylphenoxy)-8-[(3,5-dimethyl-1H-pyrazol-4-yl)sulfonyl]-8-azabicyclo[3.2.1]octane (ARN16186)

Following GP4, (1R,3r,5S)-3-(4-butylphenoxy)-8-azabicyclo[3.2.1]octane trifluoroacetate (0.21 g, 1.1 eq., 0.57 mmol) was dissolved in THF (4.0 mL). Triethylamine (0.29 mL, 4 eq., 2.08 mmol) was then added followed by 3,5-dimethyl-1H-pyrazole-4-sulfonyl chloride (0.1 g, 1.0 eq., 0.52 mmol). The reaction mixture was stirred at room temperature for 16 h. Then it was quenched by the addition of HCl 2N (5 mL) and extracted with EtOAc (2×5 mL). The organic extracts were dried over $Na_2SO_4$ and concentrated in vacuo to furnish the crude product, which was purified by flash chromatography eluting with DCM/MeOH (0 to 5%) to give the pure title compound as white solid (0.158 g, 73%). $^1$H NMR (400 MHz, DMSO-d$_6$): δ 12.98 (bs, 1H), 7.31-6.86 (m, 2H), 6.86-6.60 (m, 2H), 4.61 (t, J=4.7 Hz, 1H), 4.17-3.94 (m, 2H), 2.51-2.45 (m, 2H), 2.31 (s, 6H), 2.09-1.87 (m, 6H), 1.66-1.55 (m, 2H), 1.56-1.41 (m, 2H), 1.36-1.12 (m, 2H), 0.88 (t, J=7.3 Hz, 3H). $^{13}$C NMR (101 MHz, DMSO-d$_6$): δ 155.11, 134.82, 129.78, 115.84, 114.93, 69.32, 55.46, 36.81, 34.36, 33.80, 28.38, 22.15, 14.22, 11.74.

Evaluation of the Biological Activity

The experiments carried out to evaluate the inhibition of ROS production using the compounds of the invention were based on the method reported by Danli W. and Patricia Yotnda in Production and Detection of Reactive Oxygen Species (ROS) in Cancers, J. Vis Exp. 2011; (57):3357.

Measurement of ROS Production

Cultured brain Neuroblastoma2A (Neuro2A) were used.

15.000 Cells were plated in a 96 well plate with black walls and transparent flat bottom in 100 μL of DMEM complete medium (including 10% fetal bovine serum, 100 mM L-Glutamine) containing compounds at indicated concentrations or 0.5% dimethylsulfoxide (DMSO), and kept overnight at 37° C. to allow them to attach to the plate. The following day the culture medium was removed, cells were washed with 100 μl of Phosphate Buffer Saline, pH 7.4 (PBS) and loaded with 100 μL of PBS containing 10 μM of dichloro-dihydro-fluorescein diacetate (DCFH-DA) and compounds at the indicated concentrations (or DMSO 0.5%) for additional 45 min at 37° C. DCFH-DA was prepared as a 20 mM stock in (DMSO) and kept in the dark at 4° C.

ROS production was induced by exposure with 0.2 mM $H_2O_2$ dissolved in 100 μl of complete DMEM medium without phenol red. Fluorescence intensity was measured at an emission/excitation wavelengths of 485/535 nm and ROS production was monitored for 2 h, at 37° C. The results relating to the inhibition of ROS production in Neuro2A cells are reported in table 1 herein below.

The structure of the tested compound is shown in Table 2

TABLE 1

Inhibition of ROS production in neuro 2A cells

| Example | 5 μM (inhibition) | 10 μM (inhibition) |
|---|---|---|
| 54 (ARN16186) | 17% | 114% |
| 03 | 39% | 136% |
| 08 | 0% | 77% |
| 09 | 35% | 56% |
| 15 | 0% | 84% |
| 52 | 9% | 27% |
| 51 | 0% | 21% |
| 40 | 19% | 86% |
| Salvianolic Acid B[#] 100 μM | | 100% |

[#]Salvianolic acid B is a cell protective antioxidant and free radical scavenger, used as reference compound in the assay.

TABLE 2

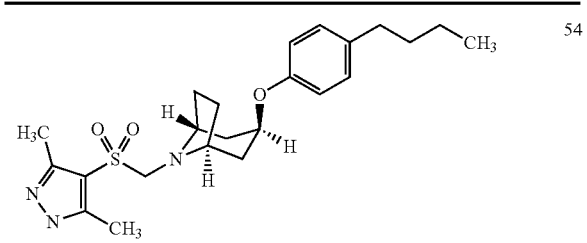

54

(ARN16186)

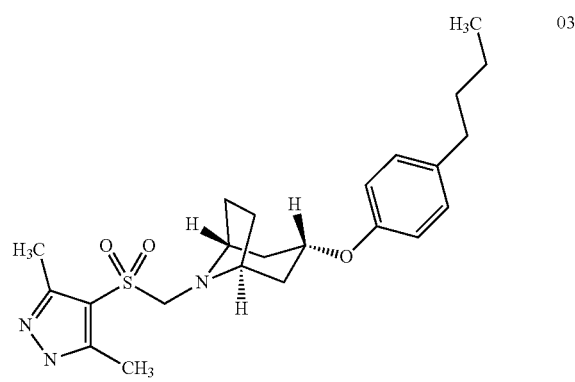

03

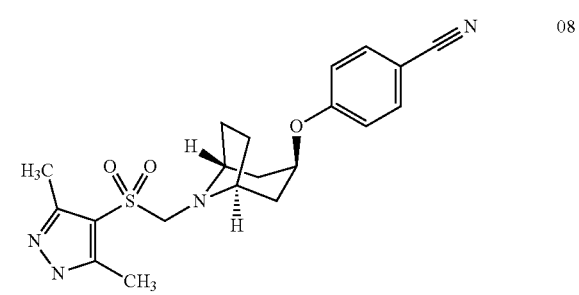

08

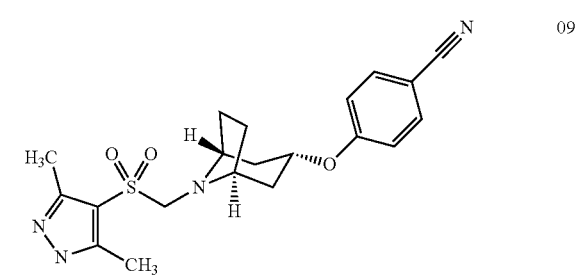

09

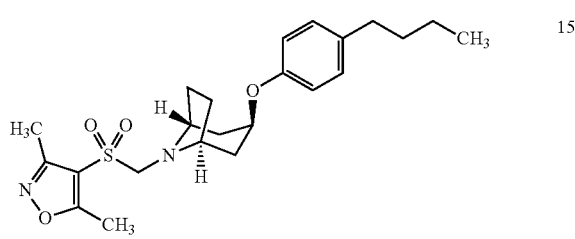

15

TABLE 2-continued

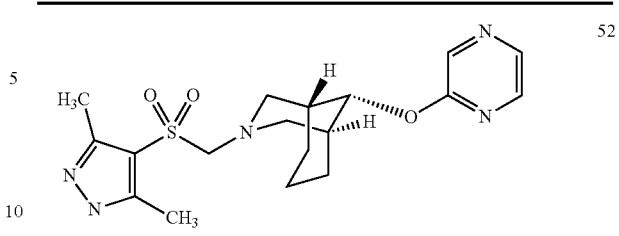

52

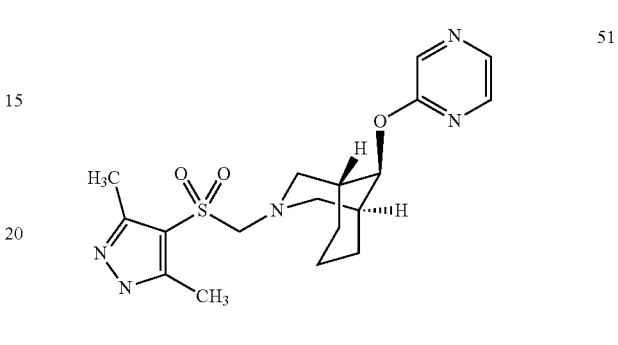

51

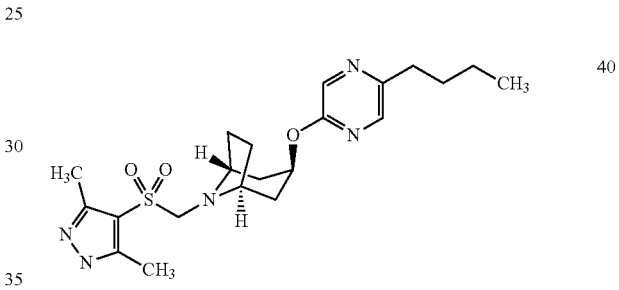

40

Evaluation of the h-NAAA Activity

Cell Culture Conditions

Human recombinant proteins were obtained from HEK-293 stable overexpressing NAAA cell lines. Cells were grown in Dulbecco's modified Eagle medium (DMEM) containing 10% FBS, 1% penicillin/streptomycin, 1% glutamine and 500 μg/mL G418. To obtain membrane preparation cells were scraped off with cold phosphate-buffered saline (PBS) and collected by centrifugation (300×g, 7 min, 4° C.). Cell pellet were stored at −80° C. until protein preparation.

In Vitro Human NAAA Assay

Preparation of Enzyme-Enriched Lysate (h-NAAA).

HEK-293 cells stably transfected with the human NAAA coding sequences were used as enzyme source. Cell pellets were suspended in 20 mM Tris HCl (pH 7.4) with 0.32 M sucrose, sonicated and centrifuged at 800×g for 30 min at 4° C. Supernatants were then ultracentrifuged at 12,000×g for 30 min at 4° C. Pellets were re-suspended in PBS buffer (pH 7.4) and subjected to three freeze-thaw cycles at −80° C. The suspension was finally ultracentrifuged at 105,000×g for 1 h at 4° C., supernatants were collected, protein concentration was measured and samples aliquoted and stored at −80° C. until use.

The results are summarized in Table 3 as follows, wherein +: $IC_{50}>2$ μM; ++: 1.0 μM<$IC_{50}$<2 μM; +++: $IC_{50}$<1 μM:

TABLE 3

| Example | Structure | Substance Name | Formula | Activity h-NAAA Fluorogenic assay |
|---------|-----------|----------------|---------|-----------------------------------|
| 01 | 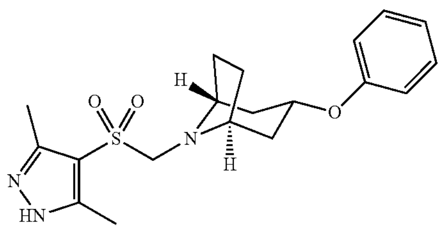 [SMILES: Cc1n[nH]c(C)c1S(=O)(=O)CN1[C@@H]2CC[C@H]1CC(Oc1ccccc1)C2] | (1R,3s,5S)-8-[(3,5-Dimethyl-1H-pyrazol-4-yl)sulfonyl]-3-phenoxy-8-azabicyclo[3.2.1]octane | C18 H23 N3 O3 S | +++ |
| 02 | 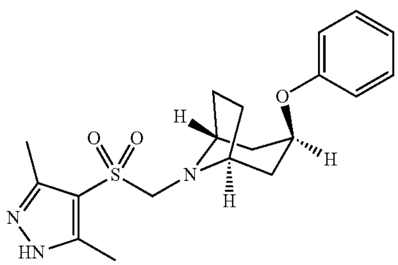 [SMILES: Cc1n[nH]c(C)c1S(=O)(=O)CN1[C@@H]2CC[C@H]1C[C@H](Oc1ccccc1)C2] | (1R,3r,5S)-8-[(3,5-Dimethyl-1H-pyrazol-4-yl)sulfonyl]-3-phenoxy-8-azabicyclo[3.2.1]octane | C18 H23 N3 O3 S | +++ |
| 03 | 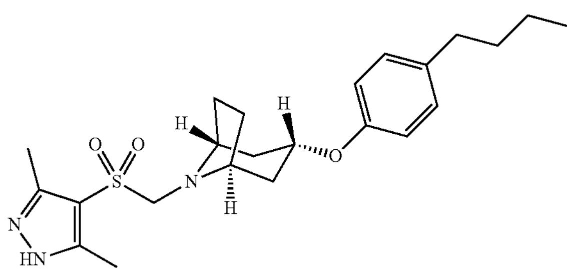 [SMILES: CCCCc1ccc(O[C@H]2C[C@H]3CC[C@@H](C2)N3CS(=O)(=O)c2c(C)n[nH]c2C)cc1] | (1R,3s,5S)-3-(4-Butylphenoxy)-8-[(3,5-dimethyl-1H-pyrazol-4-yl)sulfonyl]-8-azabicyclo[3.2.1]octane | C22 H31 N3 O3 S | + |
| 04 | 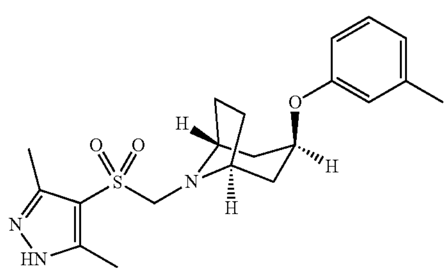 [SMILES: Cc1cccc(O[C@@H]2C[C@H]3CC[C@@H](C2)N3CS(=O)(=O)c2c(C)n[nH]c2C)c1] | (1R,3r,5S)-3-(3-Methylphenoxy)-8-[(3,5-dimethyl-1H-pyrazol-4-yl)sulfonyl]-8-azabicyclo[3.2.1]octane | C19 H25 N3 O3 S | +++ |
| 05 | 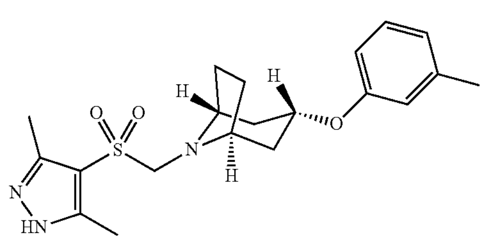 [SMILES: Cc1cccc(O[C@H]2C[C@H]3CC[C@@H](C2)N3CS(=O)(=O)c2c(C)n[nH]c2C)c1] | (1R,3s,5S)-3-(3-Methylphenoxy)-8-[(3,5-dimethyl-1H-pyrazol-4-yl)sulfonyl]-8-azabicyclo[3.2.1]octane | C19 H25 N3 O3 S | + |

TABLE 3-continued

| Example | Structure | Substance Name | Formula | Activity h-NAAA Fluorogenic assay |
|---|---|---|---|---|
| 06 | 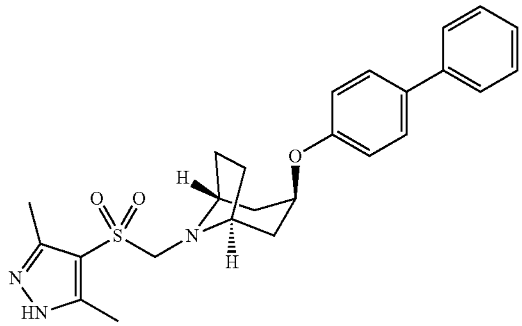 [SMILES: Cc1n[nH]c(C)c1S(=O)(=O)CN1[C@@H]2CC[C@H]1C[C@H](Oc1ccc(-c3ccccc3)cc1)C2] | (1R,3r,5S)-3-(4-phenylphenoxy)-8-[(3,5-dimethyl-1H-pyrazol-4-yl)sulfonyl]-8-azabicyclo[3.2.1]octane | C24 H27 N3 O3 S | ++ |
| 07 | 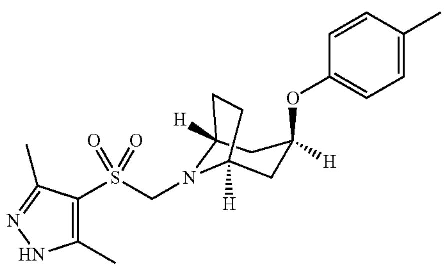 [SMILES: Cc1ccc(O[C@@H]2C[C@H]3CC[C@@H](C2)N3CS(=O)(=O)c2c(C)n[nH]c2C)cc1] | (1R,3r,5S)-3-(4-methylphenoxy)-8-[(3,5-dimethyl-1H-pyrazol-4-yl)sulfonyl]-8-azabicyclo[3.2.1]octane | C19 H25 N3 O3 S | +++ |
| 08 | 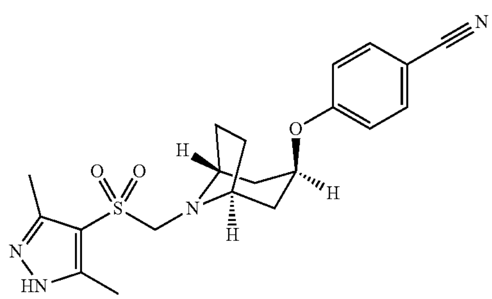 [SMILES: Cc1n[nH]c(C)c1S(=O)(=O)CN1[C@@H]2CC[C@H]1C[C@H](Oc1ccc(C#N)cc1)C2] | (1R,3r,5S)-3-(4-Cyanophenoxy)-8-[(3,5-dimethyl-1H-pyrazol-4-yl)sulfonyl]-8-azabicyclo[3.2.1]octane | C19 H22 N4 O3 S | +++ |
| 09 | 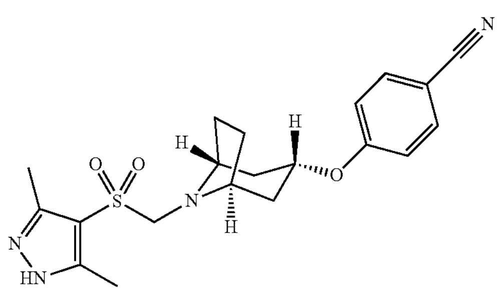 [SMILES: Cc1n[nH]c(C)c1S(=O)(=O)CN1[C@@H]2CC[C@H]1C[C@@H](Oc1ccc(C#N)cc1)C2] | (1R,3s,5S)-3-(4-Cyanophenoxy)-8-[(3,5-dimethyl-1H-pyrazol-4-yl)sulfonyl]-8-azabicyclo[3.2.1]octane | C19 H22 N4 O3 S | + |
| 10 | 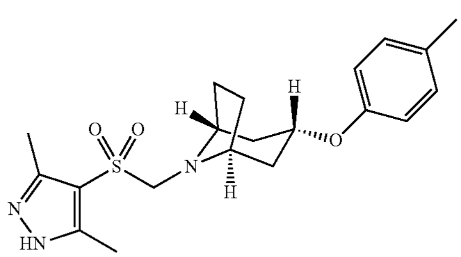 [SMILES: Cc1ccc(O[C@H]2C[C@H]3CC[C@@H](C2)N3CS(=O)(=O)c2c(C)n[nH]c2C)cc1] | (1R,3s,5S)-3-(4-methylphenoxy)-8-[(3,5-dimethyl-1H-pyrazol-4-yl)sulfonyl]-8-azabicyclo[3.2.1]octane | C19 H25 N3 O3 S | + |

TABLE 3-continued

| Example | Structure | Substance Name | Formula | Activity h-NAAA Fluorogenic assay |
|---|---|---|---|---|
| 11 | 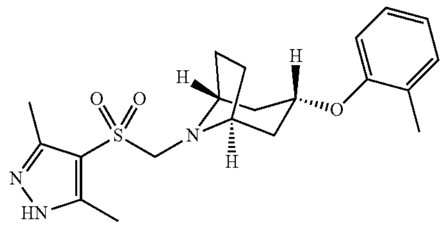 [SMILES: Cc1ccccc1O[C@H]1C[C@H]2CC[C@@H](C1)N2CS(=O)(=O)c1c(C)n[nH]c1C] | (1R,3s,5S)-3-(2-methylphenoxy)-8-[(3,5-dimethyl-1H-pyrazol-4-yl)sulfonyl]-8-azabicyclo[3.2.1]octane | C19 H25 N3 O3 S | + |
| 12 | 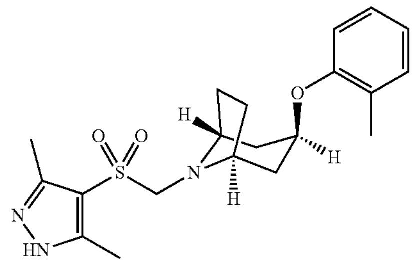 [SMILES: Cc1ccccc1O[C@@H]1C[C@H]2CC[C@@H](C1)N2CS(=O)(=O)c1c(C)n[nH]c1C] | (1R,3r,5S)-3-(2-methylphenoxy)-8-[(3,5-dimethyl-1H-pyrazol-4-yl)sulfonyl]-8-azabicyclo[3.2.1]octane | C19 H25 N3 O3 S | +++ |
| 13 | 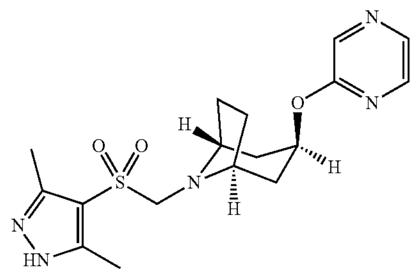 [SMILES: Cc1n[nH]c(C)c1S(=O)(=O)CN1[C@@H]2CC[C@H]1C[C@H](Oc1cnccn1)C2] | (1R,3r,5S)-8-[(3,5-Dimethyl-1H-pyrazol-4-yl)sulfonyl]-3-pyrazin-2-yloxy-8-azabicyclo[3.2.1]octane | C16 H21 N5 O3 S | +++ |
| 14 | 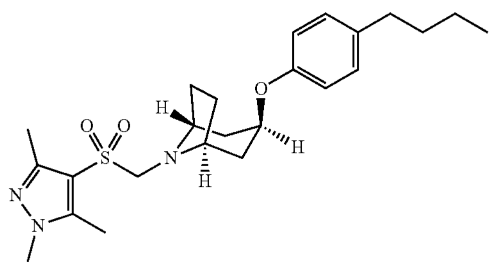 [SMILES: CCCCc1ccc(O[C@@H]2C[C@H]3CC[C@@H](C2)N3CS(=O)(=O)c2c(C)nn(C)c2C)cc1] | (1R,3r,5S)-3-(4-Butylphenoxy)-8-(1,3,5-trimethyl-pyrazol-4-yl)sulfonyl-8-azabicyclo[3.2.1]octane | C23 H33 N3 O3 S | +++ |
| 15 | 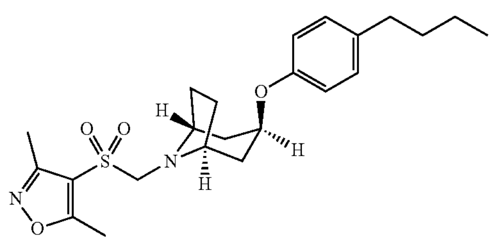 [SMILES: CCCCc1ccc(O[C@@H]2C[C@H]3CC[C@@H](C2)N3CS(=O)(=O)c2c(C)noc2C)cc1] | 4-[[(1R,3r,5S)-3-(4-Butylphenoxy)-8-azabicyclo[3.2.1]octan-8-yl]sulfonyl]-3,5-dimethyl-isoxazole | C22 H30 N2 O4 S | + |
| 16 | 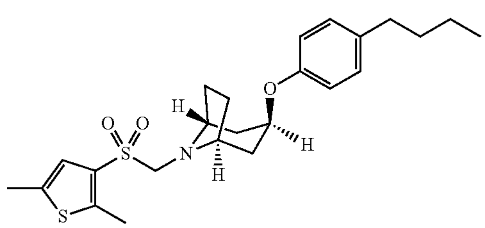 [SMILES: CCCCc1ccc(O[C@@H]2C[C@H]3CC[C@@H](C2)N3CS(=O)(=O)c2cc(C)sc2C)cc1] | (1R,3r,5S)-3-(4-Butylphenoxy)-8-[(2,5-dimethyl-3-thienyl)sulfonyl]-8-azabicyclo[3.2.1]octane | C23 H31 N O3 S2 | + |

TABLE 3-continued

| Example | Structure | Substance Name | Formula | Activity h-NAAA Fluorogenic assay |
|---|---|---|---|---|
| 17 | 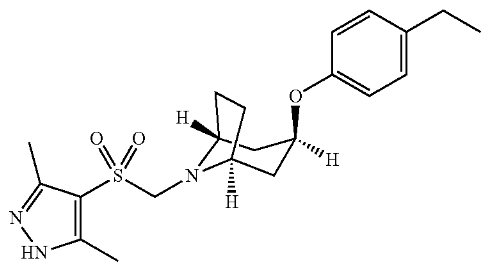 [SMILES: CCc1ccc(O[C@@H]2C[C@H]3CC[C@@H](C2)N3CS(=O)(=O)c2c(C)n[nH]c2C)cc1] | (1R,3r,5S)-3-(4-Ethylphenoxy)-8-[(3,5-dimethyl-1H-pyrazol-4-yl)sulfonyl]-8-azabicyclo[3.2.1]octane | C20 H27 N3 O3 S | +++ |
| 18 | 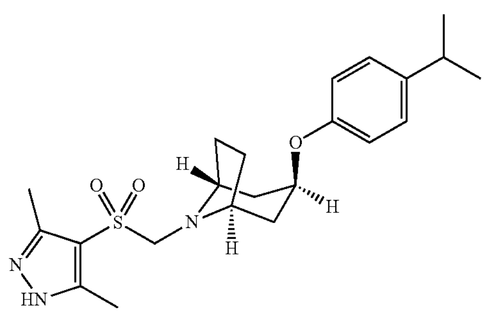 [SMILES: Cc1n[nH]c(C)c1S(=O)(=O)CN1[C@@H]2CC[C@H]1C[C@H](Oc1ccc(C(C)C)cc1)C2] | (1R,3r,5S)-3-(4-Isopropyl-phenoxy)-8-[(3,5-dimethyl-1H-pyrazol-4-yl)sulfonyl]-8-azabicyclo[3.2.1]octane | C21 H29 N3 O3 S | +++ |
| 19 | 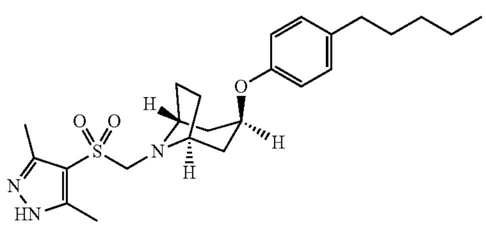 [SMILES: CCCCCc1ccc(O[C@@H]2C[C@H]3CC[C@@H](C2)N3CS(=O)(=O)c2c(C)n[nH]c2C)cc1] | (1R,3r,5S)-3-(4-Hexylphenoxy)-8-[(3,5-dimethyl-1H-pyrazol-4-yl)sulfonyl]-8-azabicyclo[3.2.1]octane | C24 H35 N3 O3 S | +++ |
| 20 | 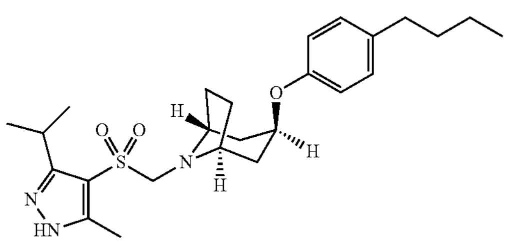 [SMILES: CCCCc1ccc(O[C@@H]2C[C@H]3CC[C@@H](C2)N3CS(=O)(=O)c2c(C(C)C)n[nH]c2C)cc1] | (1R,3r,5S)-3-(4-Butylphenoxy)-8-[(3-isopropyl-5-methyl-1H-pyrazol-4-yl)sulfonyl]-8-azabicyclo[3.2.1]octane | C24 H35 N3 O3 S | +++ |
| 21 | 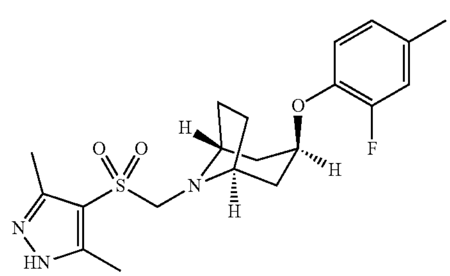 [SMILES: Cc1ccc(O[C@@H]2C[C@H]3CC[C@@H](C2)N3CS(=O)(=O)c2c(C)n[nH]c2C)c(F)c1] | (1R,3r,5S)-3-(2-Fluoro-4-methylphenoxy)-8-[(3,5-dimethyl-1H-pyrazol-4-yl)sulfonyl]-8-azabicyclo[3.2.1]octane | C19 H24 N3 O3 S | +++ |

TABLE 3-continued

| Example | Structure | Substance Name | Formula | Activity h-NAAA Fluorogenic assay |
|---|---|---|---|---|
| 22 | 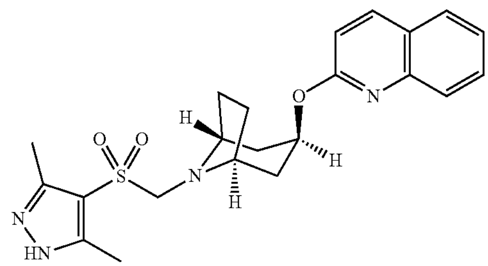 [SMILES: Cc1n[nH]c(C)c1S(=O)(=O)CN1[C@@H]2CC[C@H]1C[C@H](Oc1ccc3ccccc3n1)C2] | (1R,3r,5S)-8-[(3,5-Dimethyl-1H-pyrazol-4-yl)sulfonyl]-3-(2-quinolyloxy)-8-azabicyclo[3.2.1]octane | C21 H24 N4 O3 S | + |
| 23 | 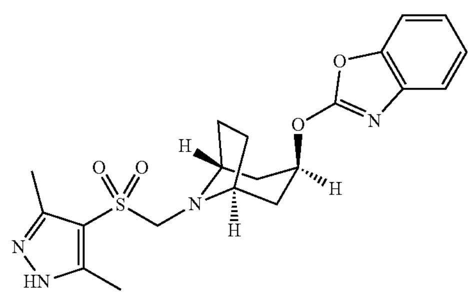 [SMILES: Cc1n[nH]c(C)c1S(=O)(=O)CN1[C@@H]2CC[C@H]1C[C@H](Oc1nc3ccccc3o1)C2] | (1R,3r,5S)-8-[(3,5-Dimethyl-1H-pyrazol-4-yl)sulfonyl]-3-(2-benzoxazoloxy)-8-azabicyclo[3.2.1]octane | C19 H22 N4 O4 S | +++ |
| 24 | 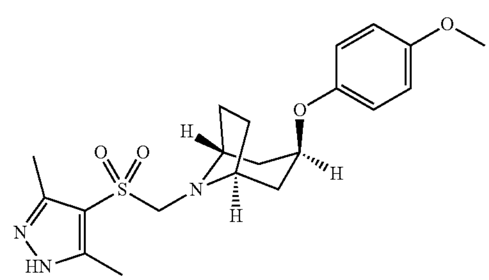 [SMILES: COc1ccc(O[C@@H]2C[C@H]3CC[C@@H](C2)N3CS(=O)(=O)c2c(C)n[nH]c2C)cc1] | (1R,3r,5S)-3-(4-Methoxyphenoxy)-8-[(3,5-dimethyl-1H-pyrazol-4-yl)sulfonyl]-8-azabicyclo[3.2.1]octane | C19 H25 N3 O4 S | +++ |
| 25 | 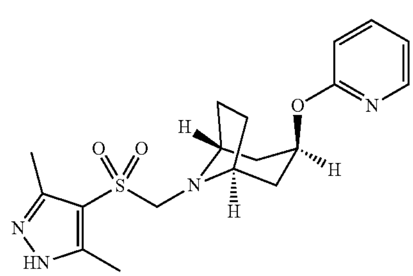 [SMILES: Cc1n[nH]c(C)c1S(=O)(=O)CN1[C@@H]2CC[C@H]1C[C@H](Oc1ccccn1)C2] | (1R,3r,5S)-8-[(3,5-Dimethyl-1H-pyrazol-4-yl)sulfonyl]-3-(2-pyridiloxy)-8-azabicyclo[3.2.1]octane | C17 H22 N4 O3 S | +++ |
| 26 | 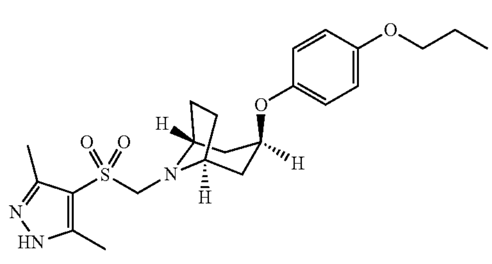 [SMILES: CCCOc1ccc(O[C@@H]2C[C@H]3CC[C@@H](C2)N3CS(=O)(=O)c2c(C)n[nH]c2C)cc1] | (1R,3r,5S)-3-(4-Propoxyphenoxy)-8-[(3,5-dimethyl-1H-pyrazol-4-yl)sulfonyl]-8-azabicyclo[3.2.1]octane | C21 H29 N3 O4 S | +++ |

TABLE 3-continued

| Example | Structure | Substance Name | Formula | Activity h-NAAA Fluorogenic assay |
|---|---|---|---|---|
| 27 | 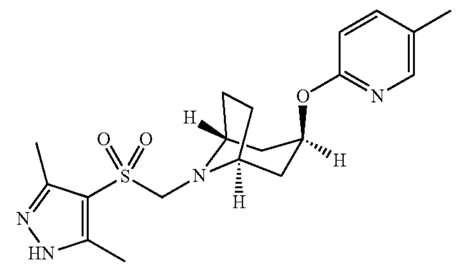 [SMILES: Cc1ccc(O[C@@H]2C[C@H]3CC[C@@H](C2)N3CS(=O)(=O)c2c(C)n[nH]c2C)nc1] | (1R,3r,5S)-8-[(3,5-Dimethyl-1H-pyrazol-4-yl)sulfonyl]-3-[(5-methyl-2-pyridil)oxy]-8-azabicyclo[3.2.1]octane | C18 H24 N4 O3 S | +++ |
| 28 | 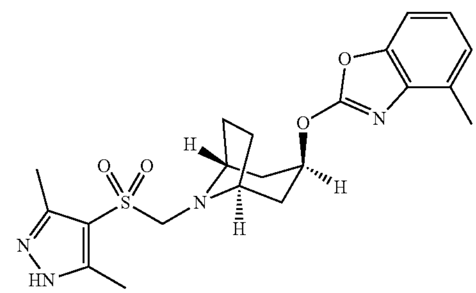 [SMILES: Cc1n[nH]c(C)c1S(=O)(=O)CN1[C@@H]2CC[C@H]1C[C@H](Oc1nc3c(C)cccc3o1)C2] | (1R,3r,5S)-8-[(3,5-Dimethyl-1H-pyrazol-4-yl)sulfonyl]-3-(2-(4-methyl)-benzoxazoloxy)-8-azabicyclo[3.2.1]octane | C20 H24 N4 O4 S | + |
| 29 | 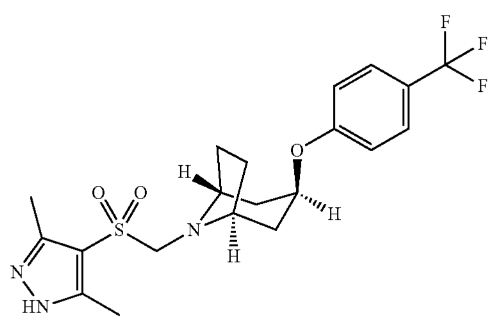 [SMILES: Cc1n[nH]c(C)c1S(=O)(=O)CN1[C@@H]2CC[C@H]1C[C@H](Oc1ccc(C(F)(F)F)cc1)C2] | (1R,3r,5S)-3-(4-Trifluoromethyl-phenoxy)-8-[(3,5-dimethyl-1H-pyrazol-4-yl)sulfonyl]-8-azabicyclo[3.2.1]octane | C19 H22 F3 N3 O3 S | +++ |
| 30 | 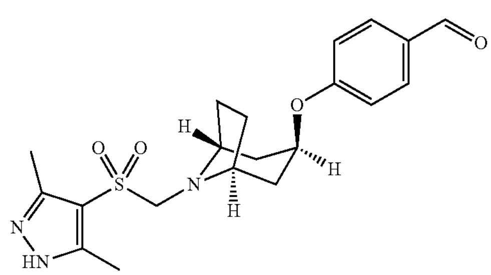 [SMILES: Cc1n[nH]c(C)c1S(=O)(=O)CN1[C@@H]2CC[C@H]1C[C@H](Oc1ccc(C=O)cc1)C2] | (1R,3r,5S)-3-(4-Formyl-phenoxy)-8-[(3,5-dimethyl-1H-pyrazol-4-yl)sulfonyl]-8-azabicyclo[3.2.1]octane | C19 H23 N3 O4 S | +++ |
| 31 | 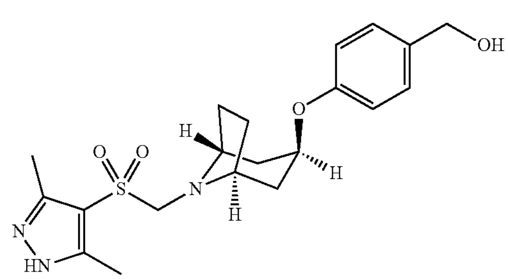 [SMILES: Cc1n[nH]c(C)c1S(=O)(=O)CN1[C@@H]2CC[C@H]1C[C@H](Oc1ccc(CO)cc1)C2] | (1R,3r,5S)-3-(4-Hydroxymethyl-phenoxy)-8-[(3,5-dimethyl-1H-pyrazol-4-yl)sulfonyl]-8-azabicyclo[3.2.1]octane | C19 H25 N3 O4 S | +++ |

TABLE 3-continued

| Example | Structure | Substance Name | Formula | Activity h-NAAA Fluorogenic assay |
|---|---|---|---|---|
| 32 | 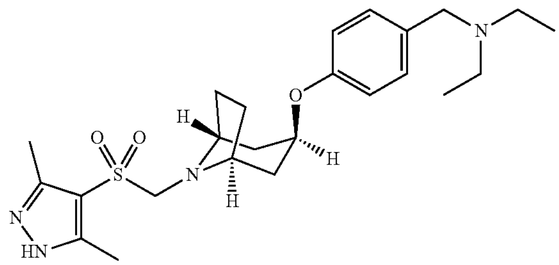 [SMILES: CCN(CC)Cc1ccc(O[C@@H]2C[C@H]3CC[C@@H](C2)N3CS(=O)(=O)c2c(C)n[nH]c2C)cc1] | (1R,3r,5S)-3-[4-Diethylamino-methyl-phenoxy]-8-[(3,5-dimethyl-1H-pyrazol-4-yl)sulfonyl]-8-azabicyclo[3.2.1]octane | C23 H34 N4 O3 S | + |
| 33 | 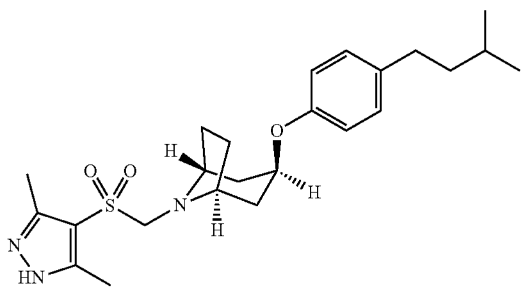 [SMILES: Cc1n[nH]c(C)c1S(=O)(=O)CN1[C@@H]2CC[C@H]1C[C@H](Oc1ccc(CCC(C)C)cc1)C2] | (1R,3r,5S)-3-[4-Isopentyl-phenoxy]-8-[(3,5-dimethyl-1H-pyrazol-4-yl)sulfonyl]-8-azabicyclo[3.2.1]octane | C23 H33 N3 O3 S | +++ |
| 34 | 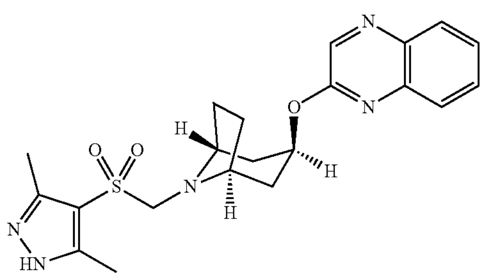 [SMILES: Cc1n[nH]c(C)c1S(=O)(=O)CN1[C@@H]2CC[C@H]1C[C@H](Oc1cnc3ccccc3n1)C2] | (1R,3r,5S)-8-[(3,5-Dimethyl-1H-pyrazol-4-yl)sulfonyl]-3-(2-quinoxalyloxy)-8-azabicyclo[3.2.1]octane | C20 H23 N5 O3 S | + |
| 35 | 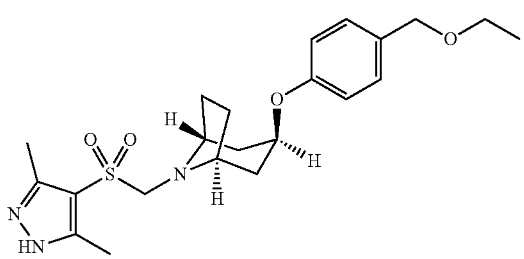 [SMILES: CCOCc1ccc(O[C@@H]2C[C@H]3CC[C@@H](C2)N3CS(=O)(=O)c2c(C)n[nH]c2C)cc1] | (1R,3r,5S)-3-(4-Ethoxymethyl-phenoxy)-8-[(3,5-dimethyl-1H-pyrazol-4-yl)sulfonyl]-8-azabicyclo[3.2.1]octane | C21 H29 N3 O4 S | +++ |
| 36 | 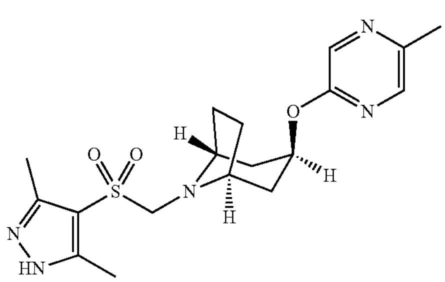 [SMILES: Cc1cnc(O[C@@H]2C[C@H]3CC[C@@H](C2)N3CS(=O)(=O)c2c(C)n[nH]c2C)cn1] | (1R,3r,5S)-8-[(3,5-Dimethyl-1H-pyrazol-4-yl)sulfonyl]-3-(5-methylpyrazin-2-yl)oxy-8-azabicyclo[3.2.1]octane | C17 H23 N5 O3 S | +++ |

TABLE 3-continued

| Example | Structure | Substance Name | Formula | Activity h-NAAA Fluorogenic assay |
|---|---|---|---|---|
| 37 | 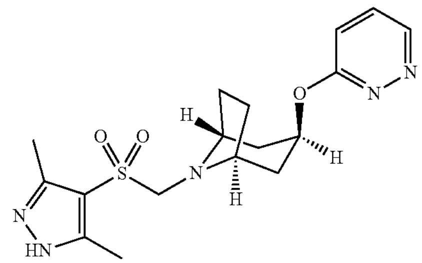 [SMILES: Cc1n[nH]c(C)c1S(=O)(=O)CN1[C@@H]2CC[C@H]1C[C@H](Oc1cccnn1)C2] | (1R,3r,5S)-8-[(3,5-Dimethyl-1H-pyrazol-4-yl)sulfonyl]-3-pyridazin-3-yloxy-8-azabicyclo[3.2.1]octane | C16 H21 N5 O3 S | + |
| 38 | 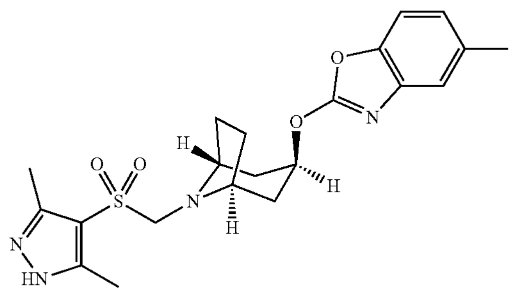 [SMILES: Cc1ccc2oc(O[C@@H]3C[C@H]4CC[C@@H](C3)N4CS(=O)(=O)c3c(C)n[nH]c3C)nc2c1] | (1R,3r,5S)-8-[(3,5-Dimethyl-1H-pyrazol-4-yl)sulfonyl]-3-(2-(5-methyl)-benzoxazoloxy)-8-azabicyclo[3.2.1]octane | C20 H24 N4 O4 S | +++ |
| 39 | 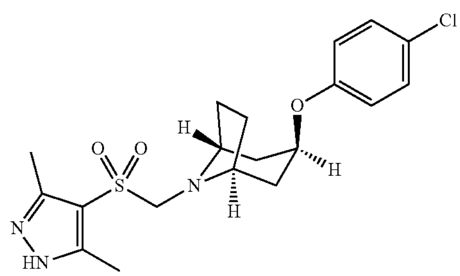 [SMILES: Cc1n[nH]c(C)c1S(=O)(=O)CN1[C@@H]2CC[C@H]1C[C@H](Oc1ccc(Cl)cc1)C2] | (1R,3r,5S)-3-(4-Chloro-phenoxy)-8-[(3,5-dimethyl-1H-pyrazol-4-yl)sulfonyl]-8-azabicyclo[3.2.1]octane | C18 H22 Cl N3 O3 S | +++ |
| 40 | 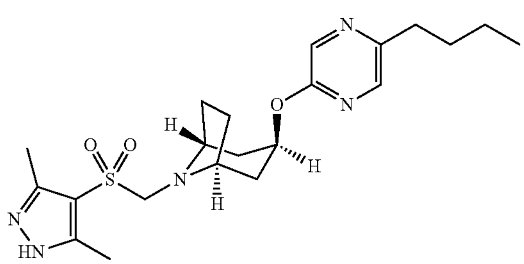 [SMILES: CCCCc1cnc(O[C@@H]2C[C@H]3CC[C@@H](C2)N3CS(=O)(=O)c2c(C)n[nH]c2C)cn1] | (1R,3r,5S)-8-[(3,5-Dimethyl-1H-pyrazol-4-yl)sulfonyl]-3-[5-butylpyrazin-2-yl]oxy-8-azabicyclo[3.2.1]octane | C20 H29 N5 O3 S | +++ |
| 41 | 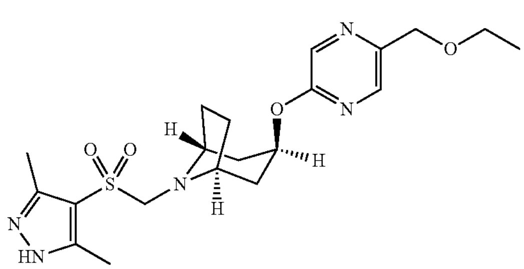 [SMILES: CCOCc1cnc(O[C@@H]2C[C@H]3CC[C@@H](C2)N3CS(=O)(=O)c2c(C)n[nH]c2C)cn1] | (1R,3r,5S)-8-[(3,5-Dimethyl-1H-pyrazol-4-yl)sulfonyl]-3-[5-(ethoxymethyl)pyrazin-2-yl]oxy-8-azabicyclo[3.2.1]octane | C19 H27 N5 O4 S | +++ |

TABLE 3-continued

| Example | Structure | Substance Name | Formula | Activity h-NAAA Fluorogenic assay |
|---|---|---|---|---|
| 42 | 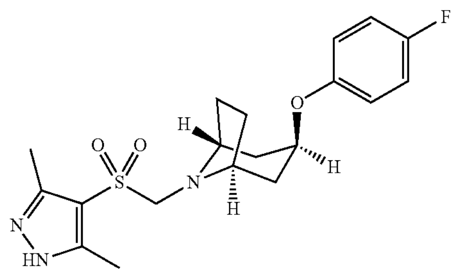 [SMILES: Cc1n[nH]c(C)c1S(=O)(=O)CN1[C@@H]2CC[C@H]1C[C@H](Oc1ccc(F)cc1)C2] | (1R,3r,5S)-3-(4-Fluoro-phenoxy)-8-[(3,5-dimethyl-1H-pyrazol-4-yl)sulfonyl]-8-azabicyclo[3.2.1]octane | C18 H22 N3 O3 S | +++ |
| 43 | 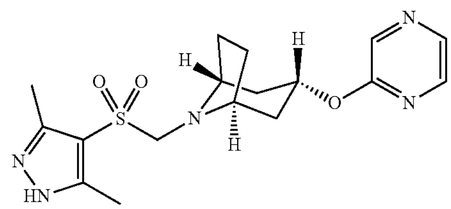 [SMILES: Cc1n[nH]c(C)c1S(=O)(=O)CN1[C@@H]2CC[C@H]1C[C@@H](Oc1cnccn1)C2] | (1R,3s,5S)-8-[(3,5-Dimethyl-1H-pyrazol-4-yl)sulfonyl]-3-pyridazin-3-yloxy-8-azabicyclo[3.2.1]octane | C16 H21 N5 O3 S | + |
| 44 | 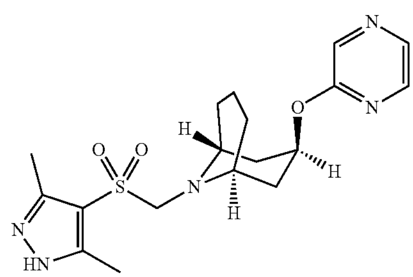 [SMILES: Cc1n[nH]c(C)c1S(=O)(=O)CN1[C@@H]2CCC[C@H]1C[C@H](Oc1cnccn1)C2] | (1R,3r,5S)-9-[(3,5-Dimethyl-1H-pyrazol-4-yl)sulfonyl]-3-(pyrazin-2-yloxy)-9-azabicyclo[3.3.1]nonane | C17 H23 N5 O3 S | +++ |
| 45 | 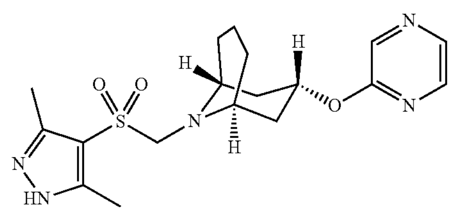 [SMILES: Cc1n[nH]c(C)c1S(=O)(=O)CN1[C@@H]2CCC[C@H]1C[C@@H](Oc1cnccn1)C2] | (1R,3s,5S)-9-[(3,5-Dimethyl-1H-pyrazol-4-yl)sulfonyl]-3-(pyrazin-2-yloxy)-9-azabicyclo[3.3.1]nonane | C17 H23 N5 O3 S | + |
| 46 | 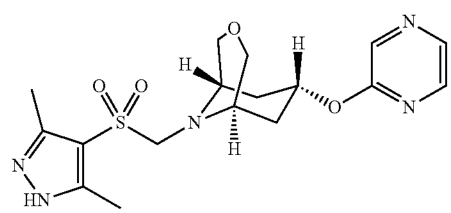 [SMILES: Cc1n[nH]c(C)c1S(=O)(=O)CN1[C@@H]2COC[C@H]1C[C@@H](Oc1cnccn1)C2] | (1R,3s,5S)-9-[(3,5-Dimethyl-1H-pyrazol-4-yl)sulfonyl]-7-pyrazin-2-yloxy-3-oxa-9-azabicyclo[3.3.1]nonane | C16 H21 N5 O4 S | + |
| 47 | 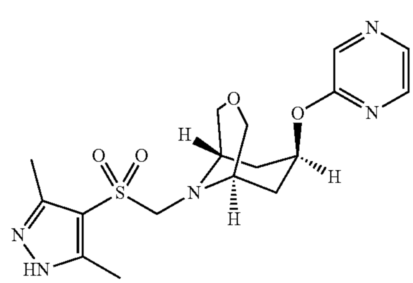 [SMILES: Cc1n[nH]c(C)c1S(=O)(=O)CN1[C@@H]2COC[C@H]1C[C@H](Oc1cnccn1)C2] | (1R,3r,5S)-9-[(3,5-Dimethyl-1H-pyrazol-4-yl)sulfonyl]-7-pyrazin-2-yloxy-3-oxa-9-azabicyclo[3.3.1]nonane | C16 H21 N5 O4 S | + |

TABLE 3-continued

| Example | Structure | Substance Name | Formula | Activity h-NAAA Fluorogenic assay |
|---|---|---|---|---|
| 48 | 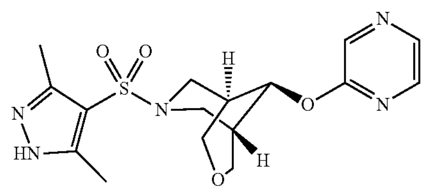 [SMILES: Cc1n[nH]c(C)c1S(=O)(=O)N1C[C@H]2COC[C@@H](C1)[C@H]2Oc1cnccn1] | (1R,5S,9r)-7-((3,5-Dimethyl-1H-pyrazol-4-yl)sulfonyl)-9-(pyrazin-2-yloxy)-3-oxa-7-azabicyclo[3.3.1]nonane | C16 H21 N5 O4 S | + |
| 49 | 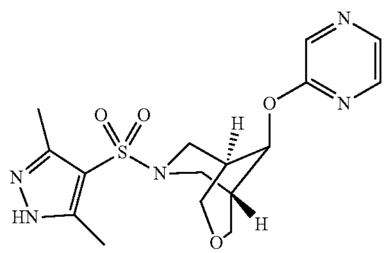 [SMILES: Cc1n[nH]c(C)c1S(=O)(=O)N1C[C@H]2COC[C@@H](C1)C2Oc1cnccn1] | (1R,5S,9s)-7-((3,5-Dimethyl-1H-pyrazol-4-yl)sulfonyl)-9-(pyrazin-2-yloxy)-3-oxa-7-azabicyclo[3.3.1]nonane | C16 H21 N5 O4 S | + |
| 50 | 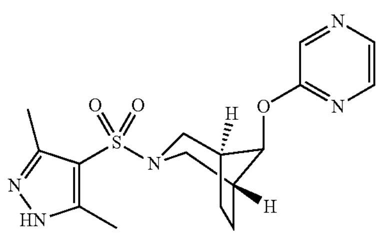 [SMILES: Cc1n[nH]c(C)c1S(=O)(=O)N1C[C@H]2CC[C@@H](C1)C2Oc1cnccn1] | (1R,5S,8r)-3-((3,5-Dimethyl-1H-pyrazol-4-yl)sulfonyl)-8-(pyrazin-2-yloxy)-3-azabicyclo[3.2.1]octane | C16 H21 N5 O3 S | + |
| 51 | 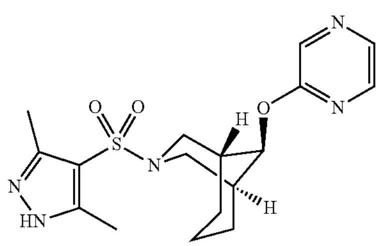 [SMILES: Cc1n[nH]c(C)c1S(=O)(=O)N1C[C@H]2CCC[C@@H](C1)[C@@H]2Oc1cnccn1] | (1R,5S,9r)-3-((3,5-Dimethyl-1H-pyrazol-4-yl)sulfonyl)-9-(pyrazin-2-yloxy)-3-azabicyclo[3.3.1]nonane | C17 H23 N5 O3 S | + |
| 52 | 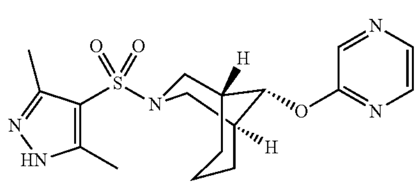 [SMILES: Cc1n[nH]c(C)c1S(=O)(=O)N1C[C@H]2CCC[C@@H](C1)[C@H]2Oc1cnccn1] | (1R,5S,9s)-3-((3,5-Dimethyl-1H-pyrazol-4-yl)sulfonyl)-9-(pyrazin-2-yloxy)-3-azabicyclo[3.3.1]nonane | C17 H23 N5 O3 S | +++ |
| 53 | 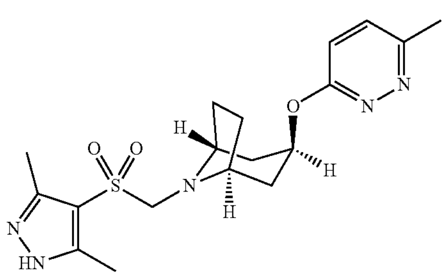 [SMILES: Cc1ccc(O[C@@H]2C[C@H]3CC[C@@H](C2)N3CS(=O)(=O)c2c(C)n[nH]c2C)nn1] | (1R,3r,5S)-8-[(3,5-Dimethyl-1H-pyrazol-4-yl)sulfonyl]-3-(6-methylpyridazin-3-yl)oxy-8-azabicyclo[3.2.1]octane | C17 H23 N5 O3 S | + |

TABLE 3-continued

| Example | Structure | Substance Name | Formula | Activity h-NAAA Fluorogenic assay |
|---|---|---|---|---|
| 54 (ARN-16186) | 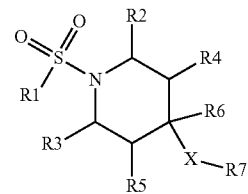 | (1R,3r,5S)-3-(4-Butylphenoxy)-8-[(3,5-dimethyl-1H-pyrazol-4-yl)sulfonyl]-8-azabicyclo[3.2.1]octane | C22 H31 N3 O3 S | +++ |

The present invention also provides pharmaceutical compositions of compounds of formula I for use as brain-cell death protectants and for modulating the levels of PEA and OEA in a subject.

The pharmaceutical compositions of the invention encompass any composition made by admixing compound of the invention and a pharmaceutically acceptable carrier and/or excipient or diluent. Such a compositions are suitable for pharmaceutical use in animal or human.

The pharmaceutical composition comprises a compound of formula I or a pharmaceutical acceptable salt thereof, as an active ingredient and a pharmaceutically acceptable carrier and/or excipient or diluent and may optionally comprise other therapeutic ingredients.

The composition includes compositions suitable for topical, parenteral, pulmonary, nasal, rectal or oral administration.

In some embodiments, the pharmaceutical compositions comprise the active agent of formula I formulated in dosage units which may contain from 0.1 to 1000 mg of the compounds of the invention per dosage unit for daily administration.

The amount of therapeutically active compound that is administered and the dosage regimen for treating a disease condition with the compounds and/or compositions of this invention depends on a variety of factors, including the age, weight, sex and medical condition of the subject, the severity of the disease, the route and frequency of administration, and the particular compound employed, and thus may vary widely. Typically, a daily dose can be administered in one to four doses per day.

For therapeutic or prophylactic purposes, contemplated compounds are ordinarily combined with one or more excipients appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other excipients and modes of administration are well and widely known in the pharmaceutical art.

Contemplated compounds and compositions may be useful in the prevention and/or treatment of diseases that involve oxidative stress and/or decreased of PEA levels. Among other examples, such diseases may include neuropathic pain, trigeminal neuralgia, postherpetic neuralgia, diabetic neuropathy, cancer pain, phantom limb pain, complex regional pain syndrome, and fibromyalgia; rheumatoid arthritis, ankolysing spondylitis, ulcerative colitis, tendonitis, psoriasis, Faber's Disease, Crohn's Disesase, rhinitis, skin allergies, asthma, and autoimmune diseases with inflammatory components such as multiple sclerosis and other demyelenating disorders; Alzheimer's Disease, Parkinson's Disease and traumatic brain injury. Other for which contemplated compounds may be useful includes various metabolic disorders, appetite regulation, and obesity.

The invention claimed is:

1. A compound having the structure of Formula I,

Formula I wherein:
R1 represents an unsubstituted or a substituted pyrazolyl or isoxazolyl ring;
R2, R3, R4 and R5 are independently selected from the group consisting of hydrogen, alkyl, hydroxyalkyl and alkyl-O-alkyl;
provided that either R2 and R3 or R4 and R5 are linked or taken together to form a bridge between the carbon atoms to which R2 and R3 or R4 and R5 respectively are directly linked wherein the heterocyclic N-containing ring shown in Formula I has a meaning selected from the group consisting of:

A1 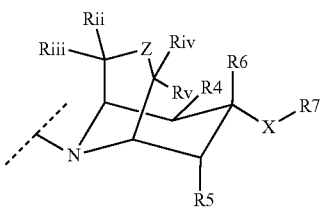

A2 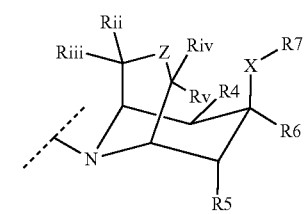

A3 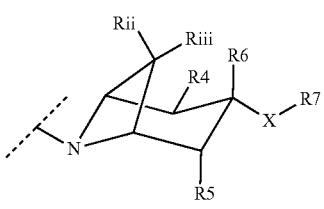

A4 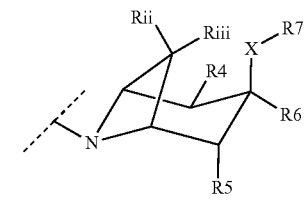

B1 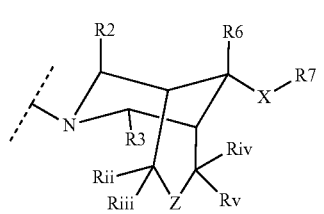

B2 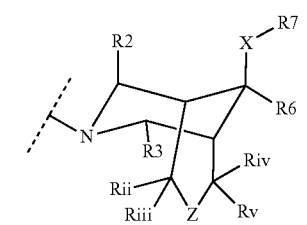

B3 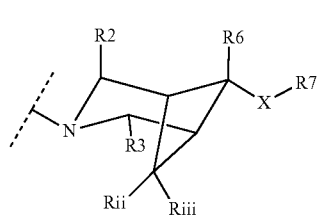

B4 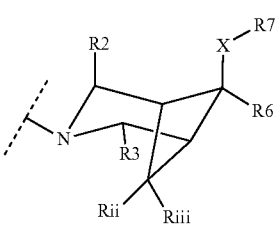

wherein Z is selected from $CR^{vi}R^{vii}$, O, or can be absent;
$R^{ii}$, $R^{iii}$, $R^{iv}$ and $R^{v}$ are independently selected from the group consisting of hydrogen and alkyl;
$R^{vi}$ and $R^{vii}$ are independently selected from the group consisting of hydrogen and alkyl;
R6 is independently selected from the group consisting of hydrogen, alkyl, haloalkyl, cyano and halogen;
X is selected from the group consisting of O, S and $NR^{x}$;
$R^{x}$ is independently selected from the group consisting of hydrogen and alkyl;
R7 is selected from the group consisting of phenyl, pyrimidinyl, pyrazinyl, pyridazinyl, 1,3-benzoxazolyl, quinolinyl, and quinoxalinyl;
or a pharmaceutically acceptable salt, hydrate, solvate, stereoisomer, or racemic mixture thereof.

2. A compound according to claim 1, wherein R1 is a pyrazolyl, which is unsubstituted or mono- or bi-substituted with $C_1$-$C_6$alkyl, halo $C_1$-$C_6$alkyl, $C_3$-$C_6$cycloalkyl, aryl, heteroaryl, $COR^{xi}$, $COOR^{xi}$, heterocycloalkyl, $CONHR^{xi}$, $CONR^{xi}R^{xii}$, OH, O—$C_1$-$C_6$alkyl, O—$C_3$-$C_6$cycloalkyl, O-heterocycloalkyl, O-heteroaryl, O-aryl, O-halo $C_1$-$C_6$alkyl, $C_1$-$C_6$alkyl—O—$C_1$-$C_6$alkyl, $C_1$-$C_6$alkyl—O—$C_3$-$C_6$cycloalkyl, $C_1$-$C_6$alkyl-O-heterocycloalkyl, $C_1$-$C_6$alkyl-O-aryl, CN, $NO_2$, $NR^{xiii}(R^{xii})COR^{xiii}N(R^{xii})COOR^{xiv}$, $N(R^{xii})CONR^{xiii}R^{xiv}$, $N(R^{xii})SOR^{xiii}$, $SOR^{xiii}$, halogen and hydroxy-$C_1$-$C_6$alkyl;
$R^{xi}$ is selected from the group consisting of hydrogen, $C_1$-$C_6$alkyl, aryl, heteroaryl;
$R^{xii}$ is selected from the group consisting of hydrogen, $C_1$-$C_6$alkyl;
$R^{xiii}$ is selected from the group consisting of hydrogen, $C_1$-$C_6$alkyl, $C_3$-$C_6$cycloalkyl, aryl, heteroaryl and hydroxy-$C_1$-$C_6$alkyl;
$R^{xiv}$ is selected from the group consisting of hydrogen, $C_1$-$C_6$alkyl.

3. A compound according to claim 1 wherein R1 is selected from the group consisting of pyrazolyl, and isoxazolyl, unsubstituted or mono- or bi-sub stituted with $C_1$-$C_6$alkyl, halo$C_1$-$C_6$alkyl, $C_3$-$C_6$cycloalkyl, aryl, OH, O—$C_1$-$C_6$alkyl, O-halo $C_1$-$C_6$alkyl, CN, $NO_2$ and halogen.

4. A compound according to claim 1, wherein X is oxygen.

5. A compound according to claim 1 wherein R6 is hydrogen or $C_1$-$C_4$alkyl.

6. A pharmaceutical composition comprising a compound according to claim 1 and a pharmaceutical acceptable carrier, excipient or diluent.

7. A compound according to claim 1, selected from the group consisting of:
(1R,3s,5S)-8-[(3,5-Dimethyl-1H-pyrazol-4-yl)sulfonyl]-3-phenoxy-8-azabicyclo[3.2.1]octane,
(1R,3r,5 S)-8-[(3,5-Dimethyl-1H-pyrazol-4-yl)sulfonyl]-3-phenoxy-8-azabicyclo[3.2.1]octane,
(1R,3s,5 S)-8-[(3,5-Dimethyl-1H-pyrazol-4-yl)sulfonyl]-3-pyridazin-3-yloxy-8-azabicyclo[3.2.1]octane, (1R,3r,5 S)-9-[(3,5-Dimethyl-1H-pyrazol-4-yl)sulfonyl]-3-(pyrazin-2-yloxy)-9-azabicyclo[3.3.1]nonane,
(1R,3 s,5 S)-9-[(3,5-Dimethyl-1H-pyrazol-4-yl)sulfonyl]-3-(pyrazin-2-yloxy)-9-azabicyclo[3.3.1]nonane,
(1R,3s,5 S)-9-[(3,5-Dimethyl-1H-pyrazol-4-yl)sulfonyl]-7-pyrazin-2-yloxy-3-oxa-9-azabicyclo[3.3.1]nonane,
(1R,3r,5 S)-9-[(3, 5-Dimethyl-1H-pyrazol-4-yl)sulfonyl]-7-pyrazin-2-yloxy-3-oxa-9-azabicyclo[3.3.1]nonane,
(1R,5S,9r)-7-(3,5-Dimethyl-1H-pyrazol-4-yl)sulfonyl)-9-(pyrazin-2-yloxy)-3-oxa-7-azabicyclo[3.3.1]nonane,
(1R,5S,9s)-7-(3,5-Dimethyl-1H-pyrazol-4-yl)sulfonyl)-9-(pyrazin-2-yloxy)-3-oxa-7-azabicyclo[3.3.1]nonane,
(1R,5S,8r)-3-(3,5-Dimethyl-1H-pyrazol-4-yl)sulfonyl)-8-(pyrazin-2-yloxy)-3-azabicyclo[3.2.1]octane,
(1R,5S,9r)-3-(3,5-Dimethyl-1H-pyrazol-4-yl)sulfonyl)-9-(pyrazin-2-yloxy)-3-azabicyclo[3.3.1]nonane, and
(1R,5S,9s)-3-(3,5-Dimethyl-1H-pyrazol-4-yl)sulfonyl)-9-(pyrazin-2-yloxy)-3-azabicyclo[3.3.1]nonane.

\* \* \* \* \*